(12) United States Patent
Xia et al.

(10) Patent No.: US 10,008,677 B2
(45) Date of Patent: Jun. 26, 2018

(54) MATERIALS FOR ORGANIC LIGHT EMITTING DIODE

(71) Applicant: Universal Display Corporation, Ewing, NJ (US)

(72) Inventors: Chuanjun Xia, Lawrenceville, NJ (US); Bin Ma, Plainsboro, NJ (US); David Zenan Li, Princeton, NJ (US); Bert Alleyne, Newtown, PA (US); Alan DeAngelis, Pennington, NJ (US); James Fiordeliso, Yardley, PA (US); Vadim Adamovich, Yardley, PA (US)

(73) Assignee: UNIVERSAL DISPLAY CORPORATION, Ewing, NJ (US)

( * ) Notice: Subject to any disclaimer, the term of this patent is extended or adjusted under 35 U.S.C. 154(b) by 809 days.

(21) Appl. No.: 13/932,546

(22) Filed: Jul. 1, 2013

(65) Prior Publication Data

US 2013/0299795 A1    Nov. 14, 2013

Related U.S. Application Data

(63) Continuation-in-part of application No. 13/006,016, filed on Jan. 13, 2011, now Pat. No. 9,130,177.

(51) Int. Cl.
*H01L 51/00* (2006.01)
*C07F 15/00* (2006.01)

(52) U.S. Cl.
CPC ...... *H01L 51/0085* (2013.01); *C07F 15/0033* (2013.01)

(58) Field of Classification Search
CPC .................................................. H01L 51/0085
See application file for complete search history.

(56) References Cited

U.S. PATENT DOCUMENTS

| 4,769,292 | A | 9/1988 | Tang et al. |
| 5,061,569 | A | 10/1991 | VanSlyke et al. |
| 5,247,190 | A | 9/1993 | Friend et al. |
| 5,554,220 | A | 9/1996 | Forrest et al. |
| 5,703,436 | A | 12/1997 | Forrest et al. |
| 5,707,745 | A | 1/1998 | Forrest et al. |
| 5,834,893 | A | 11/1998 | Bulovic et al. |
| 5,844,363 | A | 12/1998 | Gu et al. |

(Continued)

FOREIGN PATENT DOCUMENTS

| CN | 1589307 A | 3/2005 |
| DE | 102005057963 | 6/2007 |

(Continued)

OTHER PUBLICATIONS

Adachi, Chihaya et al., "Organic Electroluminescent Device Having a Hole Conductor as an Emitting Layer," Appl. Phys. Lett., 55(15): 1489-1491 (1989).

(Continued)

*Primary Examiner* — Alex A Rolland
(74) *Attorney, Agent, or Firm* — Duane Morris LLP

(57) ABSTRACT

Compounds are provided that comprise a ligand having a 5-substituted 2-phenylquinoline. In particular, the 2-phenylquinoline may be substituted with a cycloalkyl containing group at the 5-position. These compounds may be used in organic light emitting devices, in particular as red emitters in the emissive layer of such devices, to provide devices having improved properties.

23 Claims, 3 Drawing Sheets

Formula III

(56) References Cited

U.S. PATENT DOCUMENTS

| | | |
|---|---|---|
| 5,929,194 A | 7/1999 | Woo et al. |
| 5,986,401 A | 11/1999 | Thompson et al. |
| 6,013,982 A | 1/2000 | Thompson et al. |
| 6,087,196 A | 7/2000 | Sturm et al. |
| 6,091,195 A | 7/2000 | Forrest et al. |
| 6,097,147 A | 8/2000 | Baldo et al. |
| 6,166,489 A | 12/2000 | Thompson et al. |
| 6,294,398 B1 | 9/2001 | Kim et al. |
| 6,303,238 B1 | 10/2001 | Thompson et al. |
| 6,337,102 B1 | 1/2002 | Forrest et al. |
| 6,468,819 B1 | 10/2002 | Kim et al. |
| 6,528,187 B1 | 3/2003 | Okada |
| 6,687,266 B1 | 2/2004 | Ma et al. |
| 6,821,645 B2 | 11/2004 | Igarashi et al. |
| 6,835,469 B2 * | 12/2004 | Kwong ............... C07D 215/04 313/504 |
| 6,911,271 B1 | 6/2005 | Lamansky et al. |
| 6,913,710 B2 | 7/2005 | Farrand et al. |
| 6,921,915 B2 | 7/2005 | Takiguchi et al. |
| 6,939,624 B2 | 9/2005 | Lamansky et al. |
| 6,939,625 B2 | 9/2005 | Marks et al. |
| 7,001,536 B2 | 2/2006 | Thompson et al. |
| 7,071,615 B2 | 7/2006 | Lu et al. |
| 7,084,273 B2 | 8/2006 | Stossel et al. |
| 7,087,321 B2 | 8/2006 | Kwong et al. |
| 7,090,928 B2 | 8/2006 | Thompson et al. |
| 7,094,897 B2 | 8/2006 | Stossel et al. |
| 7,147,935 B2 | 12/2006 | Kamatani et al. |
| 7,154,114 B2 | 12/2006 | Brooks et al. |
| 7,198,859 B2 | 4/2007 | Kwong et al. |
| 7,250,226 B2 | 7/2007 | Tokito et al. |
| 7,261,954 B2 | 8/2007 | Thompson et al. |
| 7,279,704 B2 | 10/2007 | Walters et al. |
| 7,329,896 B2 | 2/2008 | Tierney et al. |
| 7,332,232 B2 | 2/2008 | Ma et al. |
| 7,338,722 B2 | 3/2008 | Thompson et al. |
| 7,378,162 B2 | 5/2008 | Jeong et al. |
| 7,393,599 B2 | 7/2008 | Thompson et al. |
| 7,396,598 B2 | 7/2008 | Takeuchi et al. |
| 7,429,426 B2 | 9/2008 | Brown et al. |
| 7,431,968 B1 | 10/2008 | Shtein et al. |
| 7,445,855 B2 | 11/2008 | Mackenzie et al. |
| 7,470,928 B2 | 12/2008 | Jeong et al. |
| 7,534,505 B2 | 5/2009 | Lin et al. |
| 7,534,853 B2 | 5/2009 | Stossel et al. |
| 7,560,176 B2 | 7/2009 | Cheng et al. |
| 7,629,061 B2 | 12/2009 | Gupta et al. |
| 7,740,957 B2 | 6/2010 | Kim et al. |
| 7,799,917 B2 | 9/2010 | Samuel et al. |
| 7,851,072 B2 | 12/2010 | Kwong et al. |
| 7,883,785 B2 | 2/2011 | Stossel et al. |
| 8,017,774 B2 | 9/2011 | Kamatani et al. |
| 8,431,243 B2 | 4/2013 | Kwong et al. |
| 9,130,177 B2 | 9/2015 | Ma et al. |
| 2002/0034656 A1 | 3/2002 | Thompson et al. |
| 2002/0134984 A1 | 9/2002 | Igarashi |
| 2002/0158242 A1 | 10/2002 | Son et al. |
| 2003/0059646 A1 | 3/2003 | Kamatani et al. |
| 2003/0072964 A1 | 4/2003 | Kwong et al. |
| 2003/0138657 A1 | 7/2003 | Li et al. |
| 2003/0151042 A1 | 8/2003 | Marks et al. |
| 2003/0152802 A1 | 8/2003 | Tsuboyama et al. |
| 2003/0162053 A1 | 8/2003 | Marks et al. |
| 2003/0175553 A1 | 9/2003 | Thompson et al. |
| 2003/0230980 A1 | 12/2003 | Forrest et al. |
| 2004/0036077 A1 | 2/2004 | Ise |
| 2004/0137267 A1 | 7/2004 | Igarashi et al. |
| 2004/0137268 A1 | 7/2004 | Igarashi et al. |
| 2004/0174116 A1 | 9/2004 | Lu et al. |
| 2005/0025993 A1 | 2/2005 | Thompson et al. |
| 2005/0112407 A1 | 5/2005 | Ogasawara et al. |
| 2005/0238919 A1 | 10/2005 | Ogasawara |
| 2005/0244673 A1 | 11/2005 | Satoh et al. |
| 2005/0260441 A1 | 11/2005 | Thompson et al. |
| 2005/0260449 A1 | 11/2005 | Walters et al. |
| 2006/0008670 A1 | 1/2006 | Lin et al. |
| 2006/0008671 A1 | 1/2006 | Kwong et al. |
| 2006/0127696 A1 | 6/2006 | Stossel et al. |
| 2006/0134459 A1 | 6/2006 | Hou et al. |
| 2006/0202194 A1 | 9/2006 | Jeong et al. |
| 2006/0204785 A1 | 9/2006 | Kim et al. |
| 2006/0228581 A1 | 10/2006 | Seo et al. |
| 2006/0240279 A1 | 10/2006 | Adamovich et al. |
| 2006/0251923 A1 | 11/2006 | Lin et al. |
| 2006/0263635 A1 | 11/2006 | Ise |
| 2006/0280965 A1 | 12/2006 | Kwong et al. |
| 2007/0004918 A1 | 1/2007 | Jeong et al. |
| 2007/0104980 A1 | 5/2007 | Kim et al. |
| 2007/0190359 A1 | 8/2007 | Knowles et al. |
| 2007/0224450 A1 | 9/2007 | Kim et al. |
| 2007/0278936 A1 | 12/2007 | Herron et al. |
| 2007/0278938 A1 | 12/2007 | Yabunouchi et al. |
| 2008/0015355 A1 | 1/2008 | Schafer et al. |
| 2008/0018221 A1 | 1/2008 | Egen et al. |
| 2008/0106190 A1 | 5/2008 | Yabunouchi et al. |
| 2008/0124572 A1 | 5/2008 | Mizuki et al. |
| 2008/0220265 A1 | 9/2008 | Xia et al. |
| 2008/0261076 A1 | 10/2008 | Kwong et al. |
| 2008/0297033 A1 | 12/2008 | Knowles et al. |
| 2009/0008605 A1 | 1/2009 | Kawamura et al. |
| 2009/0009065 A1 | 1/2009 | Nishimura et al. |
| 2009/0017330 A1 | 1/2009 | Iwakuma et al. |
| 2009/0030202 A1 | 1/2009 | Iwakuma et al. |
| 2009/0039776 A1 | 2/2009 | Yamada et al. |
| 2009/0045730 A1 | 2/2009 | Nishimura et al. |
| 2009/0045731 A1 | 2/2009 | Nishimura et al. |
| 2009/0078317 A1 | 3/2009 | Kim et al. |
| 2009/0085476 A1 | 4/2009 | Park et al. |
| 2009/0101870 A1 | 4/2009 | Pakash et al. |
| 2009/0104472 A1 | 4/2009 | Je et al. |
| 2009/0108737 A1 | 4/2009 | Kwong et al. |
| 2009/0115316 A1 | 5/2009 | Zheng et al. |
| 2009/0153037 A1 | 6/2009 | Kim et al. |
| 2009/0159130 A1 | 6/2009 | Eum et al. |
| 2009/0165846 A1 | 7/2009 | Johannes et al. |
| 2009/0165860 A1 | 7/2009 | Kim et al. |
| 2009/0167162 A1 | 7/2009 | Lin et al. |
| 2009/0179554 A1 | 7/2009 | Kuma et al. |
| 2010/0090591 A1 | 4/2010 | Alleyne et al. |
| 2012/0153816 A1 * | 6/2012 | Takizawa ............. C07D 215/04 313/504 |
| 2014/0246656 A1 | 9/2014 | Inoue et al. |

FOREIGN PATENT DOCUMENTS

| | | |
|---|---|---|
| EP | 0650955 | 5/1995 |
| EP | 1239526 | 9/2002 |
| EP | 1348711 | 10/2003 |
| EP | 1725079 | 11/2006 |
| EP | 1783132 | 5/2007 |
| EP | 2034538 | 3/2009 |
| EP | 2055710 | 5/2009 |
| EP | 2080795 | 7/2009 |
| EP | 2085450 | 8/2009 |
| JP | H09-279136 | 10/1997 |
| JP | 2003073387 | 3/2003 |
| JP | 200511610 | 1/2005 |
| JP | 2007123392 | 5/2007 |
| JP | 2007254297 | 10/2007 |
| JP | 2008074939 | 4/2008 |
| KR | 100662379 B1 | 1/2007 |
| KR | 10-2007-0079009 | 8/2007 |
| WO | 199921935 | 5/1999 |
| WO | 200057676 | 9/2000 |
| WO | 200070655 | 11/2000 |
| WO | 2001039234 | 5/2001 |
| WO | 200141512 | 6/2001 |
| WO | 200159030 | 8/2001 |
| WO | 2002002714 | 1/2002 |
| WO | 200215645 | 2/2002 |
| WO | 2002066552 | 8/2002 |
| WO | 2003033617 | 4/2003 |
| WO | 2003040256 | 5/2003 |
| WO | 2003040257 | 5/2003 |

(56) References Cited

FOREIGN PATENT DOCUMENTS

| | | |
|---|---|---|
| WO | 2003060956 | 7/2003 |
| WO | 2004026886 | 4/2004 |
| WO | 2004041962 | 5/2004 |
| WO | 2004093207 | 10/2004 |
| WO | 2004107822 | 12/2004 |
| WO | 2005014551 | 2/2005 |
| WO | 2005019373 | 3/2005 |
| WO | 2005021678 | 3/2005 |
| WO | 2005027583 | 3/2005 |
| WO | 2005030900 | 4/2005 |
| WO | 2005089025 | 9/2005 |
| WO | 2005123873 | 12/2005 |
| WO | 2005124889 | 12/2005 |
| WO | 2006000544 | 1/2006 |
| WO | 2006001150 | 1/2006 |
| WO | 2006009024 | 1/2006 |
| WO | 2006014599 | 2/2006 |
| WO | 2006035997 | 4/2006 |
| WO | 2006056418 | 6/2006 |
| WO | 2006072002 | 7/2006 |
| WO | 2006082742 | 8/2006 |
| WO | 2006098120 | 9/2006 |
| WO | 2006100298 | 9/2006 |
| WO | 2006103874 | 10/2006 |
| WO | 2006114966 | 11/2006 |
| WO | 2006132173 | 12/2006 |
| WO | 2007002683 | 1/2007 |
| WO | 2007004113 | 1/2007 |
| WO | 2007004380 | 1/2007 |
| WO | 2007063754 | 6/2007 |
| WO | 2007063796 | 6/2007 |
| WO | 2008056746 | 5/2008 |
| WO | 2008101842 | 8/2008 |
| WO | 2008109824 | 9/2008 |
| WO | 20080109824 | 9/2008 |
| WO | 2008132085 | 11/2008 |
| WO | 2009000673 | 12/2008 |
| WO | 2009003898 | 1/2009 |
| WO | 2009008311 | 1/2009 |
| WO | 2009018009 | 2/2009 |
| WO | 2009050290 | 4/2009 |
| WO | 2009021126 | 5/2009 |
| WO | 2009062578 | 5/2009 |
| WO | 2009063833 | 5/2009 |
| WO | 2009066778 | 5/2009 |
| WO | 2009066779 | 5/2009 |
| WO | 2009086028 | 7/2009 |
| WO | 2009100991 | 8/2009 |
| WO | 20120148511 | 11/2012 |

OTHER PUBLICATIONS

Adachi, Chihaya et al., "Nearly 100% Internal Phosphorescence Efficiency in an Organic Light Emitting Device," J. Appl. Phys., 90(10): 5048-5051 (2001).

Adachi, Chihaya et al., "High-Efficiency Red Electrophosphorescence Devices," Appl. Phys. Lett., 78(11)1622-1624 (2001).

Aonuma, Masaki et al., "Material Design of Hole Transport Materials Capable of Thick-Film Formation in Organic Light Emitting Diodes," Appl. Phys. Lett., 90:183503-1-183503-3.

Baldo et al., Highly Efficient Phosphorescent Emission from Organic Electroluminescent Devices, Nature, vol. 395, 151-154, (1998).

Baldo et al., Very high-efficiency green organic light-emitting devices based on electrophosphorescence, Appl. Phys. Lett., vol. 75, No. 3, 4-6 (1999).

Gao, Zhiqiang et al., "Bright-Blue Electroluminescence From a Silyl-Substituted ter-(phenylene-vinylene) derivative," Appl. Phys. Lett., 74(6): 865-867 (1999).

Guo, Tzung-Fang et al., "Highly Efficient Electrophosphorescent Polymer Light-Emitting Devices," Organic Electronics, 115-20 (2000).

Hamada, Yuji et al., "High Luminance in Organic Electroluminescent Devices with Bis(10-hydroxybenzo[h]quinolinato) beryllium as an Emitter," Chem. Lett., 905-906 (1993).

Holmes, R.J. et al., "Blue Organic Electrophosphorescence Using Exothermic Host-Guest Energy Transfer," Appl. Phys. Lett., 82(15):2422-2424 (2003).

Hu, Nan-Xing et al., "Novel High Tg Hole-Transport Molecules Based on Indolo[3,2-b]carbazoles for Organic Light-Emitting Devices," Synthetic Metals, 111-112:421-424 (2000).

Huang, Jinsong et al., "Highly Efficient Red-Emission Polymer Phosphorescent Light-Emitting Diodes Based on Two Novel Tris(1-phenylisoquinolinato-C2,N)iridium(III) Derivates," Adv. Mater., 19:739-743 (2007).

Huang, Wei-Sheng et al., "Highly Phosphorescent Bis-Cyclometalated Iridium Complexes Containing Benzoimidazole-Based Ligands," Chem. Mater., 16(12):2480-2488 (2004).

Hung, L.S. et al., "Anode Modification in Organic Light-Emitting Diodes by Low-Frequency Plasma Polymerization of CHF3," Appl. Phys. Lett., 78(5):673-675 (2001).

Ikai, Masamichi and Tokito, Shizuo, "Highly Efficient Phosphorescence From Organic Light-Emitting Devices with an Exciton-Block Layer," Appl. Phys. Lett., 79(2):156-158 (2001).

Ikeda, Hisao et al., "P-185 Low-Drive-Voltage OLEDs with a Buffer Layer Having Molybdenum Oxide," SID Symposium Digest, 37:923-926 (2006).

Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater. Chem., 3(3):319-320 (1993).

Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).

Kido, Junji et al., 1,2,4-Triazole Derivative as an Electron Transport Layer in Organic Electroluminescent Devices, Jpn. J. Appl. Phys., 32:L917-L920 (1993).

Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino) triphenylamine (m-MTDATA), as Hole-Transport Materials," Adv. Mater., 6(9):677-679 (1994).

Kwong, Raymond C. et al., "High Operational Stability of Electrophosphorescent Devices," Appl. Phys. Lett., 81(1) 162-164 (2002).

Lamansky, Sergey et al., "Synthesis and Characterization of Phosphorescent Cyclometalated Iridium Complexes," Inorg. Chem., 40(7):1704-1711 (2001).

Lee, Chang-Lyoul et al., "Polymer Phosphorescent Light-Emitting Devices Doped with Tris(2-phenylpyridine) Iridium as a Triplet Emitter," Appl. Phys. Lett., 77(15)2280-2282 (2000).

Lo, Shih-Chun et al., "Blue Phosphorescence from Iridium(III) Complexes at Room Temperature," Chem. Mater., 18(21)5119-5129 (2006).

Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).

Mi, Bao-Xiu et al., "Thermally Stable Hole-Transporting Material for Organic Light-Emitting Diode an Isoindole Derivative," Chem. Mater., 15(16):3148-3151 (2003).

Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4): 592-593 (2005).

Niu, Yu-Hua et al., "Highly Efficient Electrophosphorescent Devices with Saturated Red Emission from a Neutral Osmium Complex," Chem. Mater., 17(13):3532-3536 (2005).

Noda, Tetsuya and Shirota,Yasuhiko, "5,5'-Bis(dimesitylboryl)-2,2'-bithiophene and 5,5"-Bis(dimesitylboryl)-2,2'5',2"-terthiophene as a Novel Family of Electron-Transporting Amorphous Molecular Materials," J. Am. Chem. Soc., 120 (37):9714-9715 (1998).

(56) References Cited

OTHER PUBLICATIONS

Okumoto, Kenji et al., "Green Fluorescent Organic Light-Emitting Device with External Quantum Efficiency of Nearly 10%," Appl. Phys. Lett., 89:063504-1-063504-3 (2006).
Palilis, Leonidas C., "High Efficiency Molecular Organic Light-Emitting Diodes Based on Silole Derivatives and Their Exciplexes," Organic Electronics, 4:113-121 (2003).
Paulose, Betty Marie Jennifer S. et al., "First Examples of Alkenyl Pyridines as Organic Ligands for Phosphorescent Iridium Complexes," Adv. Mater., 16(22):2003-2007 (2004).
Ranjan, Sudhir et al., "Realizing Green Phosphorescent Light-Emitting Materials from Rhenium(I) Pyrazolato Diimine Complexes," Inorg. Chem., 42(4):1248-1255 (2003).
Sakamoto, Youichi et al., "Synthesis, Characterization, and Electron-Transport Property of Perfluorinated Phenylene Dendrimers," J. Am. Chem. Soc., 122(8):1832-1833 (2000).
Salbeck, J. et al., "Low Molecular Organic Glasses for Blue Electroluminescence," Synthetic Metals, 91209-215 (1997).
Shirota, Yasuhiko et al., "Starburst Molecules Based on p-Electron Systems as Materials for Organic Electroluminescent Devices," Journal of Luminescence, 72-74:985-991 (1997).
Sotoyama, Wataru et al., "Efficient Organic Light-Emitting Diodes with Phosphorescent Platinum Complexes Containing NCN-Coordinating Tridentate Ligand," Appl. Phys. Lett., 86:153505-1-153505-3 (2005).
Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).
T. Östergård et al., "Langmuir-Blodgett Light-Emitting Diodes of Poly(3-Hexylthiophene) Electro-Optical Characteristics Related to Structure," Synthetic Metals, 87:171-177 (1997).
Takizawa, Shin-ya et al., "Phosphorescent Iridium Complexes Based on 2-Phenylimidazo[1,2-α]pyridine Ligands Tuning of Emission Color toward the Blue Region and Application to Polymer Light-Emitting Devices," Inorg. Chem., 46(10):4308-4319 (2007).
Tang, C.W. and VanSlyke, S.A., "Organic Electroluminescent Diodes," Appl. Phys. Lett., 51(12):913-915 (1987).
Tung, Yung-Liang et al., "Organic Light-Emitting Diodes Based on Charge-Neutral Ru II PHosphorescent Emitters," Adv. Mater., 17(8)1059-1064 (2005).
Van Slyke, S. A. et al., "Organic Electroluminescent Devices with Improved Stability," Appl. Phys. Lett, 69 (15):2160-2162 (1996).
Wang, Y. et al., "Highly Efficient Electroluminescent Materials Based on Fluorinated Organometallic Iridium Compounds," Appl. Phys. Lett., 79(4):449-451 (2001).
Wong, Keith Man-Chung et al., A Novel Class of Phosphorescent Gold(III) Alkynyl-Based Organic Light-Emitting Devices with Tunable Colour, Chem. Commun., 2906-2908 (2005).
Wong, Wai-Yeung, "Multifunctional Iridium Complexes Based on Carbazole Modules as Highly Efficient Electrophosphors," Angew. Chem. Int. Ed., 45:7800-7803 (2006).
International Search Report in related PCT/US2012/020991 application.
State Intellectual Property Office of the People's Republic of China, Notification and English Version of Chinese Office Action regarding corresponding Chinese Application No. 201210371182.4 dated Jan. 9, 2015, pp. 1-4.
State Intellectual Property Office of the People's Republic of China, Chinese Search Report and English Abstract regarding corresponding Chinese Application No. 201210371182.4 dated Jan. 9, 2015, pp. 1-4.
Foreign Office Action dated Mar. 4, 2014 for corresponding Chinese Application No. 201210371182.4.
Notice of Reasons for Rejection dated Aug. 14, 2014 for corresponding Japanese Application No. 2013-179125.
Japanese Patent Office, Notification of the First Office Action—English Version of Japanese Office Action regarding corresponding Japanese Application No. 2013-549526 dated Apr. 27, 2015, pp. 1-6.
Decision of Rejection dated Mar. 28, 2016 for corresponding JP Patent Application No. 2013-549526.
Burroughes et al., Nature, 1990, 347. 539.
Baldo, et al., Phys. Rev. B, 1999, 60, 14422.
Adachi et al., Appl. Phys. Lett. 2000, 77, 904.
Lamansky et al., J. Am. Chem. Soc., 2001, 123, 4304.
Cotton and Wilkinson, Advanced Inorganic Chemistry, 4th Editiion, John Wiley & Sons, New York 1980.
Shoustikov et al., IEEE Journal of selected topics in quantum electronics, 1998, 4, 3.
Dartnall et al., Proceedings of the Royal Society of London B, 1983, 220, 115.
Gupta et al., Journal of Photochemistry, 1985, 30, 173.
Dolorimetry, Second Edition, Publication CIE Feb. 15, 1986 (ISBN 3-900-734-00-3).
Miyaura et al., Chem. Rev. 1995, 2457.
Haworth, R. D. et al., J. Chem. Soc., 1948, 777.
Lepeltier et al., "Tris-Cyclometalated iridium (III) styryl complexes and their saturated analogues; direct functionalization of IR(4-Meppy)3 and hydrogen transfer process," Organometallics, 2005, 24(24) p. 6069-6072.
Jung et al., "Effect of substitution of methyl groups on the luminescence performance of Ir complexes: preparation, structures, electrochemistry, photophysical properties and their applications in organic light-emitting diodes (OLEDs)," European Journal of Inorganic Chem., 2004, 17:3415-3423.
Yang, et al., "High efficiency mer-iridium complexes for organic light-emitting diodes," Chem. Comm., 2004-19:2232-2233.
Lo et al., "Green phosphorescent dendrimer for light-emitting diodes," Adv. Materials 2002, 14: 975-979.
Kawa et al., "Enhanced luminescence of lanthanide within lanthanide-cored dendrimer complexes", Thin Solid Films 331, (1998) p. 259-263.
Lupton et al., "Control of electrophosphorescence in conjugated dendrimer light-emitting diodes", Advanced Functional Materials 2001, 11, No. 4, p. 287-294.
U.S. Appl. No. 60/811533, filed Jun. 6, 2006, Ma Bin et al.
Vang et al., "Polymer Based Tris(2-Phenylpyridine)Iridium Complexes", Macromolecules: 39(9): 3140-3146. 2006.
Takayama et al., "Soluble Polymer Complexes Having A1Q3-Type Pendent Groups", Macromolecular Rapid Communications, 25:1171-1174. 2004.
Lafolet et al., "Iridium complexes containing p-phenylene units. The influence of the conjugation on the excited state properties". J. of Materials Chemistry. 15(12):2820-2828. 2005.
Bacher et al., Photo-Cross-Linked Triphenylenes as Novel Insoluble Hole Transport Materials in Organic LEDs, Macromolecules 32:4551-4557. 1999.
Bacher et al., "Synthesis and Characterization of Photo-Cross-Linkable Hole-Conducting Polymers". Macromolecules 1640-1647, 2005.
Gellman et al., "New Triarylamine-Containing Polymers as Hole Transport Materials in Organic Light Emitting Diodes: Effect of Polymer Structure and Cross-Linking on Device Characteristics", Chem. Mater. 10:1668-1676. 1998.
Ding et al., "Highly Efficient Green-Emitting Phosphorescent Iridium Dendrimers Based on Carbazole Dendrons", Adv. Funct. Mater. 16:575-58. 2006.
Domercq et al., "Organic Light-Emitting Diodes with Multiple Photocrosslinkable Hole-Transport Layers", J. of Polymer Science: Part B: Polymer Physics. 41:2726-2732. 2003.
Domercq et al., "Photo-Pattemable Hole Transport Polymers for Organic Light Emitting Diodes". Chem. Mater. 15:1491-1496. 2003.
Evans et al., "Triplet Energy Back Transfer in Conjugated Polymers with Pendant Phosphorescent Iridium Complexes". J. Am. Chem. Soc. 128:6647-6656. 2006.
Jiang et al., "High Efficiency Electrophosphorescent Fluorene-alt-carbazole Copolymers N-Grafted with Cyclometalated Ir Complexes", Macromolecules 38:4072-4080. 2005.
Jiang el al., "Perfluorocyclobutane-based arylamine Hole-Transporting Materials for Organic and Polymer Light Emitting Diodes", Adv. Funct. Mater. 12(11-12): 745-751.

(56) References Cited

OTHER PUBLICATIONS

Li et al., "Multifunctional platnium porphyrin dendrimers as emitters in undoped phosphorescent based light emitting devices", Appl. Phys. Lett. 89:061125-1-061125-3.2006.

Liu et al., "Red Phosphorescent Iridium Complex Containing Carbazole-Functionalized rbeta-Diketonate for Highly Efficient Nondoped Organic Light-Emitting Diodes", Adv. Funct. Mater. 16:1441-1448. 2006.

Nuyken et al., "Crosslinkable hole- and electron-transport materials for application in organic light emitting diodes (OLEDs)", Designed Monomers and Polymers 5(2): 195-210. 2002.

Sandee et al., "Solution Processible Conjugated Electrophosphorescent Polymers", J. Am. Chem. Soc. 126:7041-7048. 2004.

Schultz et al., "Enhancement of Phosphorescence of Ir Complexes Bound to Conjugated Polymers: Increasing the Triplet Level of the Main Chain", Macromolecules 39:9157-9165. 2006.

Yong et al., "A multifunctional platinum based triplet emitter for OLED applications", Organometallics 24:4079-4082. 2005.

You et al, "Blue electrophosphorescence from Iridium Complex Covalently Bonded to the Poly (9-dodecyl-3-vinylcarbazole): Suppressed Phase Segregation and Enhanced Energy Transfer", Macromolecules 39:349-356. 2006.

Zhang et al., "Highly Efficient polymer light-emitting diodes using color-tunable carbazole based iridium complexes", Chem. Phys. Lett 422:386-390. 2006.

\* cited by examiner

Formula I

Formula III

MATERIALS FOR ORGANIC LIGHT EMITTING DIODE

CROSS-REFERENCE TO RELATED APPLICATIONS

This application is a continuation-in-part of U.S. patent application Ser. No. 13/006,016, filed on Jan. 13, 2011, the entire contents of which is incorporated herein by reference.

PARTIES TO A JOINT RESEARCH AGREEMENT

The claimed invention was made by, on behalf of, and/or in connection with one or more of the following parties to a joint university corporation research agreement: Regents of the University of Michigan, Princeton University, The University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to organic light emitting devices (OLEDs). More specifically, the present invention is related to phosphorescent materials comprising a ligand having 2-phenylquinoline substituted with a cylcoalkyl group at the 5-position. These materials may be used in OLEDs to provide devices having improved performance.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted $Ir(ppy)_3$, which has the structure:

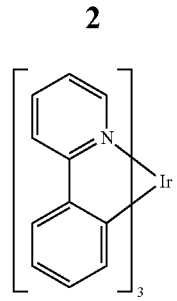

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher"

HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

Compounds comprising a 5-substituted 2-phenylquinoline containing ligand are provided. The compounds comprise a ligand L having the formula:

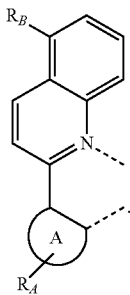

Formula I

A is a 5-membered or 6-membered carbocyclic or heterocyclic ring. Preferably, A is phenyl. $R_A$ may represent mono, di, tri, or tetra substitutions. Each of $R_A$ is independently selected from the group consisting of hydrogen, deuterium, alkyl, silyl, alkoxy, amino, alkenyl, alkynyl, arylkyl, aryl and heteroaryl. $R_B$ is selected from the group consisting of alkyl having at least 2 carbon atoms, amino, alkenyl, alkynyl, arylkyl, and silyl. The ligand L is coordinated to a metal M having an atomic number greater than 40. Preferably, M is Ir.

In one aspect, the compound has the formula:

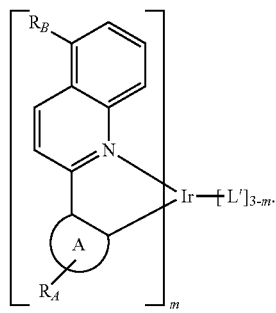

Formula II

L' is an ancillary ligand. m is 1, 2, or 3.

In another aspect, L' is a monoanionic bidentate ligand. In yet another aspect, L' is

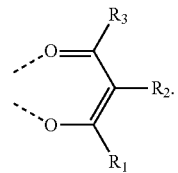

$R_1$, $R_2$, and $R_3$ are independently selected from the group consisting of hydrogen, deuterium, alkyl, alkoxy, amino, alkenyl, alkynyl, arylkyl, aryl and heteroaryl.

In one aspect, the compound has the formula:

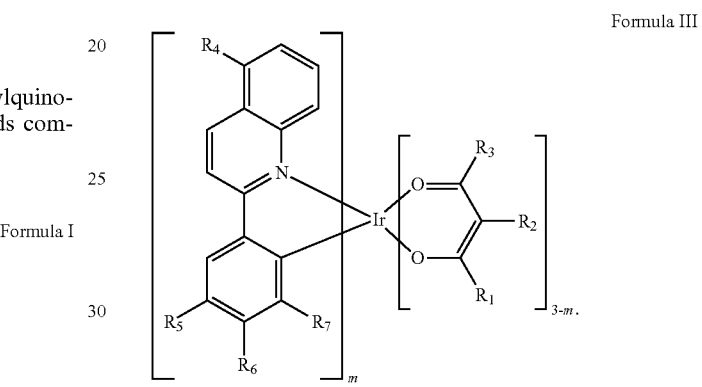

Formula III wherein $R_1$, $R_2$, $R_3$, $R_5$, $R_6$ and $R_7$ are independently selected from the group consisting of hydrogen, deuterium, alkyl, silyl, alkoxy, amino, alkenyl, alkynyl, arylkyl, aryl and heteroaryl. $R_4$ is selected from the group consisting of alkyl having at least 2 carbon atoms, amino, alkenyl, alkynyl, arylkyl, and silyl. m is 1, 2, or 3. Preferably, each of $R_1$ and $R_3$ are a branched alkyl with branching at a position further than the α position to the carbonyl group.

In one aspect, each of $R_5$, $R_6$ and $R_7$ are independently selected from methyl and hydrogen, and at least one of $R_5$, $R_6$ and $R_7$ is methyl. In another aspect, each of $R_5$ and $R_7$ are methyl, and $R_6$ is hydrogen. In yet another aspect, each of $R_5$ and $R_6$ are methyl, and $R_7$ is hydrogen. In a further aspect, each of $R_5$, $R_6$ and $R_7$ are methyl.

In one aspect, $R_4$ is an alkyl group having at least 4 carbon atoms. In another aspect, $R_4$ is an alkyl group having at least 3 carbon atoms.

Specific, non-limiting examples of the 5-substituted 2-phenylquinoline containing compounds are provided. In one aspect, the compound is selected from the group consisting of Compound 1-Compound 50.

In one aspect, $R_4$ comprises a cycloalkyl group having at least 4 carbon atoms. Specific, non-limiting examples of the 5-substituted 2-phenylquinoline containing compound having Formula III wherein $R_4$ comprises a cycloalkyl group having at least 4 carbon atoms is selected from the group consisting of Compound II-1-Compound II-72.

Additionally, a first device comprising an organic light emitting device is provided. The organic light emitting device further comprises an anode, a cathode; and an organic layer, disposed between the anode and the cathode. The organic layer comprises a compound comprising a ligand L having Formula I.

A is a 5-membered or 6-membered carbocyclic or heterocyclic ring. Preferably, A is phenyl. $R_A$ may represent mono, di, tri, or tetra substitutions. Each of $R_A$ is independently selected from the group consisting of hydrogen, alkyl, alkoxy, amino, alkenyl, alkynyl, arylkyl, aryl and heteroaryl. $R_B$ is selected from the group consisting of alkyl having at least 2 carbon atoms, amino, alkenyl, alkynyl, arylkyl, and silyl. The ligand L is coordinated to a metal M having an atomic number greater than 40. Preferably, M is Ir.

Specific, non-limiting examples of devices comprising the compounds are provided. In one aspect, the compound used in the first device is selected from the group consisting of Compound 1-Compound 50.

The various specific aspects discussed above for compounds comprising a ligand L having Formula I are also applicable to a compound comprising a ligand L having Formula I that is used in the first device. In particular, specific aspects of $R_A$, $R_B$, A, L', M, m, $R_1$, $R_2$, $R_3$, $R_4$, $R_5$, $R_6$, and $R_7$ of the compound comprising a ligand L having Formula I discussed above are also applicable to a compound comprising a ligand L having Formula I that is used in a the first device.

In one aspect, the organic layer is an emissive layer and the compound is an emissive dopant. In another aspect, the organic layer further comprises a host. In yet another aspect, the host is a metal 8-hydroxyquinolate. Preferably, the host is:

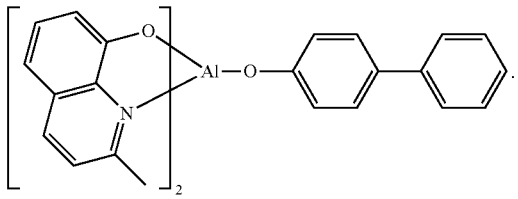

In one aspect, the first device is a consumer product. In another aspect, the first device is an organic light emitting device.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
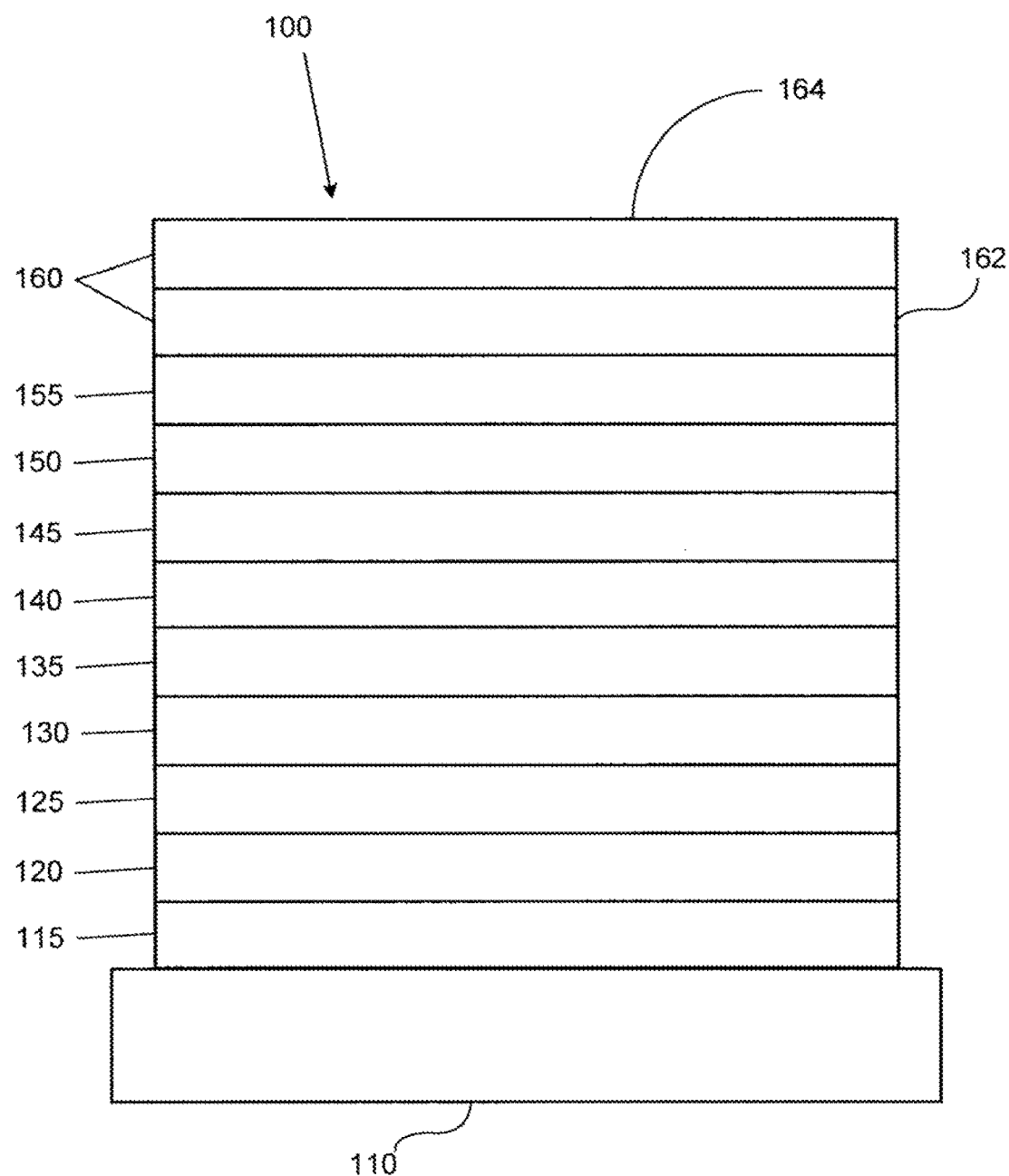
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, and a cathode 160. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with F.sub.4-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
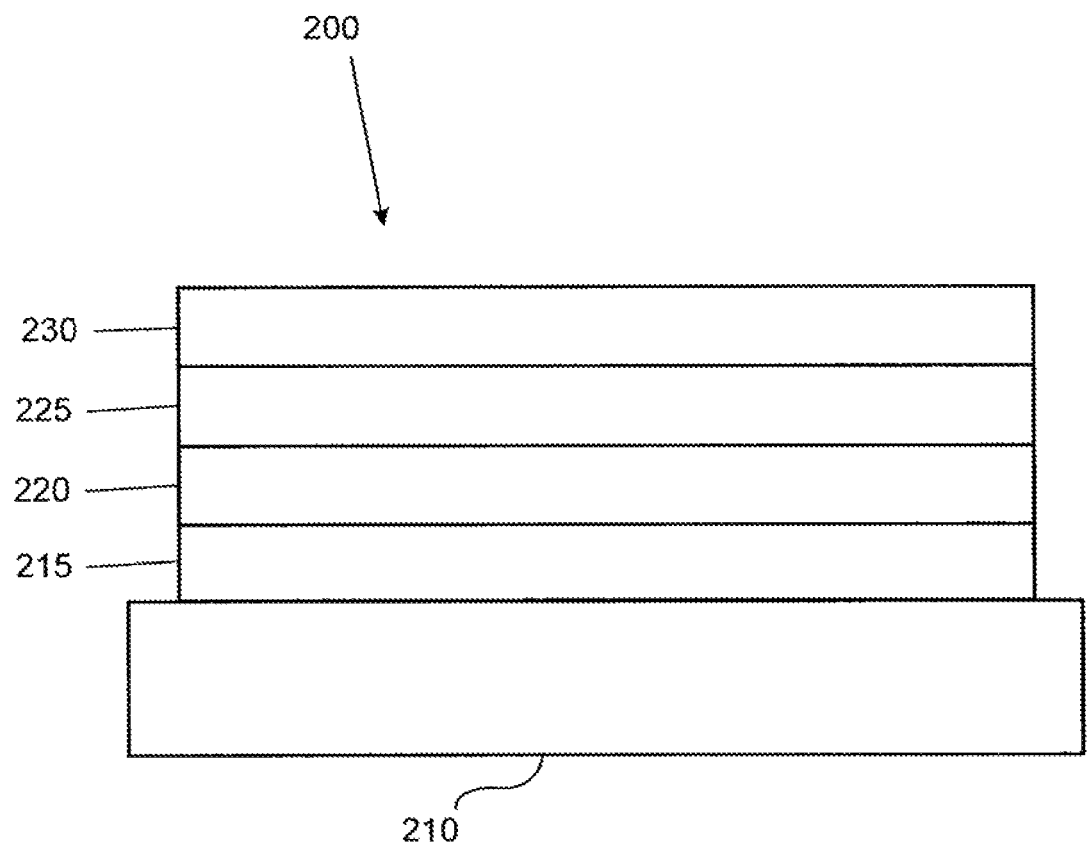
FIG. 2 shows an inverted organic light emitting device that does not have a separate electron transport layer.
Figure 3:
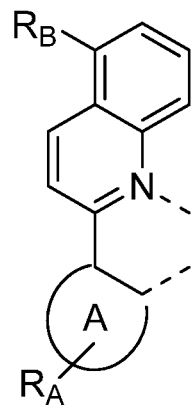
FIG. 3 shows an exemplary compound comprising a 5-substituted 2-phenylquinoline ligand (top) and a preferred embodiment of the 5-substituted 2-phenylquinoline compound (bottom).
Figure 3:
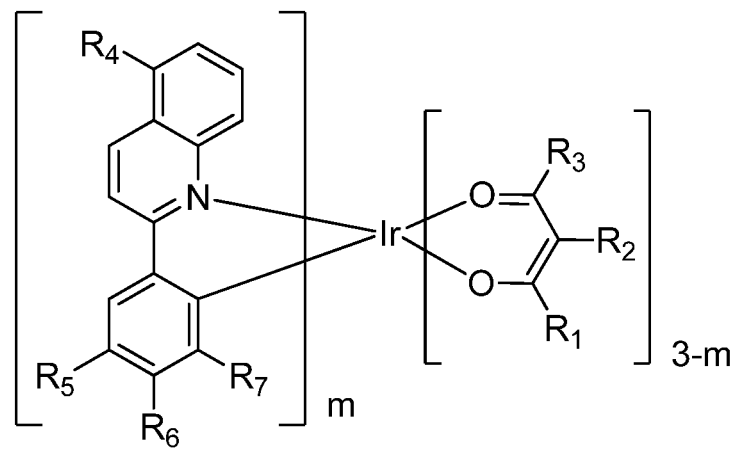

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve outcoupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. patent application Ser. No. 10/233,470, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processability than those having symmetric structures, because asymmetric materials may have a lower tendency to recrystallize. Dendrimer substituents may be used to enhance the ability of small molecules to undergo solution processing.

Devices fabricated in accordance with embodiments of the invention may be incorporated into a wide variety of consumer products, including flat panel displays, computer monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The terms halo, halogen, alkyl, cycloalkyl, alkenyl, alkynyl, arylkyl, heterocyclic group, aryl, aromatic group, and heteroaryl are known to the art, and are defined in U.S. Pat. No. 7,279,704 at cols. 31-32, which are incorporated herein by reference.

Novel organometallic 2-phenylquinoline Ir complexes are provided. In particular, the compounds comprise an alkyl having at least 2 carbon atoms. It is believed that compounds containing a bulky alkyl at the 5-position on the phenylquinoline is novel. In addition, it is believed that the presence of a bulky alkyl at the 5-position may increase efficiency by preventing self-quenching. Notably, placing the bulky alkyl at the 5-position on the 2-phenylquinoline does not shift the emission wavelength or change the color. Therefore, these compounds may provide improved efficiency and maintain saturated red emission. These compounds may be useful in organic light emitting devices, in particular as red emitters in the emissive layer of such devices.

Compounds comprising a 5-substituted 2-phenylquinoline containing ligand are provided. The compounds comprise a ligand L having the formula:

Formula I

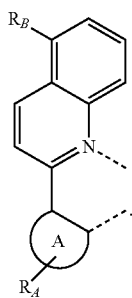

A is a 5-membered or 6-membered carbocyclic or heterocyclic ring. Preferably, A is phenyl. $R_A$ may represent mono, di, tri, or tetra substitutions. Each of $R_A$ is independently selected from the group consisting of hydrogen, deuterium, alkyl, silyl, alkoxy, amino, alkenyl, alkynyl, arylkyl, aryl and heteroaryl. These compounds may be fully or partially deuterated. $R_B$ is selected from the group consisting of alkyl having at least 2 carbon atoms, amino, alkenyl, alkynyl, arylkyl, and silyl. The ligand L is coordinated to a metal M having an atomic number greater than 40. Preferably, M is Ir.

In one aspect, the compound has the formula:

Formula II

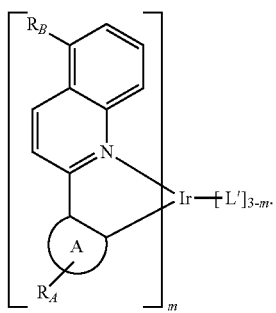

L' is an ancillary ligand. m is 1, 2, or 3.

In another aspect, L' is a monoanionic bidentate ligand. In yet another aspect, L' is

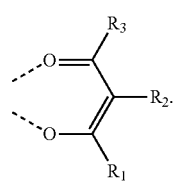

$R_1$, $R_2$, and $R_3$ are independently selected from the group consisting of hydrogen, deuterium, alkyl, alkoxy, amino, alkenyl, alkynyl, arylkyl, aryl and heteroaryl.

In one aspect, the compound has the formula:

Formula III

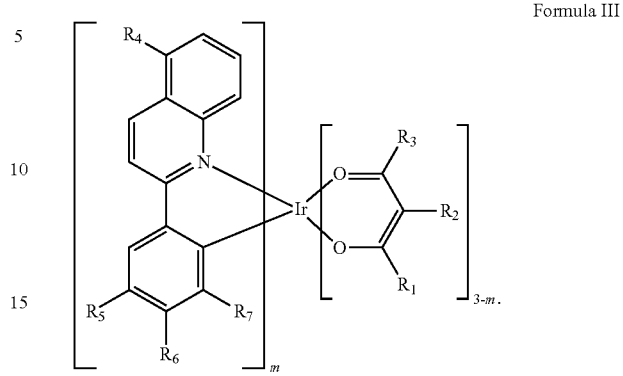

$R_1$, $R_2$, $R_3$, $R_5$, $R_6$ and $R_7$ are independently selected from the group consisting of hydrogen, deuterium, alkyl, silyl, alkoxy, amino, alkenyl, alkynyl, arylkyl, aryl and heteroaryl. $R_4$ is selected from the group consisting of alkyl having at least 2 carbon atoms, amino, alkenyl, alkynyl, arylkyl, and silyl. m is 1, 2, or 3.

Preferably, each of $R_1$ and $R_3$ are a branched alkyl with branching at a position further than the α position to the carbonyl group. Without being bound by theory, it is believed that a branched alkyl substituent at $R_1$ and $R_3$ may provide high device efficiency and stability, and a very narrow emission spectrum.

The placement of substituents on the compound having Formula III may improve efficiency while maintaining a desirable spectrum. In particular, it is believed that substitution on the position ortho to the $R_5$ next to quinoline with a substituent other than hydrogen, as shown in Formula III, may result in broadening the compound's spectrum. In addition, alkyl substitution on quinoline at the 3-position may broaden the emission spectrum. Alkyl substitution at the 4, 6, or 7-position may slightly blue shift the emission spectrum, thereby making the emission less saturated. Therefore, the substitution pattern of the 5-substituted 2-phenylquinoline compounds described herein may provide highly desirable compound and device characteristics.

In one aspect, each of $R_5$, $R_6$ and $R_7$ are independently selected from methyl and hydrogen, and at least one of $R_5$, $R_6$ and $R_7$ is methyl. In another aspect, each of $R_5$ and $R_7$ are methyl, and $R_6$ is hydrogen. In yet another aspect, each of $R_5$ and $R_6$ are methyl, and $R_7$ is hydrogen. In a further aspect, each of $R_5$, $R_6$ and $R_7$ are methyl.

In one aspect, $R_4$ is an alkyl group having at least 4 carbon atoms. In another aspect, $R_4$ is an alkyl group having at least 3 carbon atoms.

Alkyl substitutions may be particularly important because they offer a wide range of tunability in terms of evaporation temperature, solubility, energy levels, device efficiency and narrowness of the emission spectrum. Additionally, alkyl groups can be stable functional groups chemically and in device operation.

Specific, non-limiting examples of the 5-substituted 2-phenylquinoline containing compounds are provided. In one aspect, the compound is selected from the group consisting of:

Compound 1
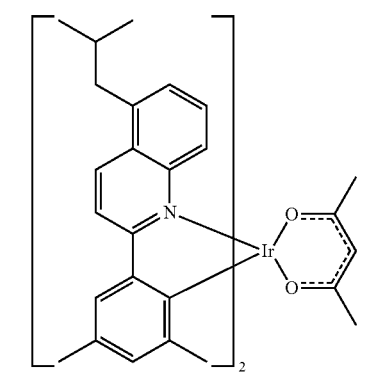
Compound 2
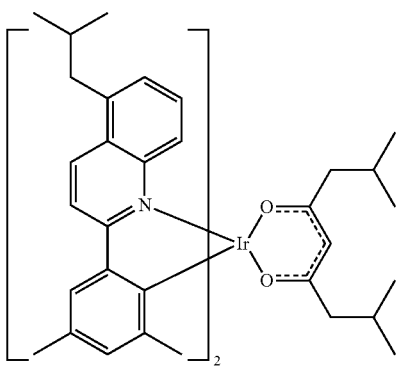
Compound 3
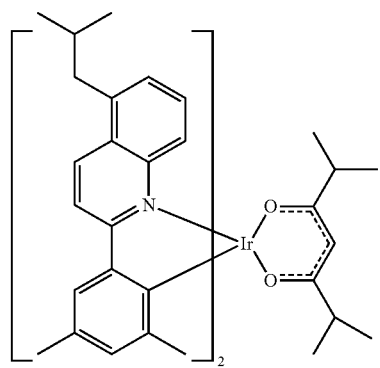
Compound 4
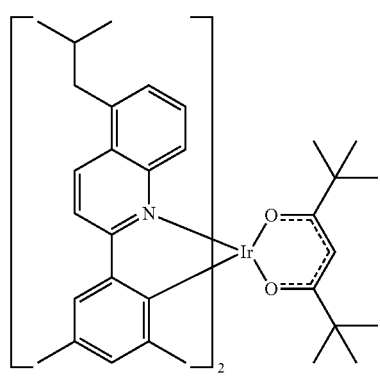
Compound 5
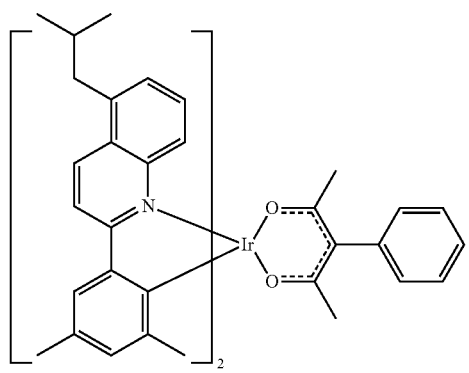
Compound 6
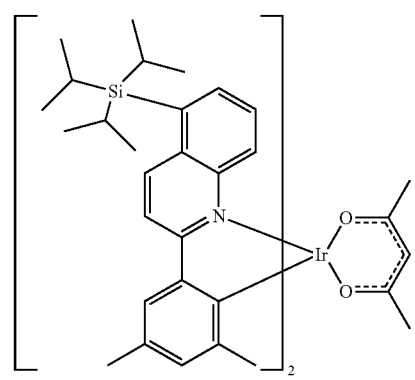
Compound 7
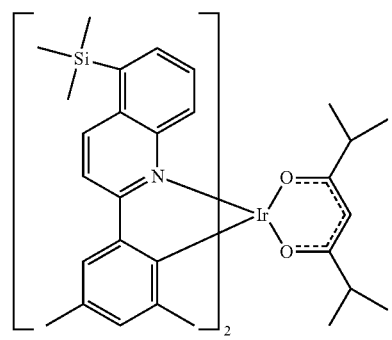
Compound 8
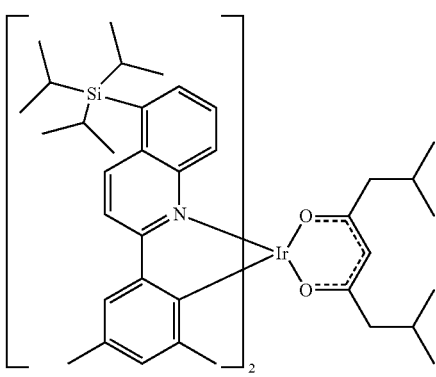

Compound 9
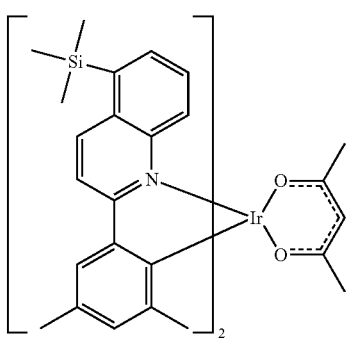
Compound 10
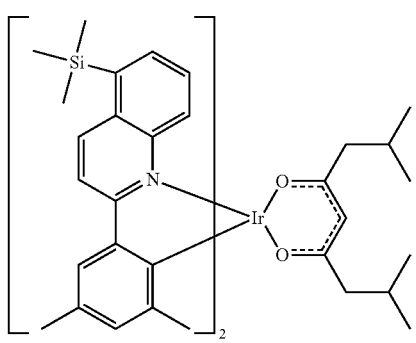
Compound 11
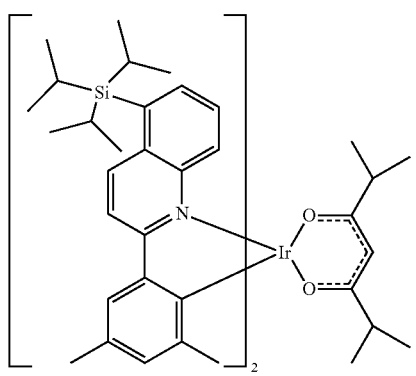
Compound 12
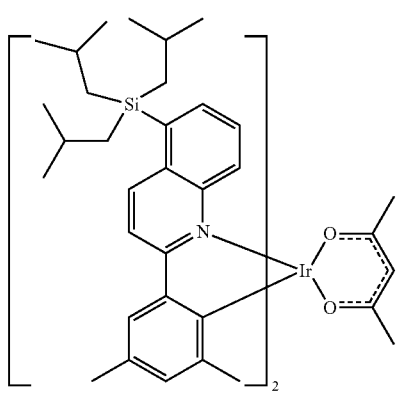
Compound 13
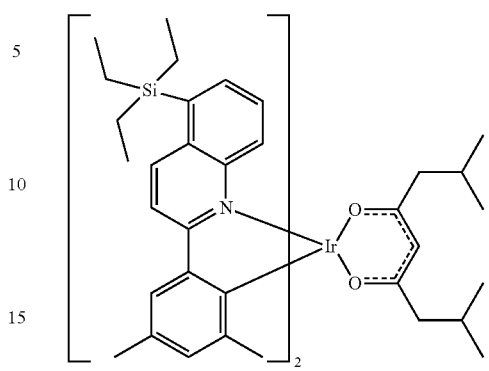
Compound 14
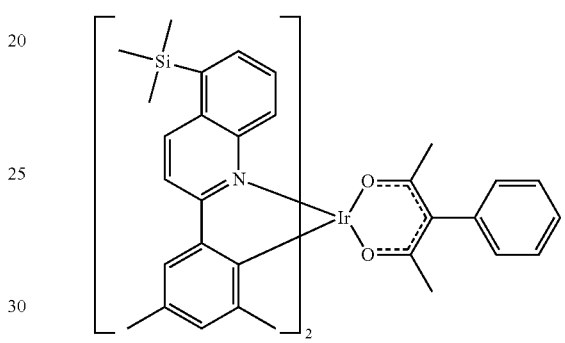
Compound 15
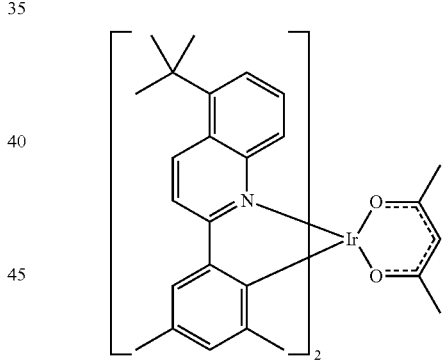
Compound 16
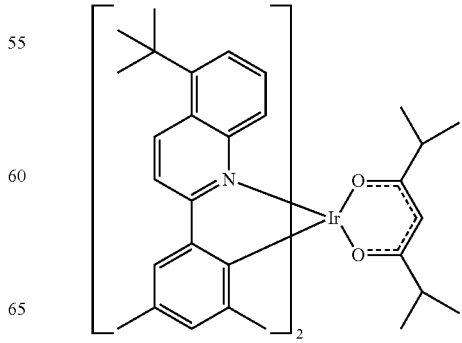

Compound 17
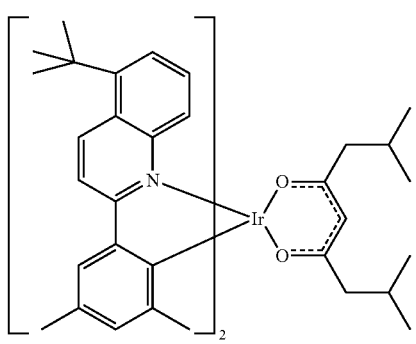
Compound 18
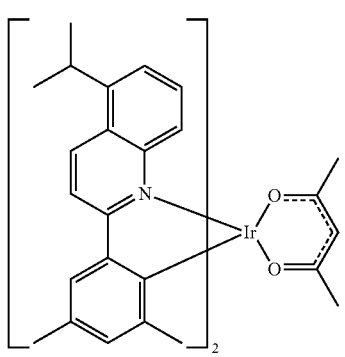
Compound 19
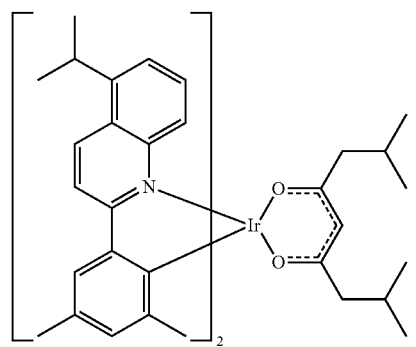
Compound 20
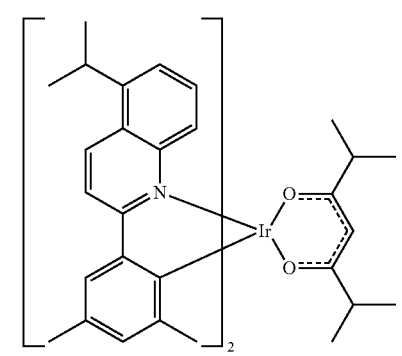
Compound 21
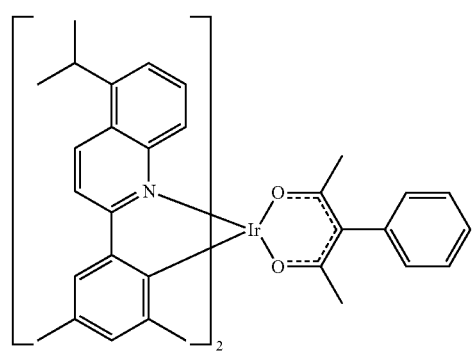
Compound 22
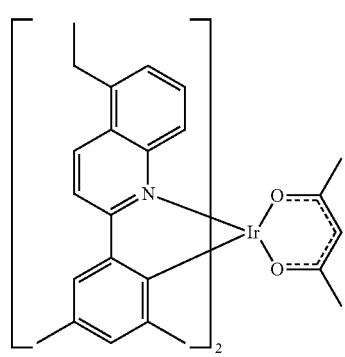
Compound 23
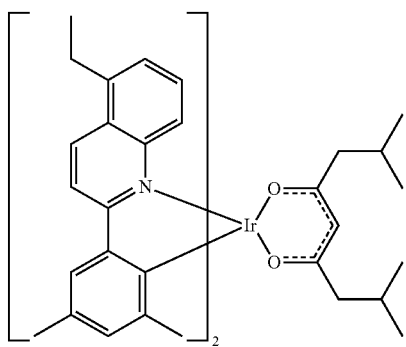
Compound 24
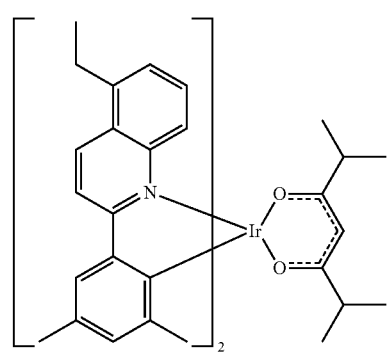

Compound 25
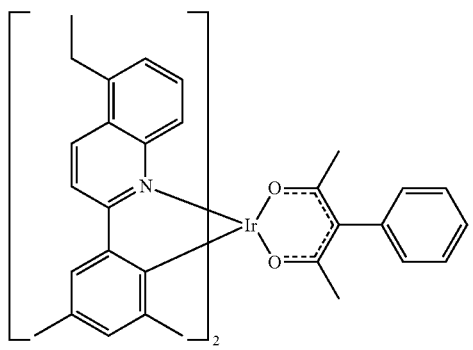
Compound 29
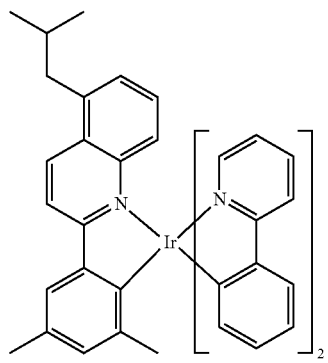
Compound 26
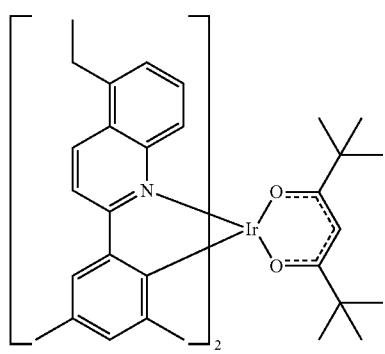
Compound 30
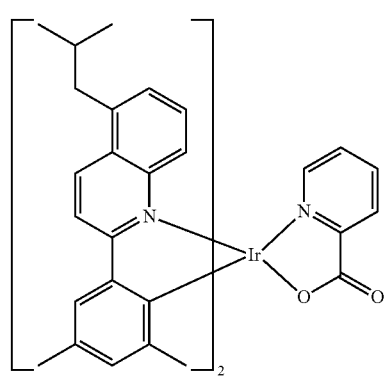
Compound 27
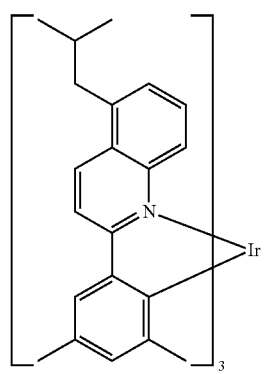
Compound 31
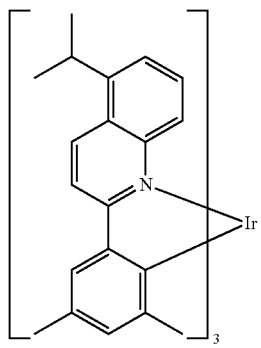
Compound 28
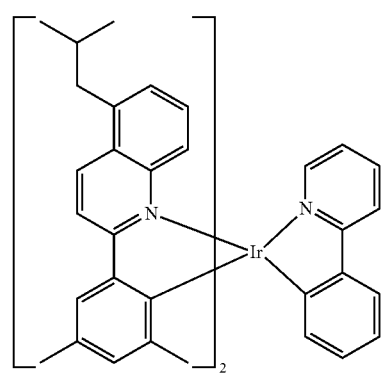
Compound 32
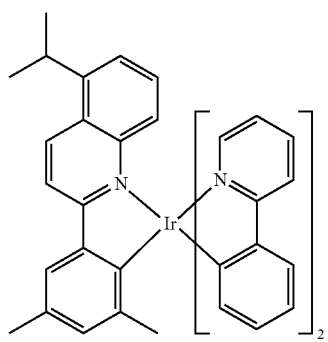

-continued
Compound 33
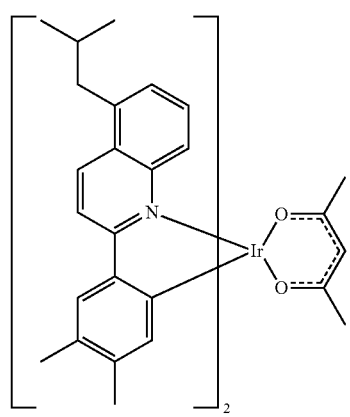
Compound 37
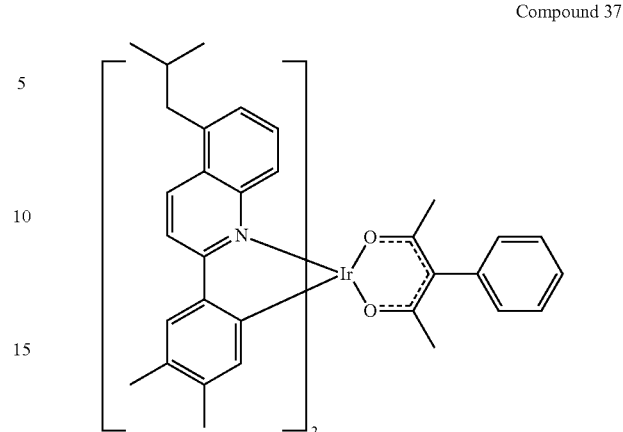
Compound 34
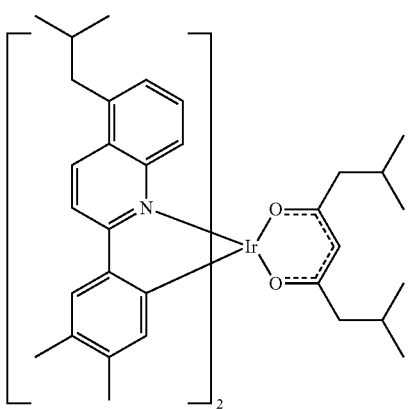
Compound 38
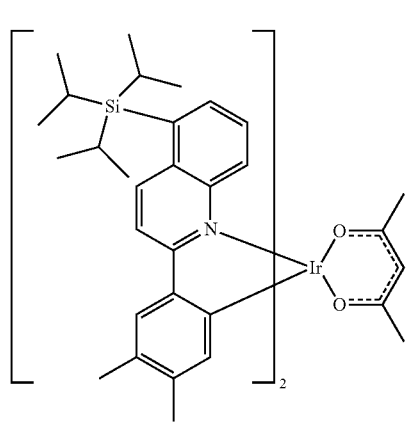
Compound 35
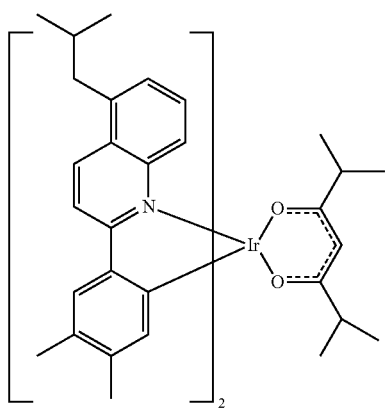
Compound 39
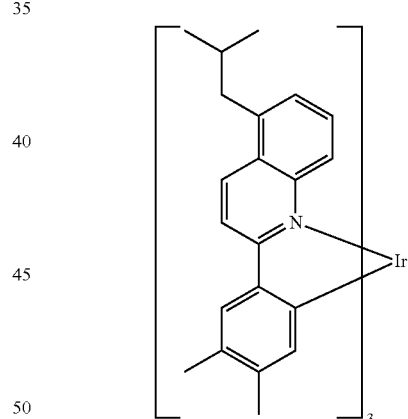
Compound 36
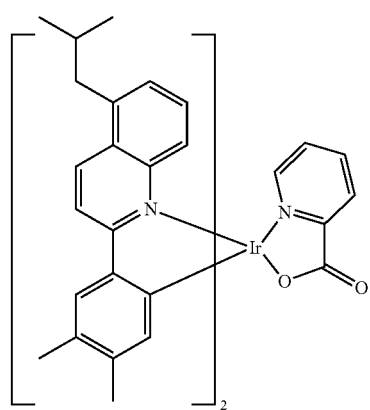
Compound 40
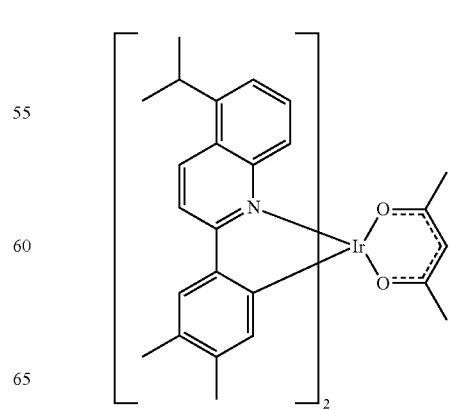

Compound 41
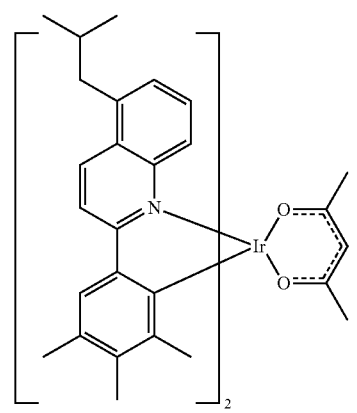
Compound 42
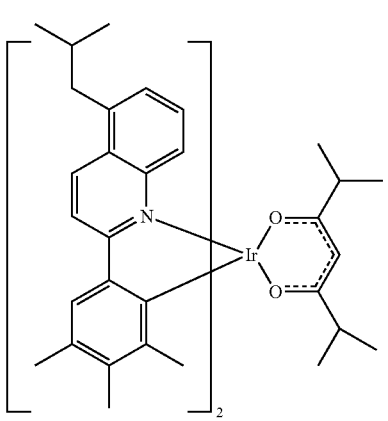
Compound 43
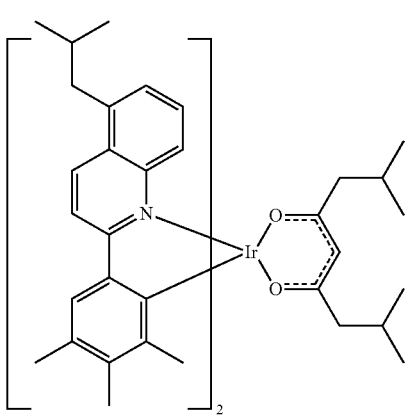
Compound 44
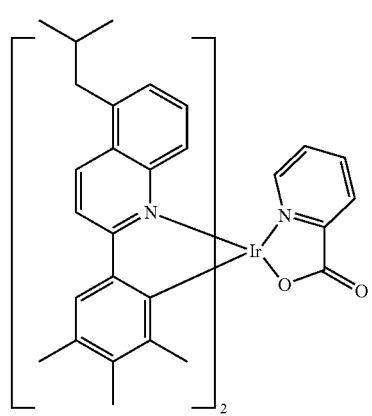
Compound 45
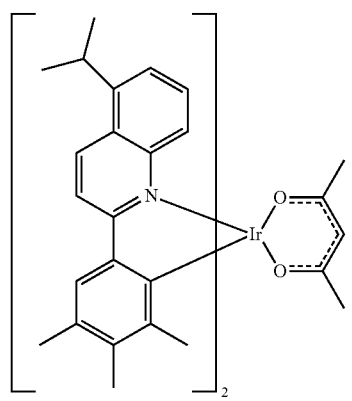
Compound 46
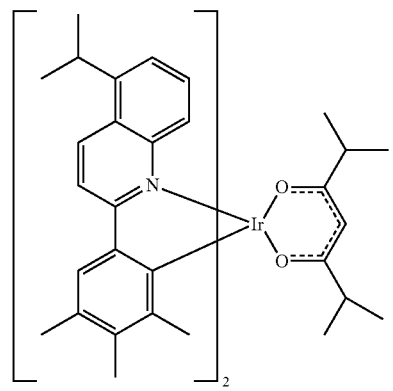
Compound 47
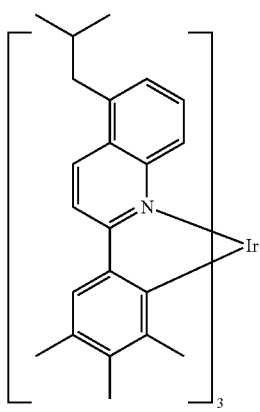
Compound 48
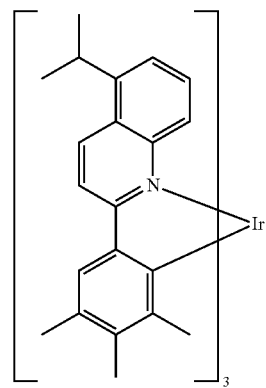

Compound 49

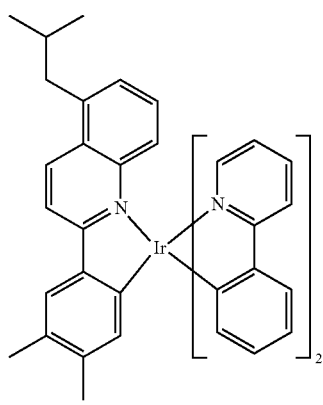

Compound II-2

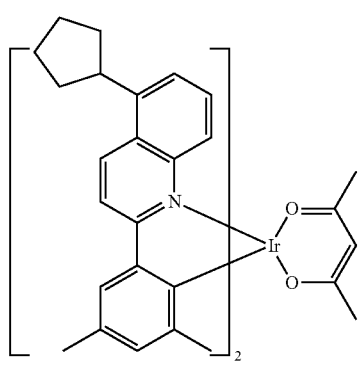

Compound 50

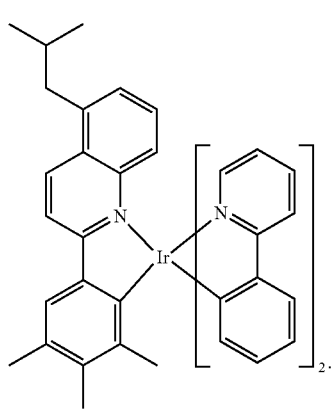

Compound II-3

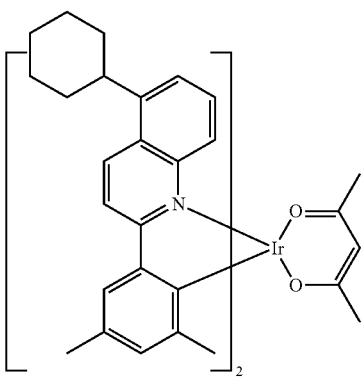

In another aspect, $R_4$ in compound having Formula III comprises a cycloalkyl group having at least 4 carbon atoms. The inventors have discovered that provision of cycloalkyl substituent at 5-position of the 2-phenylquinoline provides further improvement in the phosphorescent characteristics of the compound over linear or branched alkyl group substituents. This improved compound is suitable as red emitters in Phosphorescent OLEDs. Specific, non-limiting examples of the 5-substituted 2-phenylquinoline containing compound having Formula III wherein $R_4$ comprises a cycloalkyl group having at least 4 carbon atoms is selected from the group consisting of Compound II-1-Compound II-72 shown below.

Compound II-4

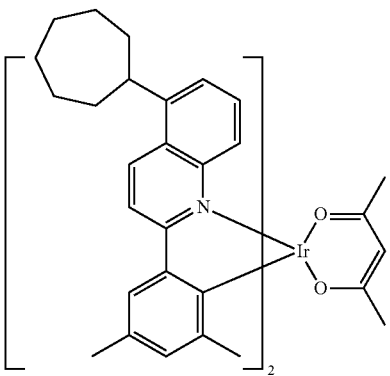

Compound II-1

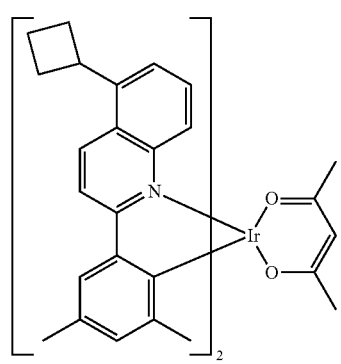

Compound II-5

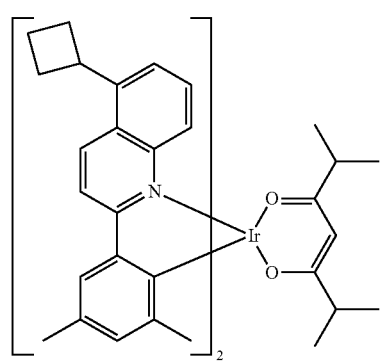

Compound II-6
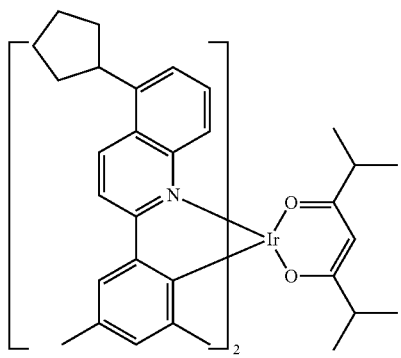
Compound II-7
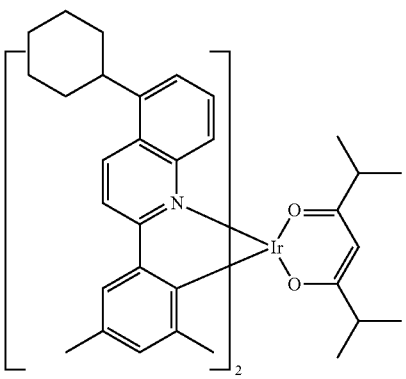
Compound II-8
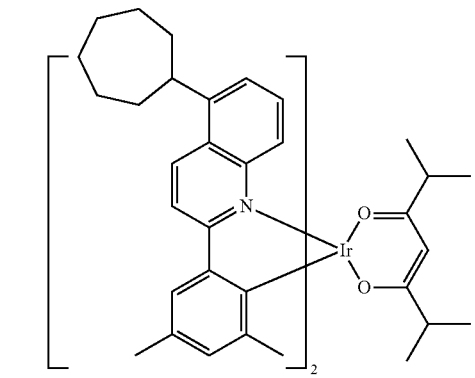
Compound II-9
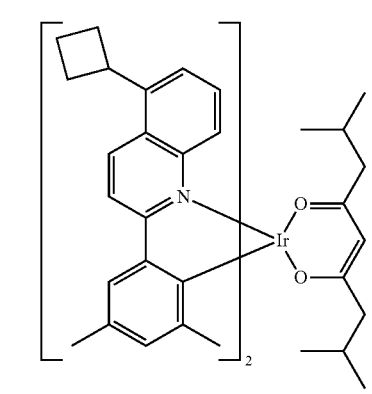
Compound II-10
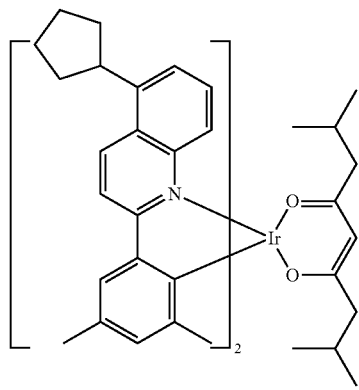
Compound II-11
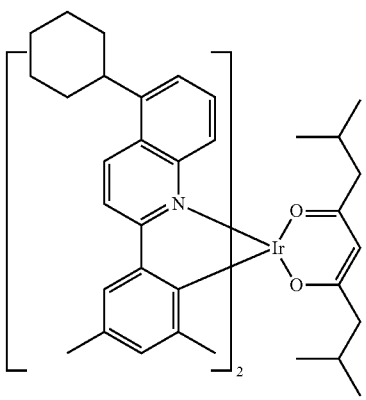
Compound II-12
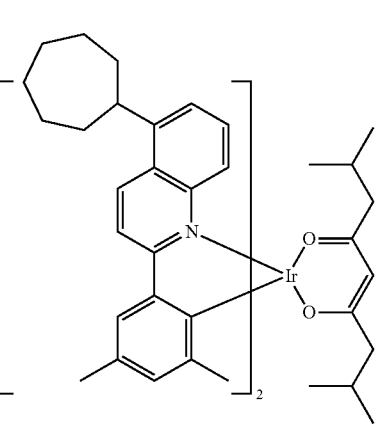
Compound II-13
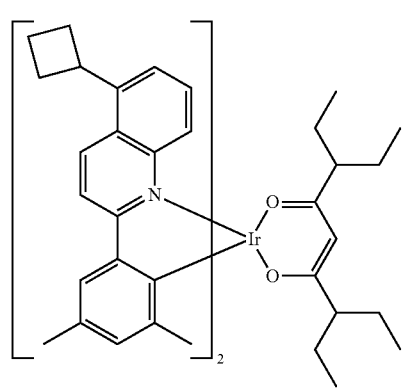

Compound II-14
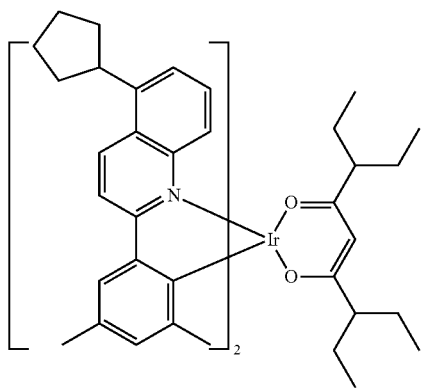
Compound II-15
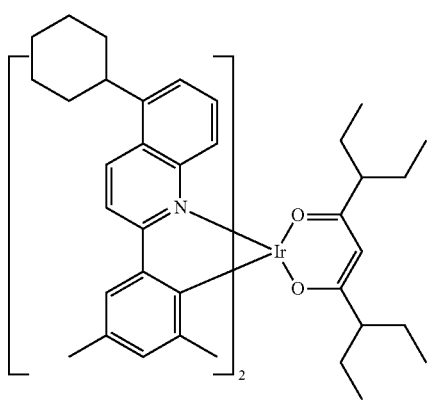
Compound II-16
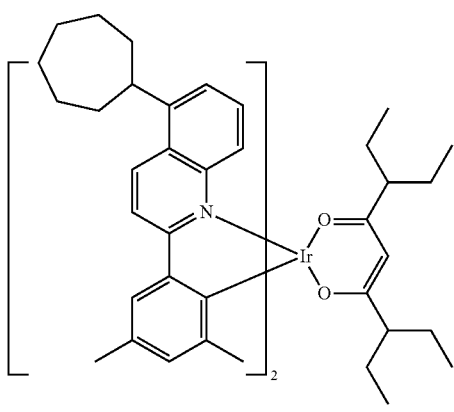
Compound II-17
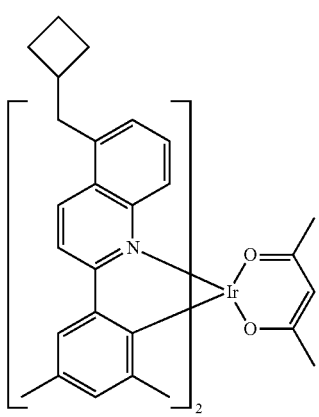
Compound II-18
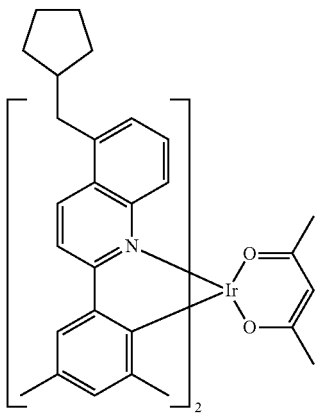
Compound II-19
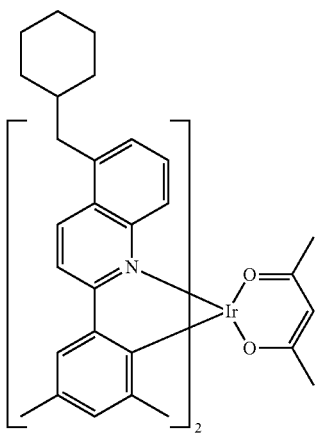
Compound II-20

Compound II-21
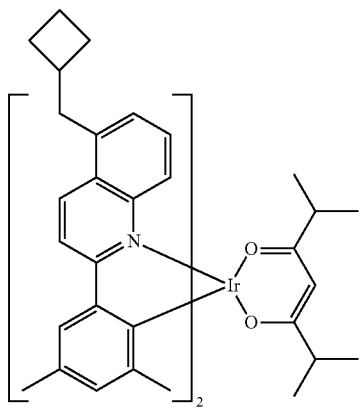
Compound II-22
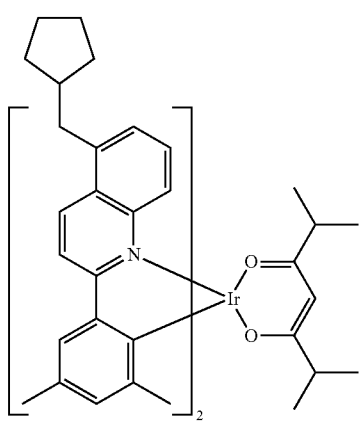
Compound II-23
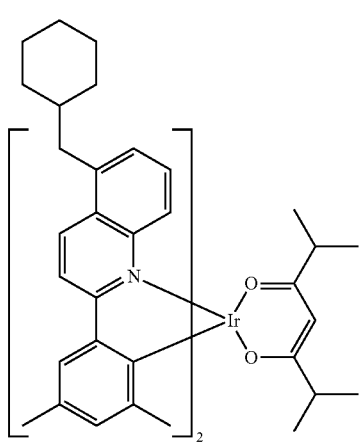
Compound II-24
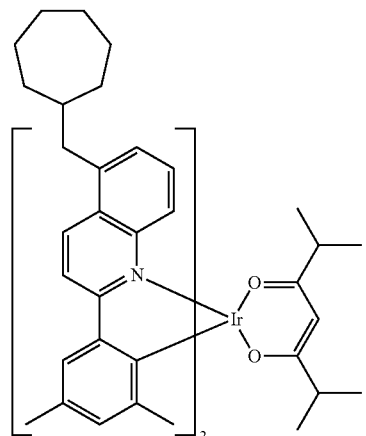
Compound II-25
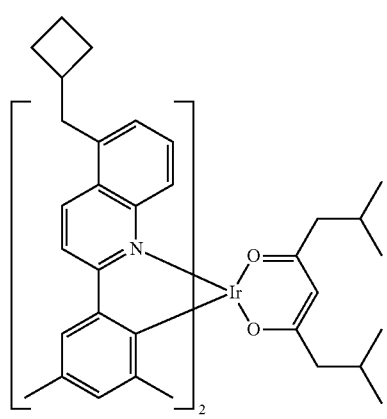
Compound II-26
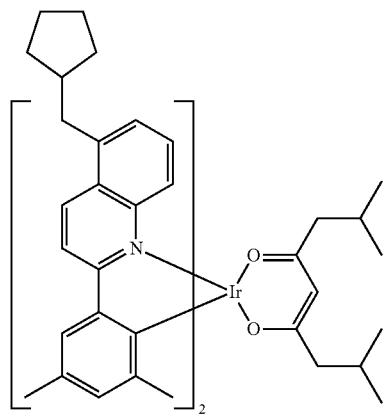

Compound II-27
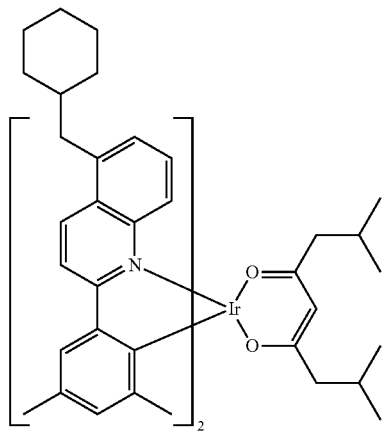
Compound II-30
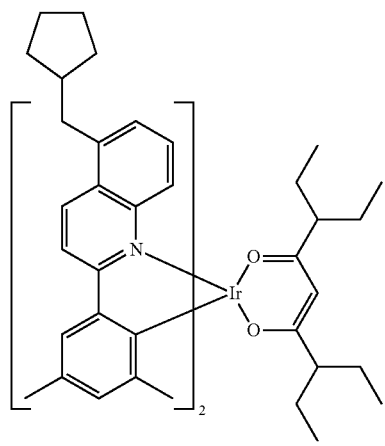
Compound II-28
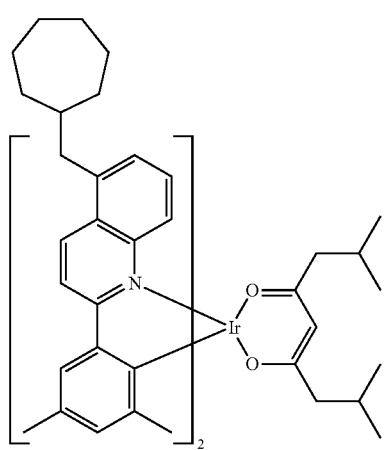
Compound II-31
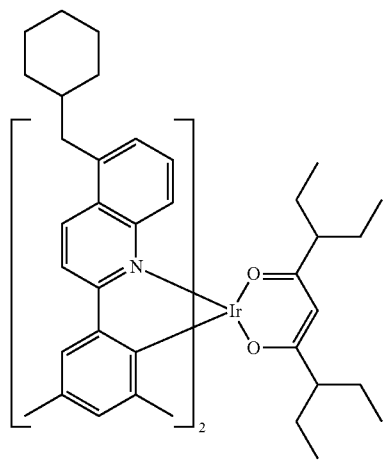
Compound II-29
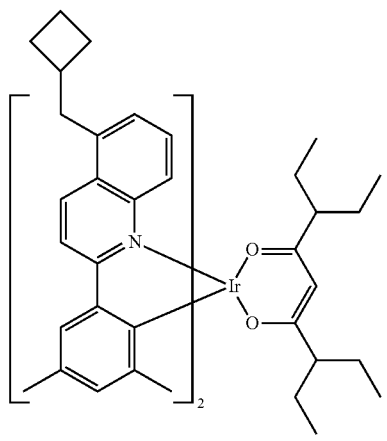
Compound II-32
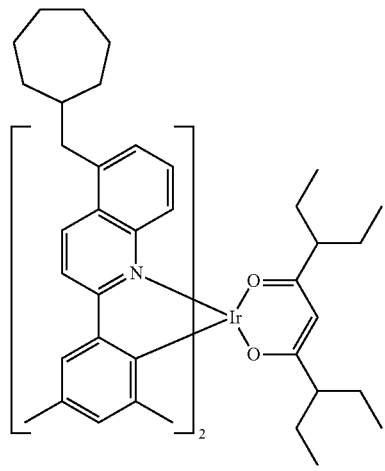

Compound II-33
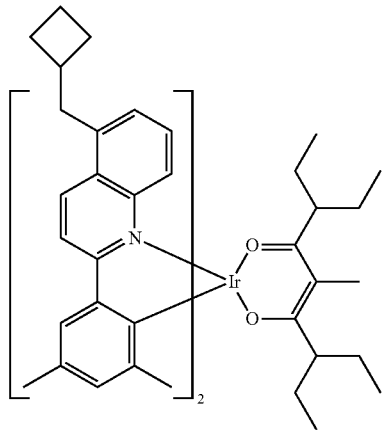
Compound II-34
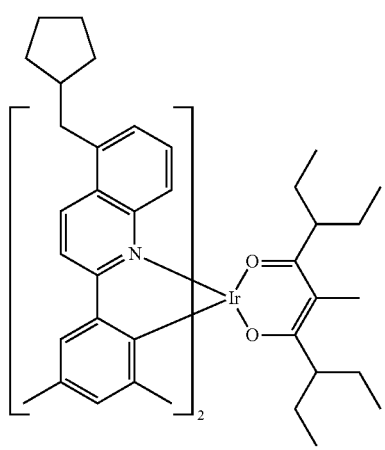
Compound II-35
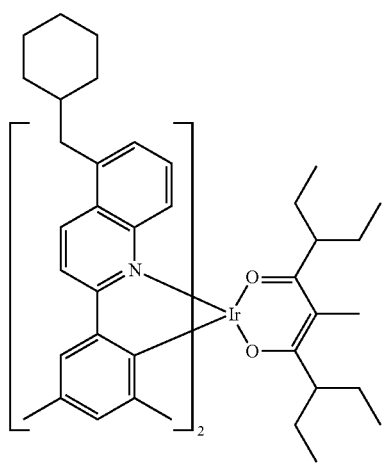
Compound II-36
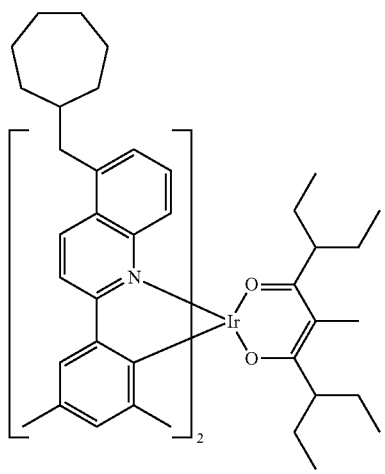
Compound II-37
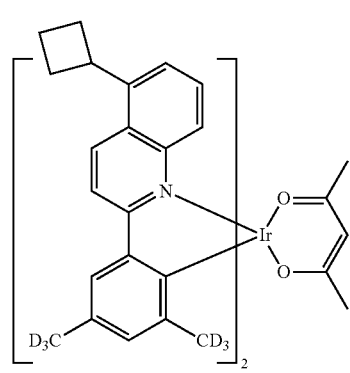
Compound II-38
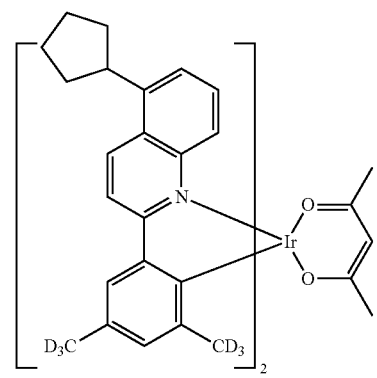
Compound II-39
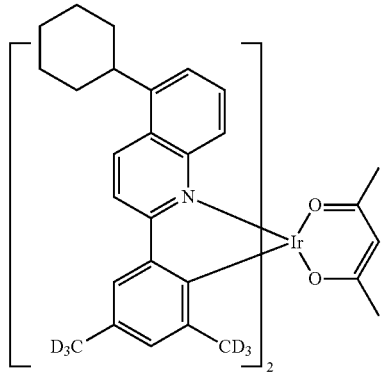

Compound II-40
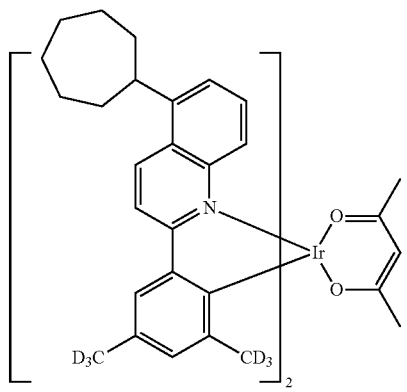
Compound II-41
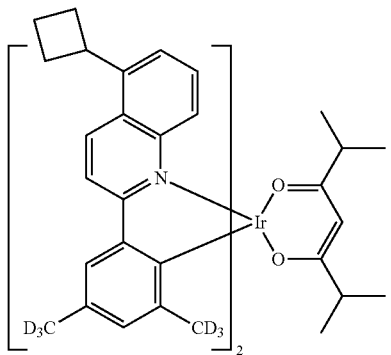
Compound II-42
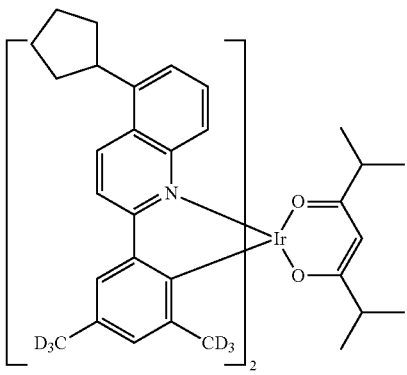
Compound II-43
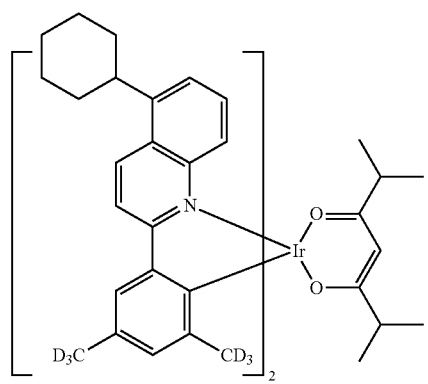
Compound II-44
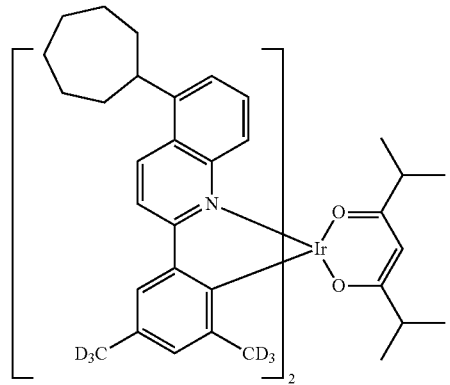
Compound II-45
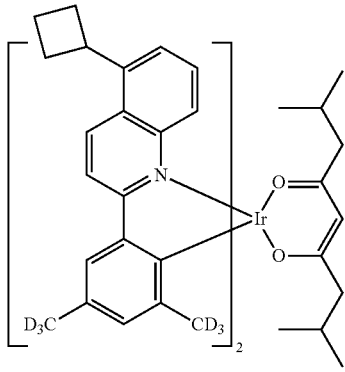
Compound II-46
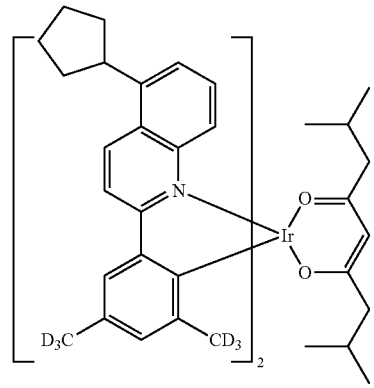
Compound II-47
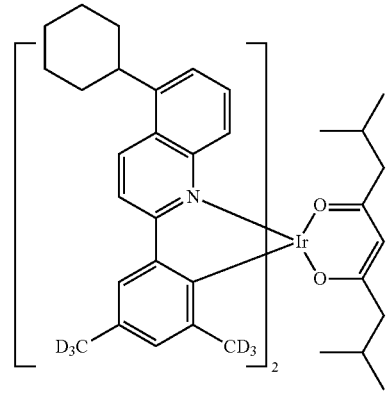

-continued
Compound II-48
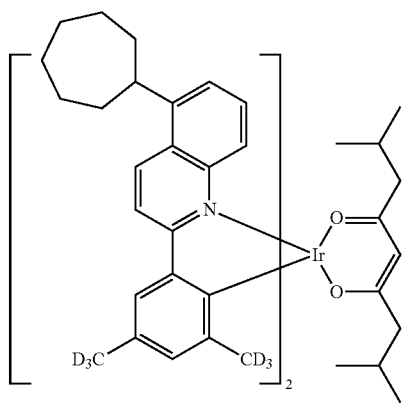
Compound II-49
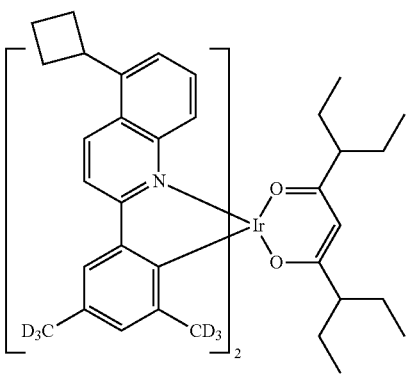
Compound II-50
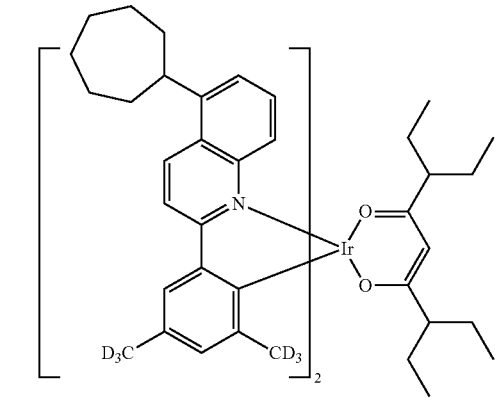
Compound II-51
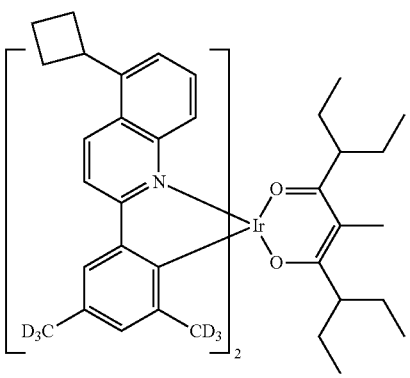
-continued
Compound II-52
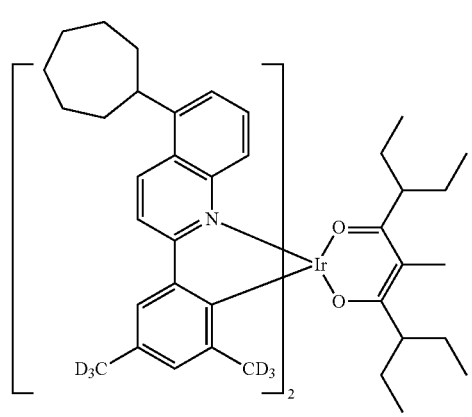
Compound II-53
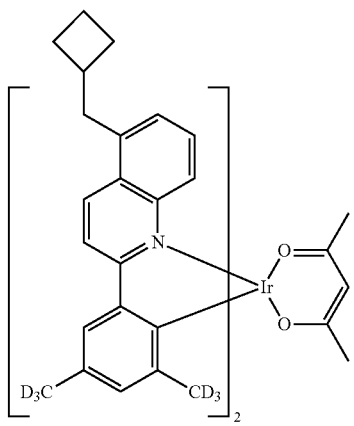
Compound II-54
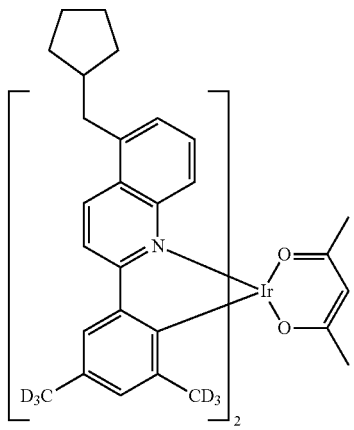

Compound II-55
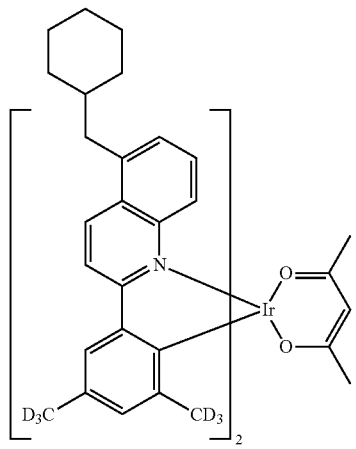
Compound II-56
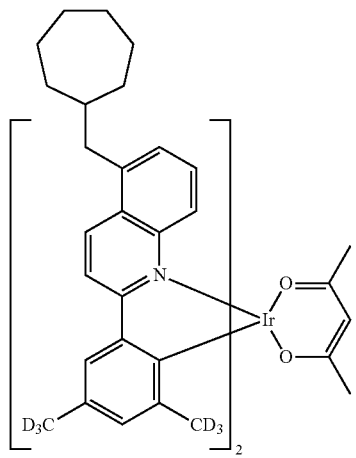
Compound II-57
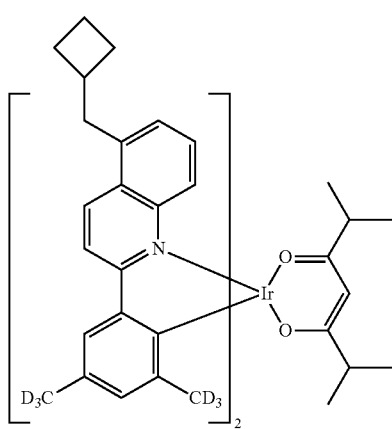
Compound II-58
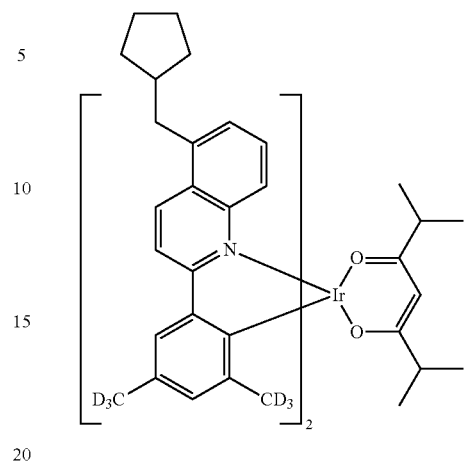
Compound II-59
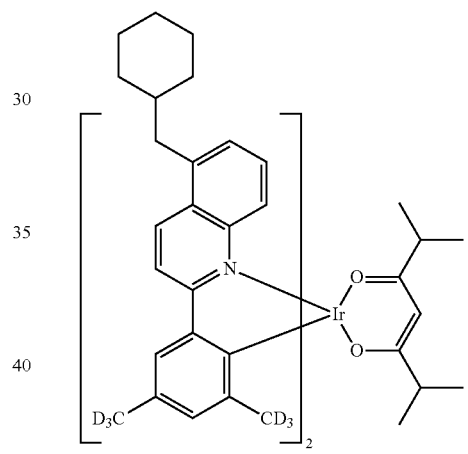
Compound II-60
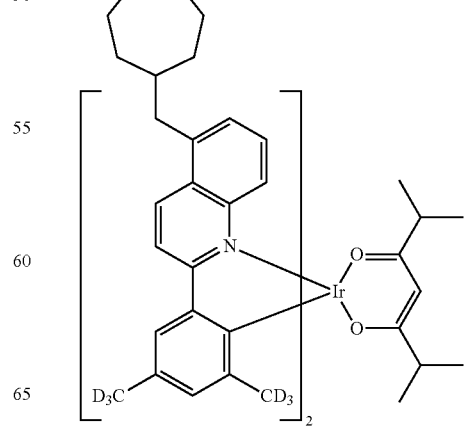

Compound II-61
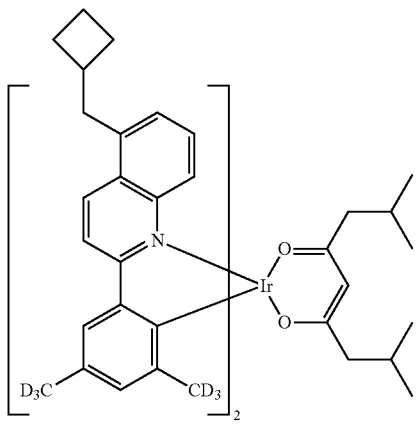
Compound II-62
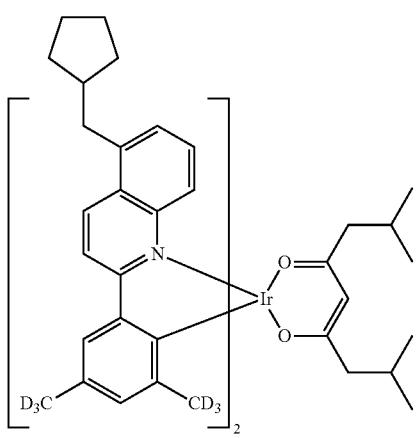
Compound II-63
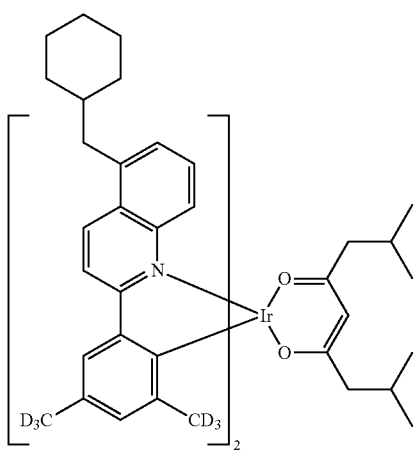
Compound II-64
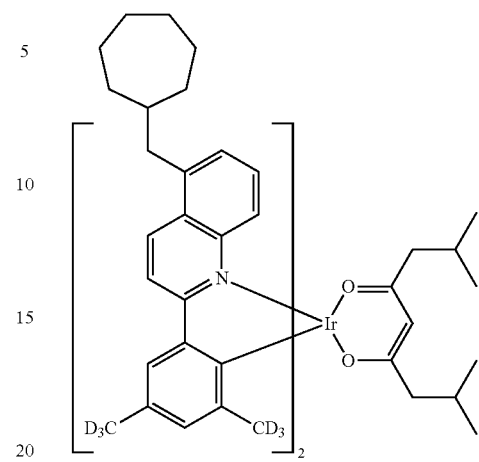
Compound II-65
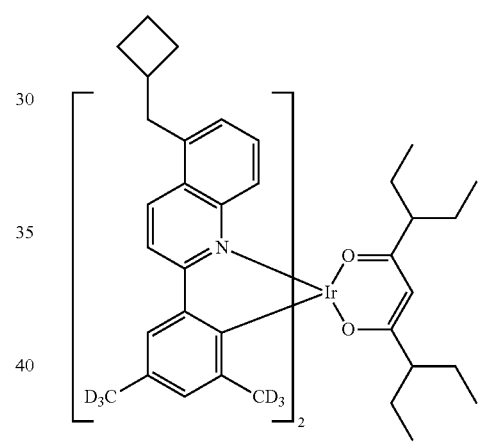
Compound II-66
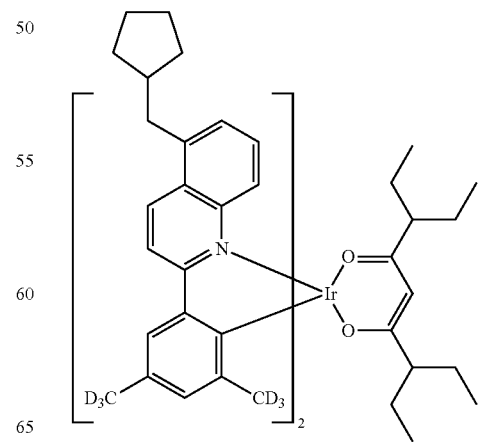

Compound II-67

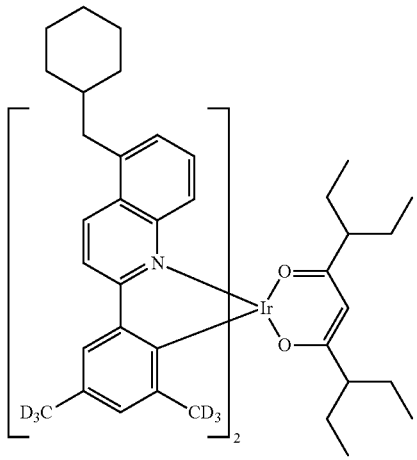

Compound II-68

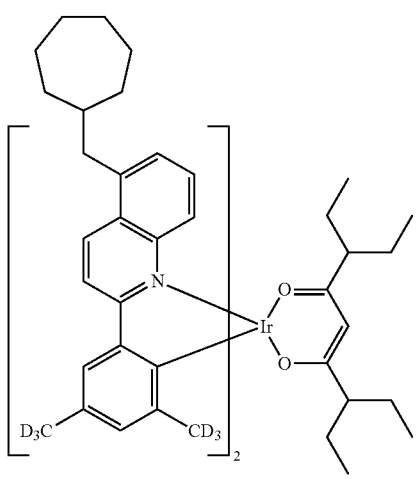

Compound II-69

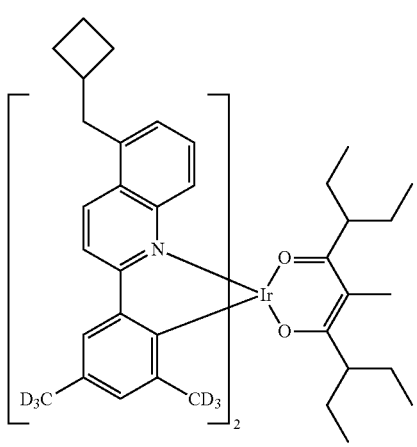

Compound II-70

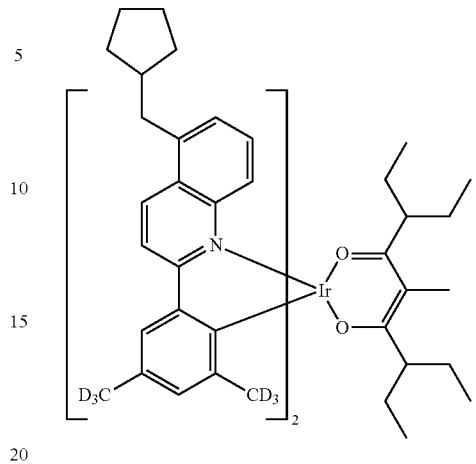

Compound II-71

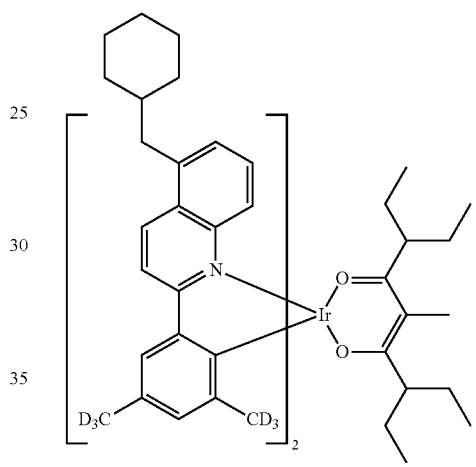

Compound II-72

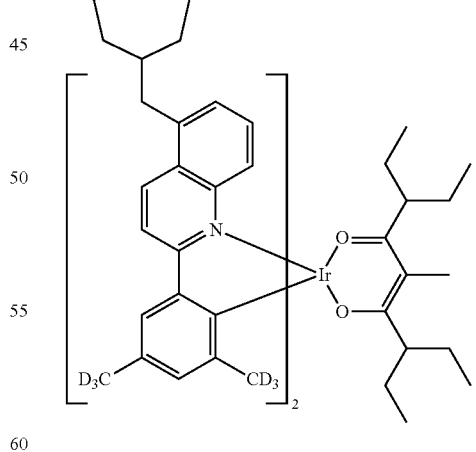

Additionally, a first device comprising an organic light emitting device is provided. The organic light emitting device further comprises an anode, a cathode, and an organic layer, disposed between the anode and the cathode. The organic layer comprises a compound comprising a ligand L having the formula:

Formula I

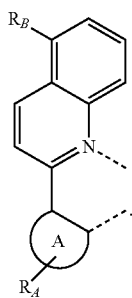

A is a 5-membered or 6-membered carbocyclic or heterocyclic ring. Preferably, A is phenyl. $R_A$ may represent mono, di, tri, or tetra substitutions. Each of $R_A$ is independently selected from the group consisting of hydrogen, deuterium, alkyl, silyl, alkoxy, amino, alkenyl, alkynyl, arylkyl, aryl and heteroaryl. $R_B$ is selected from the group consisting of alkyl having at least 2 carbon atoms, amino, alkenyl, alkynyl, arylkyl, and silyl. The ligand L is coordinated to a metal M having an atomic number greater than 40. Preferably, M is Ir.

In one aspect, the compound has the formula:

Formula II

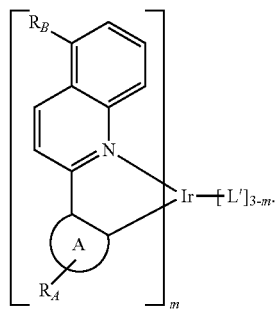

L' is an ancillary ligand. m is 1, 2, or 3.

In one aspect, L' is a monoanionic bidentate ligand. In another aspect, L' is

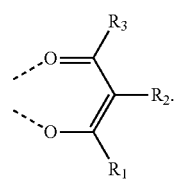

$R_1$, $R_2$, and $R_3$ are independently selected from the group consisting of hydrogen, deuterium, alkyl, alkoxy, amino, alkenyl, alkynyl, arylkyl, aryl and heteroaryl.

In one aspect, the compound has the formula:

Formula III

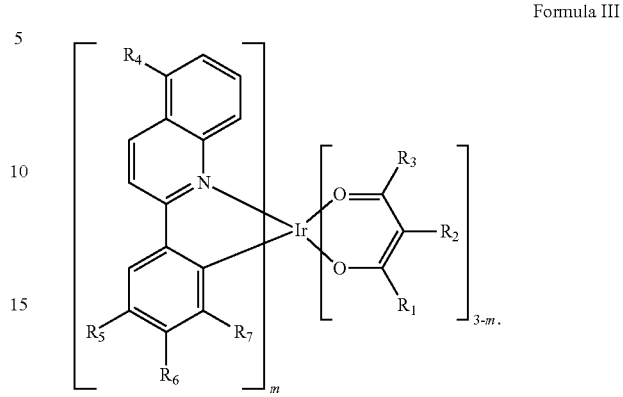

$R_1$, $R_2$, $R_3$, $R_5$, $R_6$ and $R_7$ are independently selected from the group consisting of hydrogen, deuterium, alkyl, silyl, alkoxy, amino, alkenyl, alkynyl, arylkyl, aryl and heteroaryl.

$R_4$ is selected from the group consisting of alkyl having at least 2 carbon atoms, amino, alkenyl, alkynyl, arylkyl, and silyl. m is 1, 2, or 3.

Specific, non-limiting examples of devices comprising the compounds are provided. In one aspect, the first device comprises a compound selected from the group consisting of Compound 1-Compound 50.

In another aspect, the organic layer comprises a compound having Formula III wherein $R_4$ is a cycloalkyl group having at least 4 carbon atoms. Specific, non-limiting examples of the compound having Formula III wherein $R_4$ is a cycloalkyl group having at least 4 carbon atoms is selected from the group consisting of Compound II-1-Compound II-72 disclosed herein.

In one aspect, the organic layer is an emissive layer and the compound is an emissive dopant. In another aspect, the organic layer further comprises a host. In yet another aspect, the host is a metal 8-hydroxyquinolate. Preferably, the host is:

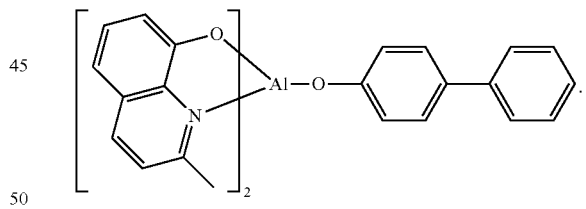

In one aspect, the first device is a consumer product. In another aspect, the first device is an organic light emitting device.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

HIL/HTL:

A hole injecting/transporting material to be used in embodiments of the present invention is not particularly limited, and any compound may be used as long as the compound is typically used as a hole injecting/transporting material. Examples of the material include, but are not limited to: a phthalocyanine or porphryin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and silane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compounds.

Examples of aromatic amine derivatives used in the HIL or HTL include, but are not limited to, the following general structures:

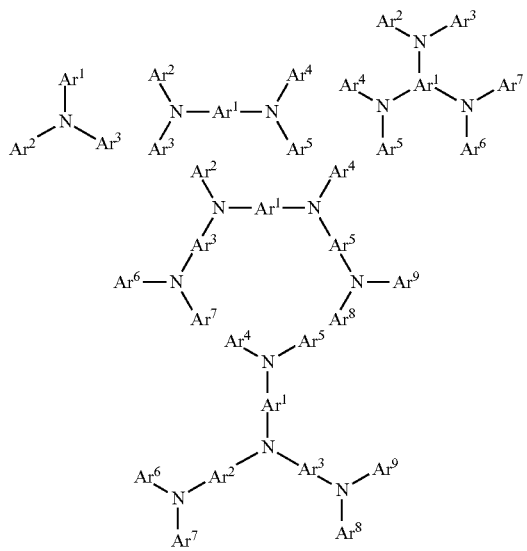

Each of $Ar^1$ to $Ar^9$ is selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each Ar is further substituted by a substituent selected from the group consisting of hydrogen, deuterium, alkyl, alkoxy, amino, alkenyl, alkynyl, arylalkyl, heteroalkyl, aryl and heteroaryl.

In one aspect, $Ar^1$ to $Ar^9$ is independently selected from the group consisting of:

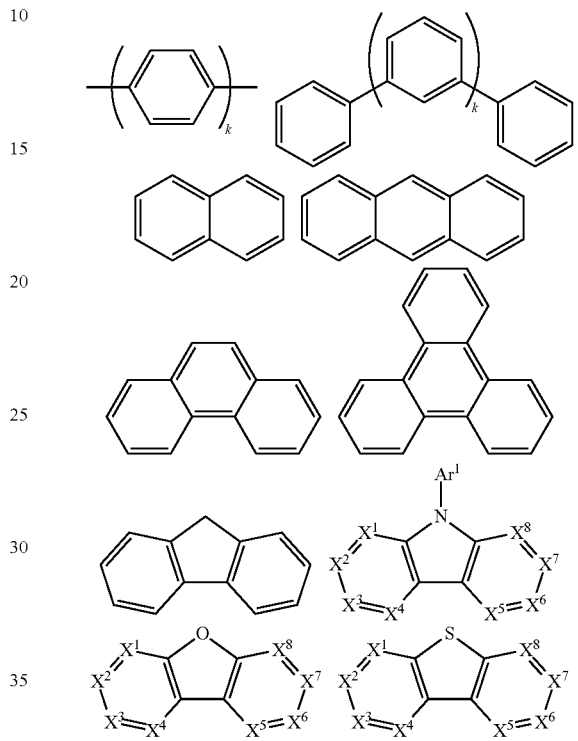

k is an integer from 1 to 20; $X^1$ to $X^8$ is CH or N; $Ar^1$ has the same group defined above.

Examples of metal complexes used in the HIL or HTL include, but are not limited to, the following general formula:

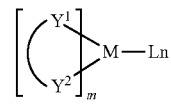

M is a metal, having an atomic weight greater than 40; $(Y^1-Y^2)$ is a bidentate ligand, Y1 and $Y^2$ are independently selected from C, N, O, P, and S; L is an ancillary ligand; m is an integer value from 1 to the maximum number of ligands that may be attached to the metal; and m+n is the maximum number of ligands that may be attached to the metal.

In one aspect, $(Y^1-Y^2)$ is a 2-phenylpyridine derivative.
In another aspect, $(Y^1-Y^2)$ is a carbene ligand.
In another aspect, M is selected from Ir, Pt, Os, and Zn.
In a further aspect, the metal complex has a smallest oxidation potential in solution vs. Fc$^+$/Fc couple less than about 0.6 V.

Host:

The light emitting layer of the organic EL device in some embodiments the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant.

Examples of metal complexes used as hosts are preferred to have the following general formula:

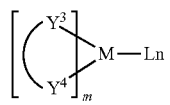

M is a metal; ($Y^3$—$Y^4$) is a bidentate ligand, $Y^3$ and $Y^4$ are independently selected from C, N, O, P, and S; L is an ancillary ligand; m is an integer value from 1 to the maximum number of ligands that may be attached to the metal; and m+n is the maximum number of ligands that may be attached to the metal.

In one aspect, the metal complexes are:

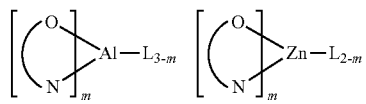

(O—N) is a bidentate ligand, having metal coordinated to atoms O and N.

In another aspect, M is selected from Ir and Pt.

In a further aspect, ($Y^3$—$Y^4$) is a carbene ligand.

Examples of organic compounds used as hosts are selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each group is further substituted by a substituent selected from the group consisting of hydrogen, deuterium, alkyl, alkoxy, amino, alkenyl, alkynyl, arylalkyl, heteroalkyl, aryl and heteroaryl.

In one aspect, the host compound contains at least one of the following groups in the molecule:

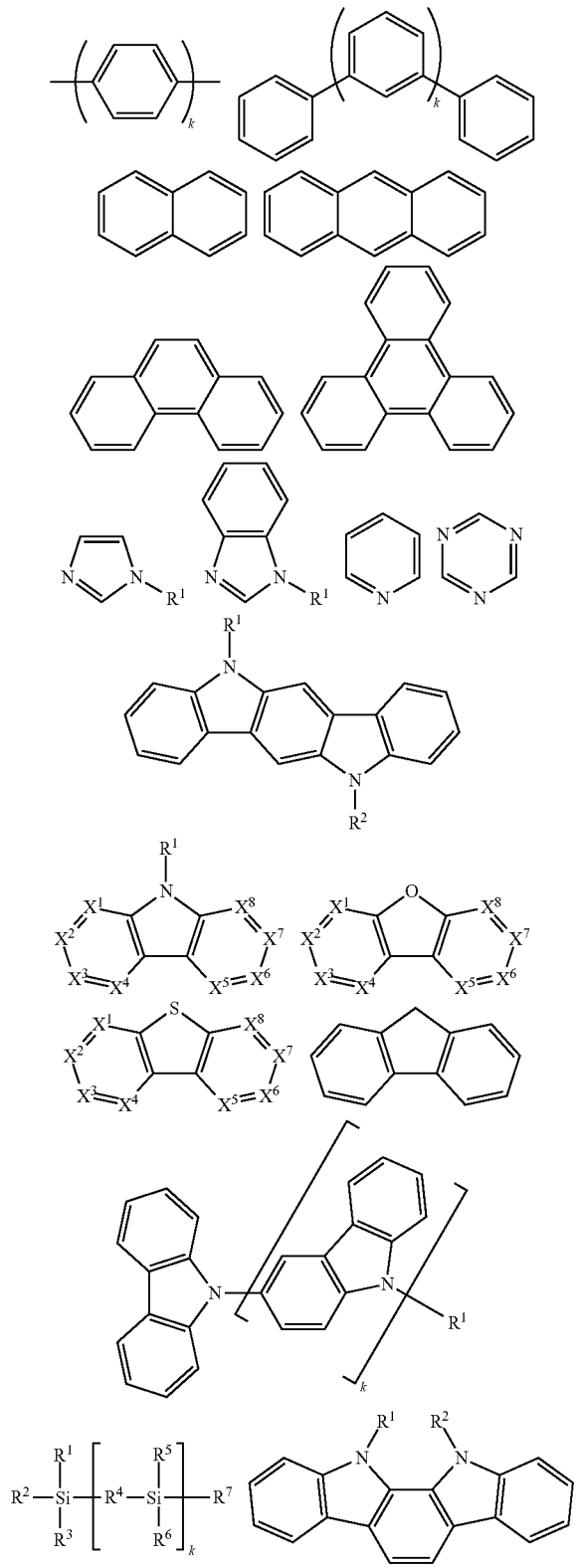

$R^1$ to $R^7$ is independently selected from the group consisting of hydrogen, deuterium, alkyl, alkoxy, amino, alkenyl, alkynyl, arylalkyl, heteroalkyl, aryl and heteroaryl, when it is aryl or heteroaryl, it has the similar definition as Ar's mentioned above.

k is an integer from 0 to 20.

$X^1$ to $X^8$ is selected from CH or N.

HBL:

A hole blocking layer (HBL) may be used to reduce the number of holes and/or excitons that leave the emissive layer. The presence of such a blocking layer in a device may result in substantially higher efficiencies as compared to a similar device lacking a blocking layer. Also, a blocking layer may be used to confine emission to a desired region of an OLED.

In one aspect, the compound used in the HBL contains the same molecule used as host described above.

In another aspect, the compound used in the HBL contains at least one of the following groups in the molecule:

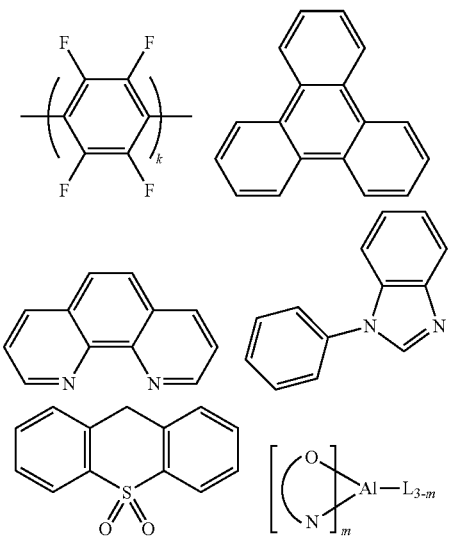

k is an integer from 0 to 20; L is an ancillary ligand, m is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, the compound used in the ETL contains at least one of the following groups in the molecule:

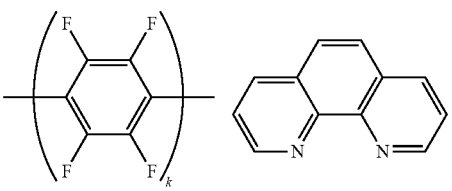

-continued

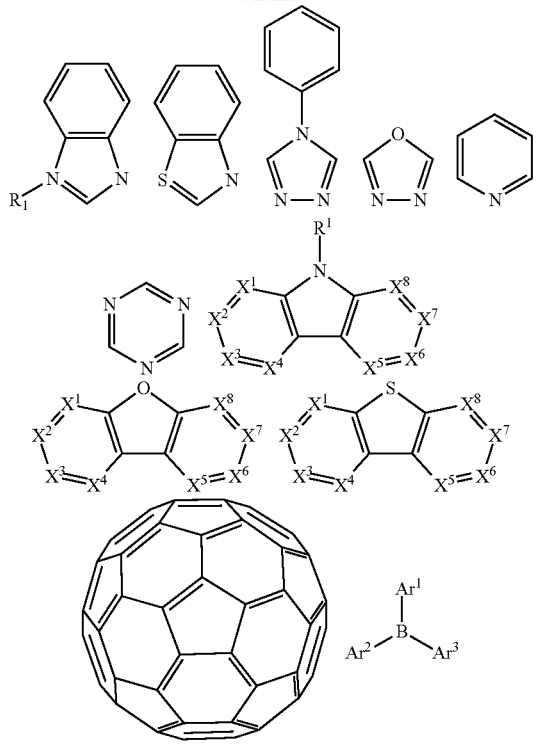

$R^1$ is selected from the group consisting of hydrogen, deuterium, alkyl, alkoxy, amino, alkenyl, alkynyl, arylalkyl, heteroalkyl, aryl and heteroaryl, when it is aryl or heteroaryl, it has the similar definition as Ar's mentioned above.

$Ar^1$ to $Ar^9$ has the similar definition as Ar's mentioned above.

k is an integer from 0 to 20.

$X^1$ to $X^8$ is selected from CH or N.

In another aspect, the metal complexes used in the ETL contain, but are not limited to, the following general formula:

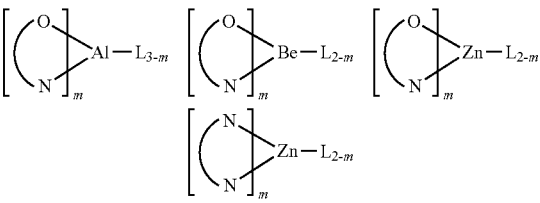

(O—N) or (N—N) is a bidentate ligand, having metal coordinated to atoms O, N or N,N; L is an ancillary ligand; m is an integer value from 1 to the maximum number of ligands that may be attached to the metal.

In any above-mentioned compounds used in each layer of OLED device, the hydrogen atoms can be partially or fully deuterated.

In addition to and/or in combination with the materials disclosed herein, many hole injection materials, hole transporting materials, host materials, dopant materials, exiton/hole blocking layer materials, electron transporting and electron injecting materials may be used in an OLED. Non-limiting examples of the materials that may be used in an OLED in combination with materials disclosed herein are listed in Table 1 below. Table 1 lists non-limiting classes of materials, non-limiting examples of compounds for each class, and references that disclose the materials.

TABLE 1

| MATERIAL | EXAMPLES OF MATERIAL | PUBLICATIONS |
| --- | --- | --- |
| *Hole injection materials* | | |
| Phthalocyanine and porphyrin compounds | | Appl. Phys. Lett. 69, 2160 (1996) |
| Starburst triarylamines | | J. Lumin. 72-74, 985 (1997) |
| $CF_x$ Fluorohydrocarbon polymer | $-[CH_xF_y]_n-$ | Appl. Phys. Lett. 78, 673 (2001) |
| Conducting polymers (e.g., PEDOT:PSS, polyaniline, polythiophene) | | Synth. Met. 87, 171 (1997) WO2007002683 |
| Phosphonic acid and silane SAMs | | US20030162053 |

TABLE 1-continued
| MATERIAL | EXAMPLES OF MATERIAL | PUBLICATIONS |
|---|---|---|
| Triarylamine or polythiophene polymers with conductivity dopants | 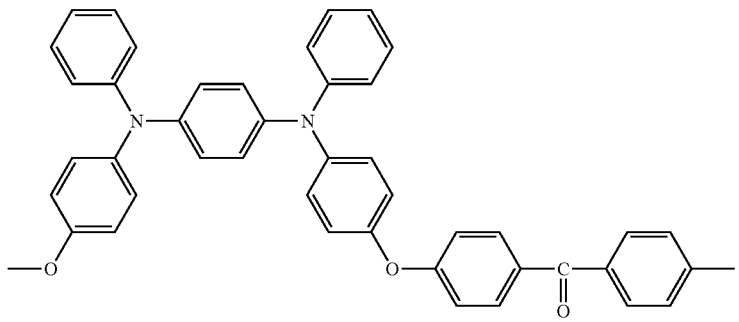 and 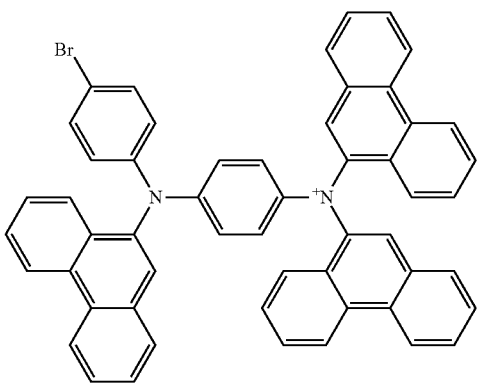 [SMILES: Brc1ccc(N(c2ccc([NH+](c3cc4ccccc4c4ccccc34)c3cc4ccccc4c4ccccc34)cc2)c2cc3ccccc3c3ccccc23)cc1] 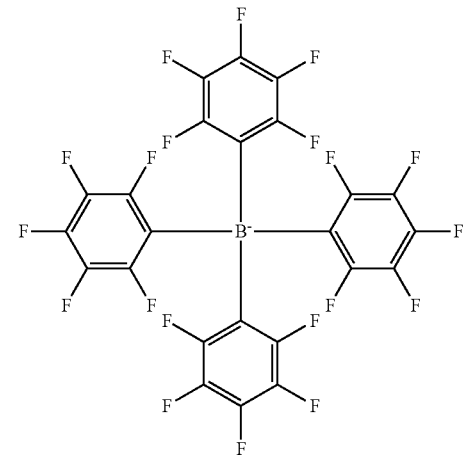 [SMILES: Fc1c(F)c(F)c([B-](c2c(F)c(F)c(F)c(F)c2F)(c2c(F)c(F)c(F)c(F)c2F)c2c(F)c(F)c(F)c(F)c2F)c(F)c1F] | EA01725079A1 |
| Arylamines complexed with metal oxides such as molybdenum and tungsten oxides | 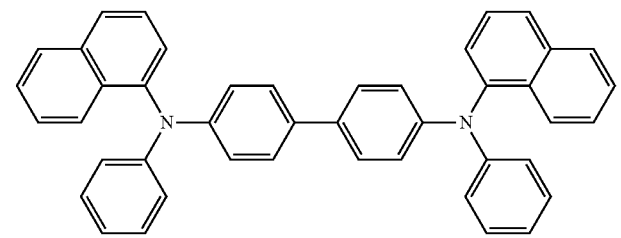 [SMILES: c1ccc(N(c2ccc(-c3ccc(N(c4ccccc4)c4cccc5ccccc45)cc3)cc2)c2cccc3ccccc23)cc1] + $MoO_x$ | SID Symposium Digest, 37, 923 (2006) WO2009018009 |

TABLE 1-continued

| MATERIAL | EXAMPLES OF MATERIAL | PUBLICATIONS |
|---|---|---|
| Semiconducting organic complexes | | US20020158242 |
| Metal organometallic complexes | | US20060240279 |
| Cross-linkable compounds | | US20080220265 |
| Hole transporting materials | | |
| Triarylamines (e.g., TPD, -NPD) | | Appl. Phys. Lett. 51, 913 (1987) |
| | | US5061569 |

TABLE 1-continued
| MATERIAL | EXAMPLES OF MATERIAL | PUBLICATIONS |
|---|---|---|
| | 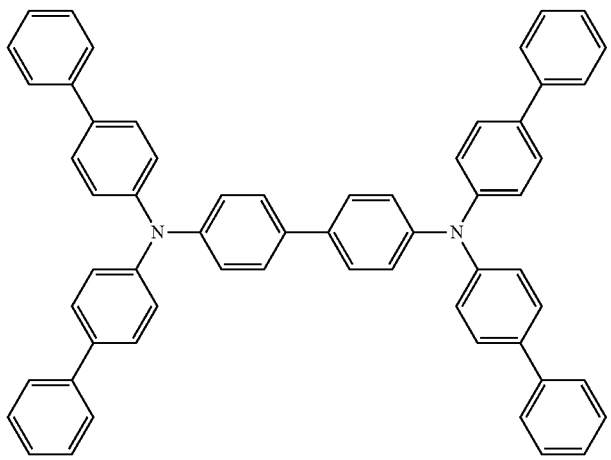 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1] | EP650955 |
| | 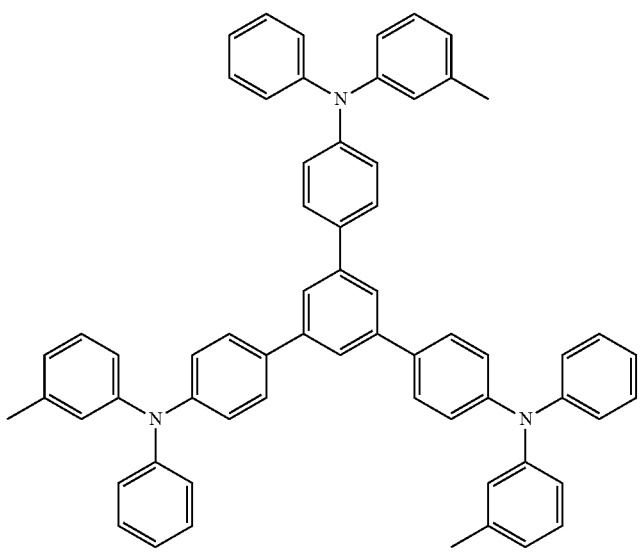 [SMILES: Cc1cccc(N(c2ccccc2)c2ccc(-c3cc(-c4ccc(N(c5ccccc5)c5cccc(C)c5)cc4)cc(-c4ccc(N(c5ccccc5)c5cccc(C)c5)cc4)c3)cc2)c1] | J. Mater. Chem. 3, 319 (1993) |
| | 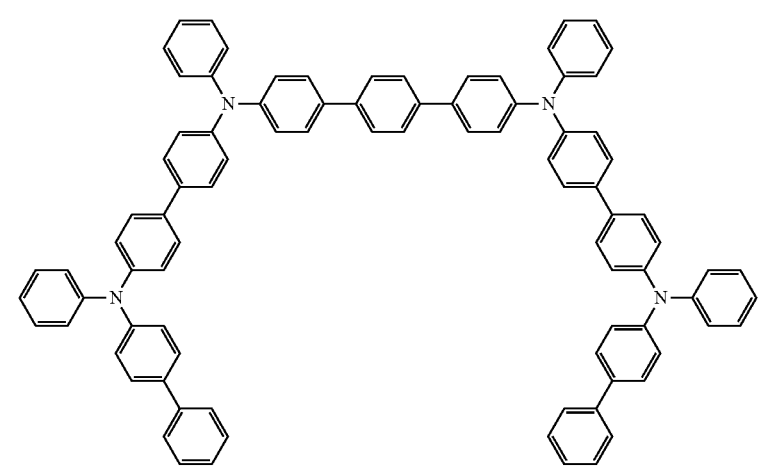 [SMILES: c1ccc(-c2ccc(N(c3ccccc3)c3ccc(-c4ccc(N(c5ccccc5)c5ccc(-c6ccc(-c7ccc(N(c8ccccc8)c8ccc(-c9ccc(N(c%10ccccc%10)c%10ccc(-c%11ccccc%11)cc%10)cc9)cc8)cc7)cc6)cc5)cc4)cc3)cc2)cc1] | Appl. Phys. Lett. 90, 183503 (2007) |

TABLE 1-continued

| MATERIAL | EXAMPLES OF MATERIAL | PUBLICATIONS |
|---|---|---|
| | | Appl. Phys. Lett. 90, 183503 (2007) |
| Triarylamine on spirofluorene core | | Synth. Met. 91, 209 (1997) |
| Arylamine carbazole compounds | | Adv. Mater. 6, 677 (1994), US20080124572 |
| Triarylamine with (di)benzothiophene/(di)benzofuran | | US20070278938, US20080106190 |

TABLE 1-continued

| MATERIAL | EXAMPLES OF MATERIAL | PUBLICATIONS |
| --- | --- | --- |
| Indolocarbazoles | | Synth. Met. 111, 421 (2000) |
| Isoindole compounds | | Chem. Mater. 15, 3148 (2003) |
| Metal carbene complexes | | US20080018221 |

Phosphorescent OLED host materials
Red hosts

| | | |
| --- | --- | --- |
| Arylcarbazoles | | Appl. Phys. Lett. 78, 1622 (2001) |

TABLE 1-continued
| MATERIAL | EXAMPLES OF MATERIAL | PUBLICATIONS |
|---|---|---|
| Metal 8-hydroxyquinolates (e.g., Alq$_3$, BAlq) | 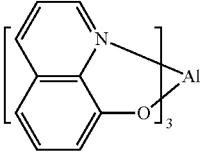 | Nature 395, 151 (1998) |
| | 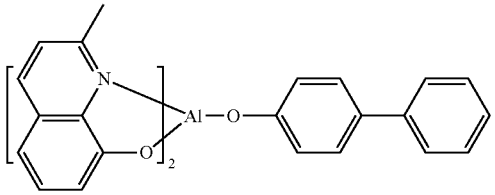 | US20060202194 |
| | 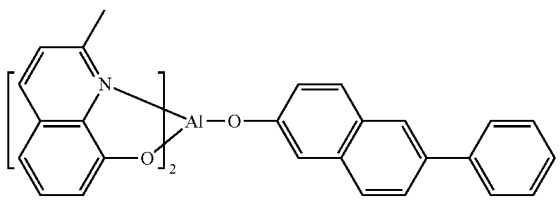 | WO2005014551 |
| | 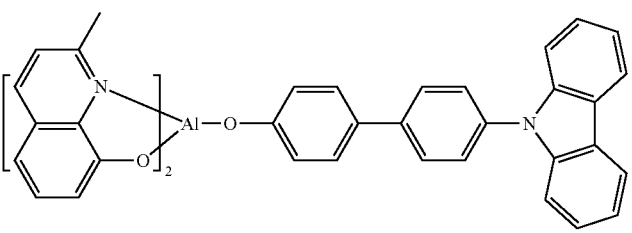 | WO2006072002 |
| Metal phenoxybenzothiazole compounds | 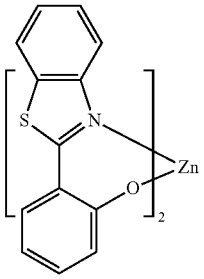 | Appl. Phys. Lett. 90, 123509 (2007) |
| Conjugated oligomers and polymers (e.g., polyfluorene) | 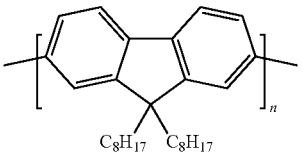 | Org. Electron. 1, 15 (2000) |
| Aromatic fused rings | 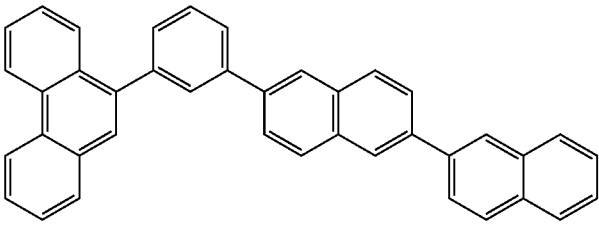 [SMILES: c1cc(-c2ccc3cc(-c4ccc5ccccc5c4)ccc3c2)cc(-c2cc3ccccc3c3ccccc23)c1] | WO2009066779, WO2009066778, WO2009063833, US20090045731, US20090045730, WO2009008311, US2009008605, US2009009065 |

TABLE 1-continued

| MATERIAL | EXAMPLES OF MATERIAL | PUBLICATIONS |
| --- | --- | --- |
| Zinc complexes | | WO2009062578 |

Green hosts

| MATERIAL | EXAMPLES OF MATERIAL | PUBLICATIONS |
| --- | --- | --- |
| Arylcarbazoles | | Appl. Phys. Lett. 78, 1622 (2001) |
| | | US20030175553 |
| | | WO2001039234 |
| Aryltriphenylene compounds | | US20060280965 |

TABLE 1-continued
| MATERIAL | EXAMPLES OF MATERIAL | PUBLICATIONS |
|---|---|---|
| | 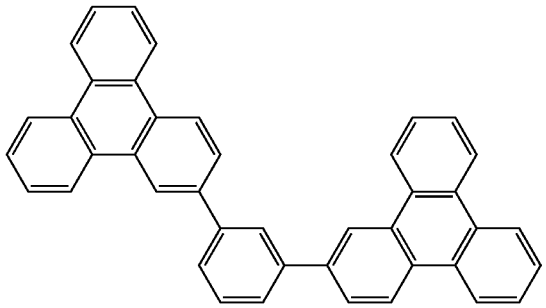 [SMILES: c1cc(-c2ccc3c4ccccc4c4ccccc4c3c2)cc(-c2ccc3c4ccccc4c4ccccc4c3c2)c1] | US20060280965 |
| | 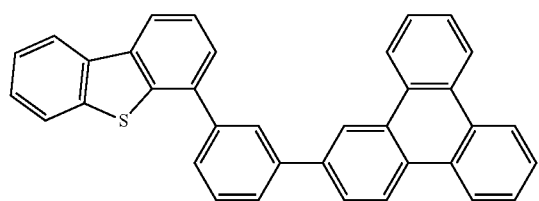 [SMILES: c1cc(-c2ccc3c4ccccc4c4ccccc4c3c2)cc(-c2cccc3c2sc2ccccc23)c1] | WO2009021126 |
| Donor acceptor type molecules | 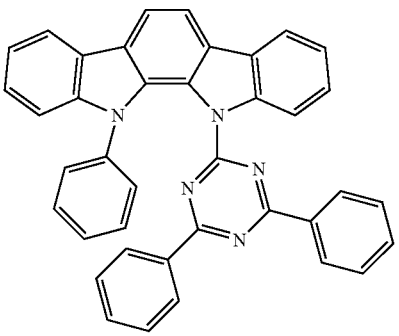 [SMILES: c1ccc(-c2nc(-c3ccccc3)nc(-n3c4ccccc4c4ccc5c6ccccc6n(-c6ccccc6)c5c43)n2)cc1] | WO2008056746 |
| Aza-carbazole/DBT/DBF | 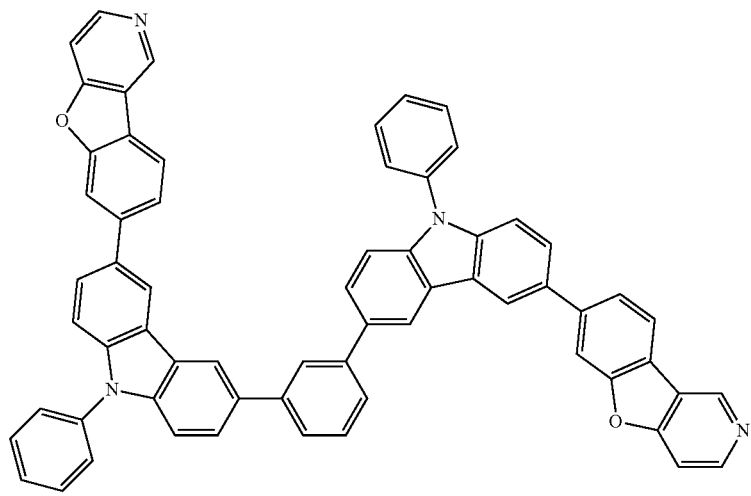 [SMILES: c1ccc(-n2c3ccc(-c4cccc(-c5ccc6c(c5)c5cc(-c7ccc8c(c7)oc7ccncc78)ccc5n6-c5ccccc5)c4)cc3c3cc(-c4ccc5c(c4)oc4ccncc45)ccc32)cc1] | JP2008074939 |
| Polymers (e.g., PVK) | 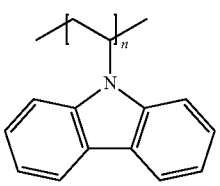 | Appl. Phys. Lett. 77, 2280 (2000) |

TABLE 1-continued
| MATERIAL | EXAMPLES OF MATERIAL | PUBLICATIONS |
|---|---|---|
| Spirofluorene compounds | 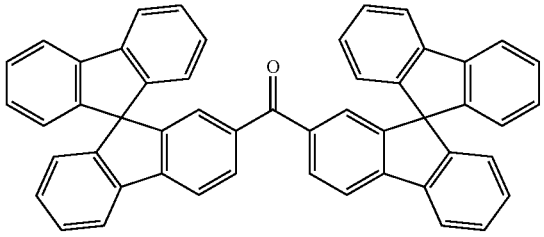 [SMILES: O=C(c1ccc2c(c1)C1(c3ccccc3-c3ccccc31)c1ccccc1-2)c1ccc2c(c1)C1(c3ccccc3-c3ccccc31)c1ccccc1-2] | WO2004093207 |
| Metal phenoxybenzooxazole compounds | 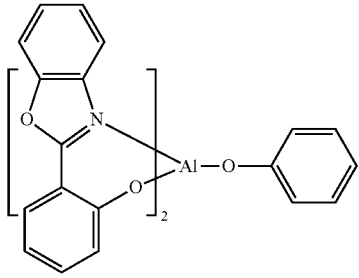 | WO2005089025 |
| | 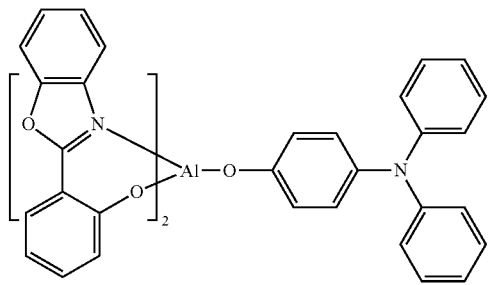 | WO2006132173 |
| | 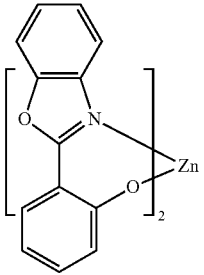 | JP200511610 |
| Spirofluorene-carbazole compounds | 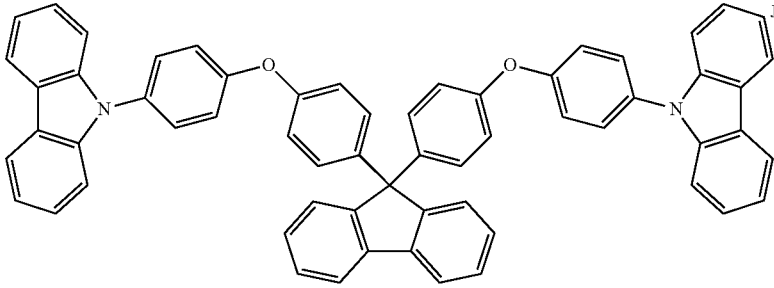 [SMILES: c1ccc2c(c1)-c1ccccc1C2(c1ccc(Oc2ccc(-n3c4ccccc4c4ccccc43)cc2)cc1)c1ccc(Oc2ccc(-n3c4ccccc4c4ccccc43)cc2)cc1] | JP2007254297 |

TABLE 1-continued
| MATERIAL | EXAMPLES OF MATERIAL | PUBLICATIONS |
|---|---|---|
| | 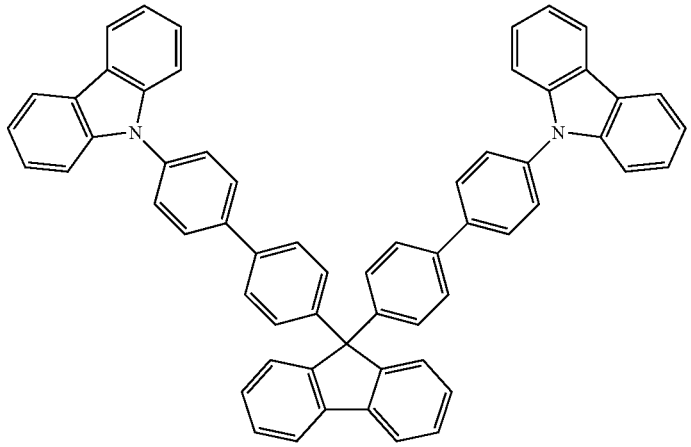 [SMILES: c1ccc2c(c1)-c1ccccc1C2(c1ccc(-c2ccc(-n3c4ccccc4c4ccccc43)cc2)cc1)c1ccc(-c2ccc(-n3c4ccccc4c4ccccc43)cc2)cc1] | JP2007254297 |
| Indolocarbazoles | 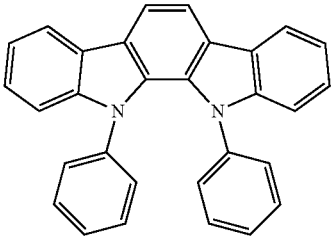 [SMILES: c1ccc(-n2c3ccccc3c3ccc4c5ccccc5n(-c5ccccc5)c4c32)cc1] | WO2007063796 |
| | 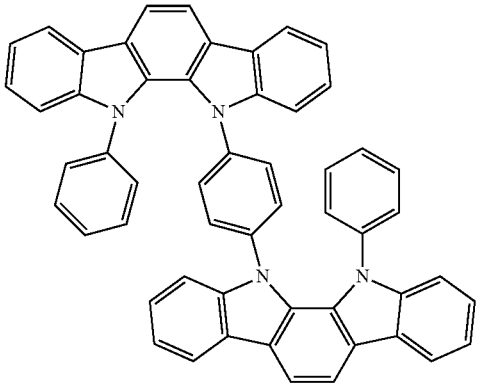 [SMILES: c1ccc(-n2c3ccccc3c3ccc4c5ccccc5n(-c5ccc(-n6c7ccccc7c7ccc8c9ccccc9n(-c9ccccc9)c8c76)cc5)c4c32)cc1] | WO2007063754 |
| 5-member ring electron deficient heterocycles (e.g., triazole, oxadiazole) | 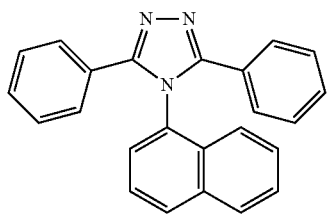 [SMILES: c1ccc(-c2nnc(-c3ccccc3)n2-c2cccc3ccccc23)cc1] | J. Appl. Phys. 90, 5048 (2001) |
| | 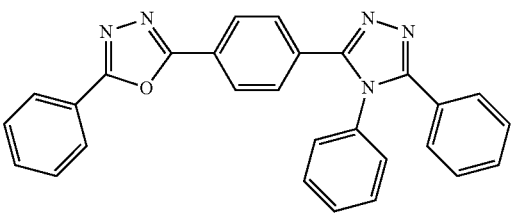 [SMILES: c1ccc(-c2nnc(-c3ccc(-c4nnc(-c5ccccc5)n4-c4ccccc4)cc3)o2)cc1] | WO2004107822 |

TABLE 1-continued

| MATERIAL | EXAMPLES OF MATERIAL | PUBLICATIONS |
|---|---|---|
| Tetraphenylene complexes | | US20050112407 |
| Metal phenoxypyridine compounds | | WO2005030900 |
| Metal coordination complexes (e.g., Zn, Al with N^N ligands) | | US20040137268, US20040137267 |

Blues hosts

| | | |
|---|---|---|
| Arylcarbazoles | | Appl. Phys. Lett, 82, 2422 (2003) |
| | | US20070190359 |

TABLE 1-continued
| MATERIAL | EXAMPLES OF MATERIAL | PUBLICATIONS |
|---|---|---|
| Dibenzothiophene/Dibenzofuran-carbazole compounds | 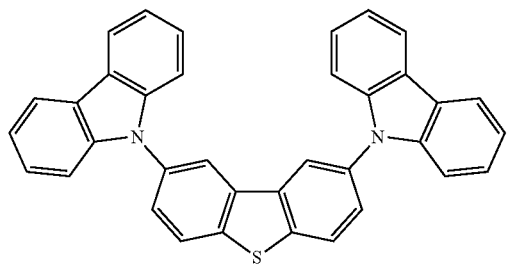 [SMILES: c1ccc2c(c1)c1ccccc1n2-c1ccc2sc3ccc(-n4c5ccccc5c5ccccc54)cc3c2c1] | WO2006114966, US20090167162 |
| | 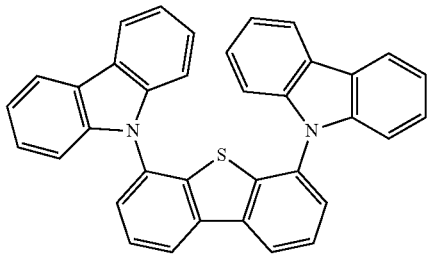 [SMILES: c1cc(-n2c3ccccc3c3ccccc32)c2sc3c(-n4c5ccccc5c5ccccc54)cccc3c2c1] | US20090167162 |
| | 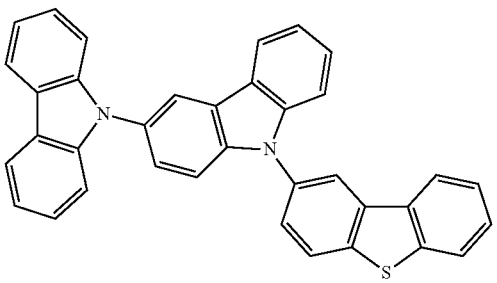 [SMILES: c1ccc2c(c1)sc1ccc(-n3c4ccccc4c4cc(-n5c6ccccc6c6ccccc65)ccc43)cc12] | WO2009086028 |
| | 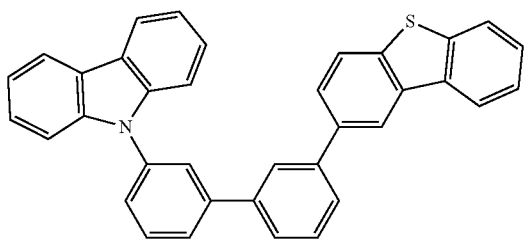 [SMILES: c1cc(-c2cccc(-n3c4ccccc4c4ccccc43)c2)cc(-c2ccc3sc4ccccc4c3c2)c1] | US20090030202, US20090017330 |
| Silicon aryl compounds | 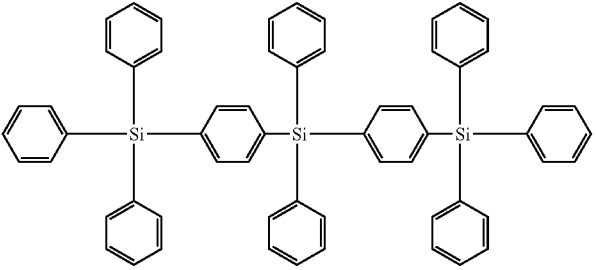 [SMILES: c1ccc([Si](c2ccccc2)(c2ccccc2)c2ccc([Si](c3ccccc3)(c3ccccc3)c3ccc([Si](c4ccccc4)(c4ccccc4)c4ccccc4)cc3)cc2)cc1] | US20050238919 |
| | 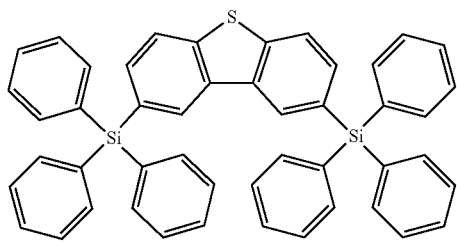 [SMILES: c1ccc([Si](c2ccccc2)(c2ccccc2)c2ccc3sc4ccc([Si](c5ccccc5)(c5ccccc5)c5ccccc5)cc4c3c2)cc1] | WO2009003898 |

TABLE 1-continued

| MATERIAL | EXAMPLES OF MATERIAL | PUBLICATIONS |
| --- | --- | --- |
| Silicon/Germanium aryl compounds | | EP2034538A |
| Aryl benzoyl ester | | WO2006100298 |
| High triplet metal organometallic complex | | US7154114 |

Phosphorescent dopants
Red dopants

| Heavy metal porphyrins (e.g., PtOEP) | | Nature 395, 151 (1998) |
| --- | --- | --- |
| Iridium(III) organometallic complexes | | Appl. Phys. Lett. 78, 1622 (2001) |

TABLE 1-continued

| MATERIAL | EXAMPLES OF MATERIAL | PUBLICATIONS |
|---|---|---|
| | | US2006835469 |
| | | US2006835469 |
| | | US20060202194 |
| | | US2006020194 |
| | | US20070087321 |

TABLE 1-continued

| MATERIAL | EXAMPLES OF MATERIAL | PUBLICATIONS |
|---|---|---|
| | | US20070087321 |
| | | Adv. Mater. 19, 739 (2007) |
| | | WO2009100991 |
| | | WO2008101842 |
| Platinum(II) organometallic complexes | | WO2003040257 |

TABLE 1-continued

| MATERIAL | EXAMPLES OF MATERIAL | PUBLICATIONS |
|---|---|---|
| Osminum(III) complexes | [structure with $F_3C$, pyrazole, pyridine, $Os(PPhMe_2)_2$] | Chem. Mater. 17, 3532 (2005) |
| Ruthenium(II) complexes | [structure with $^tBu$, pyrazole, isoquinoline, $Ru(PPhMe_2)_2$] | Adv. Mater. 17, 1059 (2005) |
| Rhenium (I), (II), and (III) complexes | [structure with quinolinolate, $Re-(CO)_4$] | US20050244673 |

Green dopants

| | | |
|---|---|---|
| Iridium(III) organometallic complexes | [tris-cyclometalated Ir complex structure] and its derivative | Inorg. Chem. 40, 1704 (2001) |
| | [Ir complex with acac ligand structure] | US20020034656 |

TABLE 1-continued

| MATERIAL | EXAMPLES OF MATERIAL | PUBLICATIONS |
|---|---|---|
| | | US7332232 |
| | | US20090108737 |
| | | US20090039776 |
| | | US6921915 |

TABLE 1-continued

| MATERIAL | EXAMPLES OF MATERIAL | PUBLICATIONS |
|---|---|---|
| | | US6687266 |
| | | Chem. Mater. 16, 2480 (2004) |
| | | US20070190359 |
| | | US20060008670<br>JP2007123392 |
| | | Adv. Mater. 16, 2003 (2004) |

TABLE 1-continued

| MATERIAL | EXAMPLES OF MATERIAL | PUBLICATIONS |
|---|---|---|
| | | Agnew. Chem. Int. Ed. 2006, 45, 7800 |
| | | WO2009050290 |
| | | US20090165846 |
| | | US20080015355 |
| Monomer for polymeric metal organometallic compounds | | US7250226, US7396598 |

TABLE 1-continued
| MATERIAL | EXAMPLES OF MATERIAL | PUBLICATIONS |
|---|---|---|
| Pt(II) organometallic complexes, including polydenated ligands | 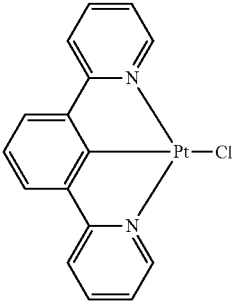 | Appl. Phys. Lett. 86, 153505 (2005) |
| | 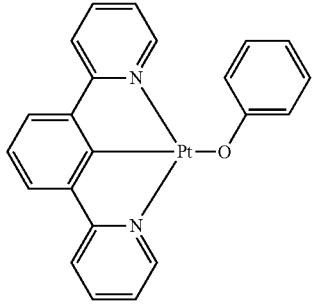 | Appl. Phys. Lett. 86, 153505 (2005) |
| | 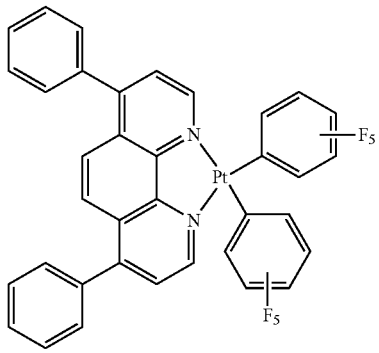 | Chem. Lett. 34, 592 (2005) |
| | 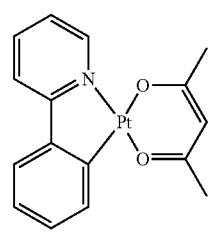 | WO2002015645 |
| | 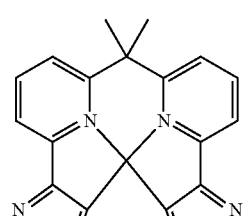 | US20060263635 |

TABLE 1-continued
| MATERIAL | EXAMPLES OF MATERIAL | PUBLICATIONS |
|---|---|---|
| Cu complexes | 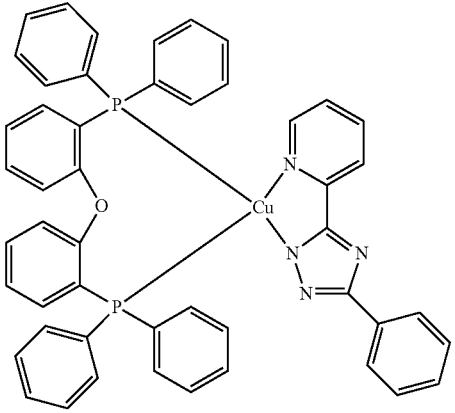 | WO2009000673 |
| Gold complexes | 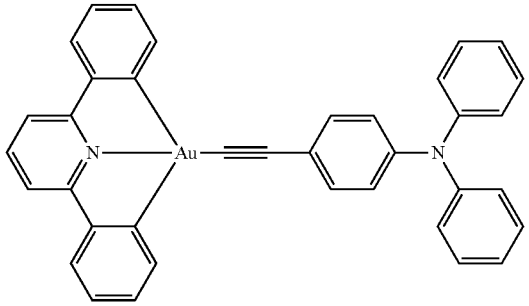 | Chem. Commun. 2906 (2005) |
| Rhenium(III) complexes | 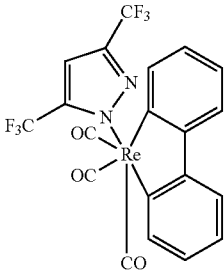 | Inorg. Chem. 42, 1248 (2003) |
| Deuterated organometallic complexes | 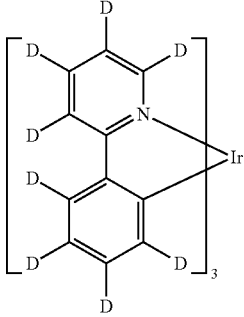 | US20030138657 |

TABLE 1-continued

| MATERIAL | EXAMPLES OF MATERIAL | PUBLICATIONS |
|---|---|---|
| Organometallic complexes with two or more metal centers | | US210030152802 |
| | | US7090928 |
| Blue dopants | | |
| Iridium(III) organometallic complexes | | WO2002002714 |
| | | WO2006009024 |
| | | US20060251923 |

TABLE 1-continued

| MATERIAL | EXAMPLES OF MATERIAL | PUBLICATIONS |
| --- | --- | --- |
|  |  | US7393599, WO2006056418, US20050260441, WO2005019373 |
|  |  | US7354505 |
|  |  | US7445855 |
|  |  | US20070190359, US20080297033 |
|  |  | US7338722 |
|  |  | US20020134984 |

TABLE 1-continued

| MATERIAL | EXAMPLES OF MATERIAL | PUBLICATIONS |
|---|---|---|
| | | Agnew. Chem. Int. Ed. 47, 1 (2008) |
| | | Chem. Mater. 18, 5119 (2006) |
| | | Inorg. Chem. 46, 4308 (2007) |
| | | WO2005132873 |
| | | WO2005123873 |
| | | WO2007004380 |

TABLE 1-continued

| MATERIAL | EXAMPLES OF MATERIAL | PUBLICATIONS |
|---|---|---|
| | | WO2006082742 |
| Osmium(II) complexes | | US7279704 |
| | | Organometallics 23, 3745 (2004) |
| Gold complexes | | Appl. Phys. Lett. 74, 1361 (1999) |
| Platinum(II) complexes | | WO2006098120, WO2006103874 |

TABLE 1-continued

| MATERIAL | EXAMPLES OF MATERIAL | PUBLICATIONS |
|---|---|---|
| Exciton/hole blocking layer materials | | |
| Bathocurpine compounds (e.g., BCP, BPhen) | 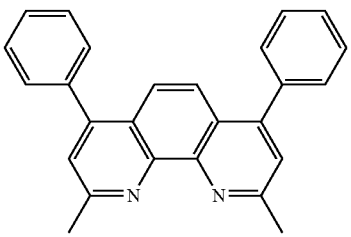 [SMILES: Cc1cc(-c2ccccc2)c2ccc3c(-c4ccccc4)cc(C)nc3c2n1] | Appl. Phys. Lett. 75, 4 (1999) |
| | 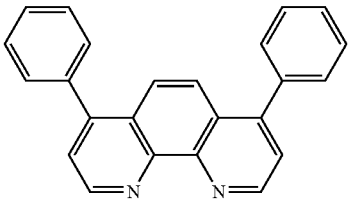 [SMILES: c1ccc(-c2ccnc3c2ccc2c(-c4ccccc4)ccnc23)cc1] | Appl. Phys. Lett. 79, 449 (2001) |
| Metal 8-hydroxyquinolates (e.g., BAlq) | 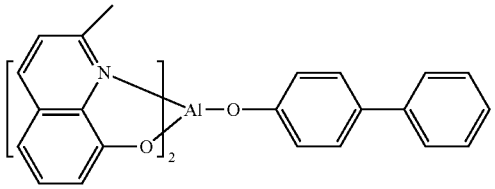 | Appl. Phys. Lett. 81, 162 (2002) |
| 5-member ring electron deficient heterocycles, such as triazole, oxadiazole, imidazole, benzoimidazole | 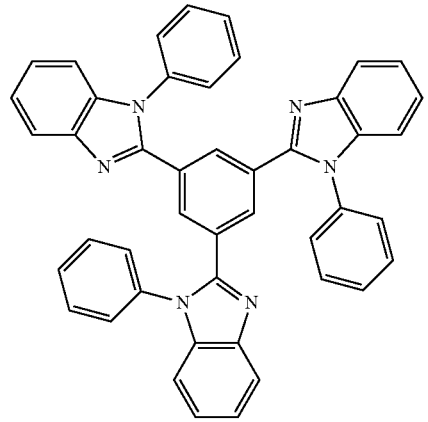 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 81, 162 (2002) |
| Triphenylene compounds | 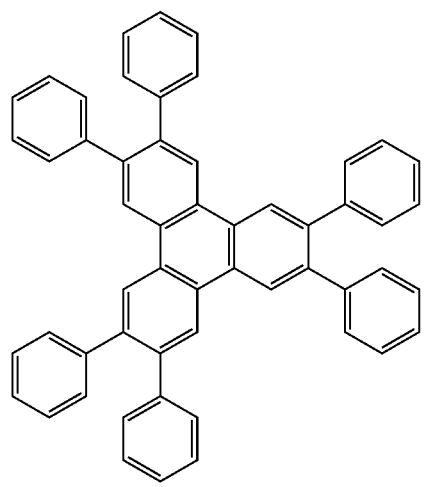 [SMILES: c1ccc(-c2cc3c4cc(-c5ccccc5)c(-c5ccccc5)cc4c4cc(-c5ccccc5)c(-c5ccccc5)cc4c3cc2-c2ccccc2)cc1] | US20050025993 |

TABLE 1-continued
| MATERIAL | EXAMPLES OF MATERIAL | PUBLICATIONS |
|---|---|---|
| Fluorinated aromatic compounds | 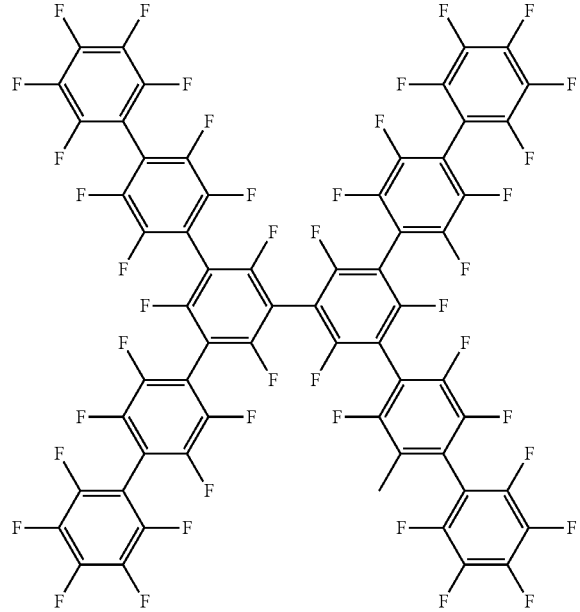 [SMILES: Cc1c(F)c(-c2c(F)c(-c3c(F)c(F)c(-c4c(F)c(F)c(F)c(F)c4F)c(F)c3F)c(F)c(-c3c(F)c(-c4c(F)c(F)c(-c5c(F)c(F)c(F)c(F)c5F)c(F)c4F)c(F)c(-c4c(F)c(F)c(-c5c(F)c(F)c(F)c(F)c5F)c(F)c4F)c3F)c2F)c(F)c(F)c1-c1c(F)c(F)c(F)c(F)c1F] | Appl. Phys. Lett. 79, 156 (2001) |
| Phenothiazine-S-oxide | 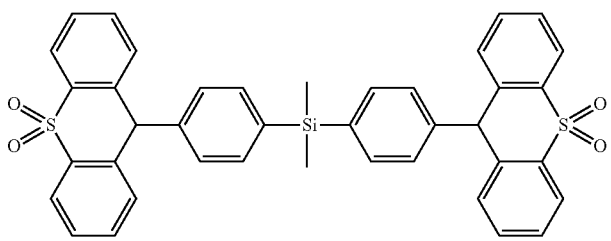 [SMILES: C[Si](C)(c1ccc(C2c3ccccc3S(=O)(=O)c3ccccc32)cc1)c1ccc(C2c3ccccc3S(=O)(=O)c3ccccc32)cc1] | WO2008132085 |
Electron transporting materials
| | | |
|---|---|---|
| Anthracene-benzoimidazole compounds | 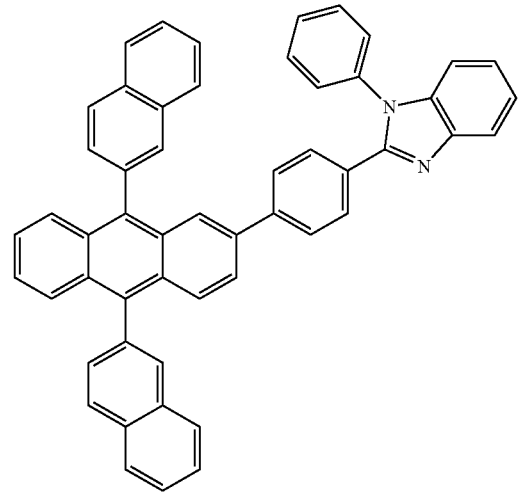 [SMILES: c1ccc(-n2c(-c3ccc(-c4ccc5c(-c6ccc7ccccc7c6)c6ccccc6c(-c6ccc7ccccc7c6)c5c4)cc3)nc3ccccc32)cc1] | WO2003060956 |

TABLE 1-continued

| MATERIAL | EXAMPLES OF MATERIAL | PUBLICATIONS |
| --- | --- | --- |
| | | US20090179554 |
| Aza triphenylene derivatives | | US20090115316 |
| Anthracene-benzothiazole compounds | | Appl. Phys. Lett. 89, 063504 (2006) |
| Metal 8-hydroxyquinolates (e.g., $Alq_3$, $Zrq_4$) | | Appl. Phys. Lett. 51, 913 (1987) US7230107 |
| Metal hydroxybenoquinolates | | Chem. Lett. 5, 905 (1993) |
| Bathocuprine compounds such as BCP, BPhen, etc | | Appl. Phys. Lett. 91, 263503 (2007) |

| MATERIAL | EXAMPLES OF MATERIAL | PUBLICATIONS |
|---|---|---|
| | | Appl. Phys. Lett. 79, 449 (2001) |
| 5-member ring electron deficient heterocycles (e.g., triazole, oxadiazole, imidazole, benzoimidazole) | | Appl. Phys. Lett. 74, 865 (1999) |
| | | Appl. Phys. Lett. 55, 1489 (1989) |
| | | Jpn. J. Apply. Phys. 32, L917 (1993) |
| Silole compounds | | Org. Electron. 4, 113 (2003) |
| Arylborane compounds | | J. Am. Chem. Soc. 120, 9714 (1998) |

TABLE 1-continued

| MATERIAL | EXAMPLES OF MATERIAL | PUBLICATIONS |
| --- | --- | --- |
| Fluorinated aromatic compounds | (perfluorinated polyphenyl structure) | J. Am. Chem. Soc. 122, 1832 (2000) |
| Fullerene (e.g., C60) | (C60 fullerene structure) | US20090101870 |
| Triazine complexes | (perfluorinated triaryltriazine structure) | US20040036077 |
| Zn (N ^ N) complexes | (bis-quinolinyl sulfonamide Zn complex) | US6528187 |

EXPERIMENTAL

Compound Examples

Example 1. Synthesis of Compound 1

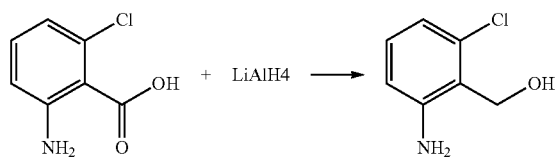 [SMILES: Nc1cccc(Cl)c1C(=O)O ; "LiAlH4" ; Nc1cccc(Cl)c1CO]

Synthesis of (2-amino-6-chlorophenyl)methanol

2-Amino-6-chlorobenzoic acid (25.0 g, 143 mmol) was dissolved in 120 mL of anhydrous THF in a 500 mL 2 neck round bottom flask. The solution was cooled in an ice-water bath. 215 mL of 1.0 M lithium aluminum hydride (LAH) THF solution was then added dropwise. After all of the LAH was added, the reaction mixture was allowed to warm up to room temperature and then stirred at room temperature overnight. ~10 mL of water was added to the reaction mixture followed by 7 g 15% NaOH. An additional 20 g of water was added to the reaction mixture. The organic THF phase was decanted and ~200 mL of ethyl acetate was added to the solid with stirring. $Na_2SO_4$ was added as a drying agent to the combined ethyl acetate organic portion and THF portion. The mixture was filtered and evaporated. ~20 g yellow solid was obtained and taken on to the next step without further purification.

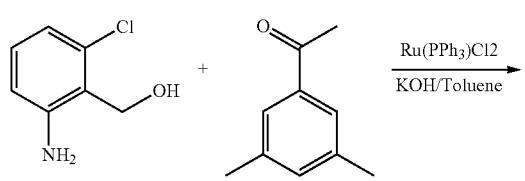

Kugelrohr distillation to give 23.5 g of crude product, which was crystallized from 60 mL of MeOH to give 8.6 g (32% yield) of the desired product.

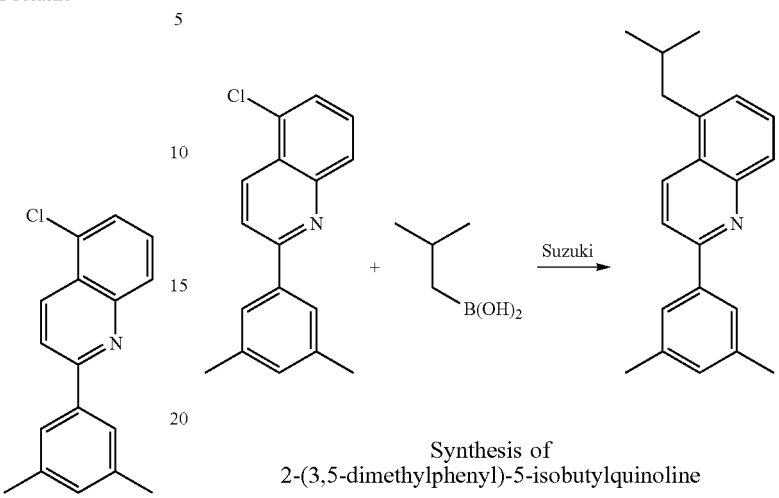

Synthesis of 2-(3,5-dimethylphenyl)-5-isobutylquinoline

5-Chloro-2-(3,5-dimethylphenyl)quinoline (4.3 g, 16.06 mmol), isobutylboronic acid (3.2 g, 31.4 mmol), dicyclohexyl(2',6'-dimethoxy-[1,1'-biphenyl]-2-yl)phosphine (0.538 g, 1.31 mmol), and potassium phosphate monohydrate (18.3 g, 79 mmol) were mixed in 114 mL of toluene. The system was degassed for 20 minutes. $Pd_2(dba)_3$ was then added and the system was refluxed overnight. After cooling to room temperature, the reaction mixture was filtered through a Celite® plug and eluted with dichloromethane. The product was further purified by a Kugelrohr distillation and then further purified by column chromatography using 5% ethyl acetate in hexanes. This was followed by another Kugelrohr distillation to give 3.2 g (72% yield) of product.

Synthesis of 5-chloro-2-(3,5-dimethylphenyl)quinoline (2-Amino-6-chlorophenyl)methanol (16 g, 102 mmol), 3,5-dimethylacetophenone (22.6 g, 152 mmol), $RuCl_2(PPh_3)_3$ (0.973 g, 1.015 mmol), and KOH (10.25 g, 183 mmol) were refluxed in 270 mL of toluene for 18 h. Water was collected from the reaction using a Dean-stark trap. The reaction mixture was allowed to cool to room temperature, filtered through a silica gel plug and eluted with 5% ethyl acetate in hexanes. The product was further purified by

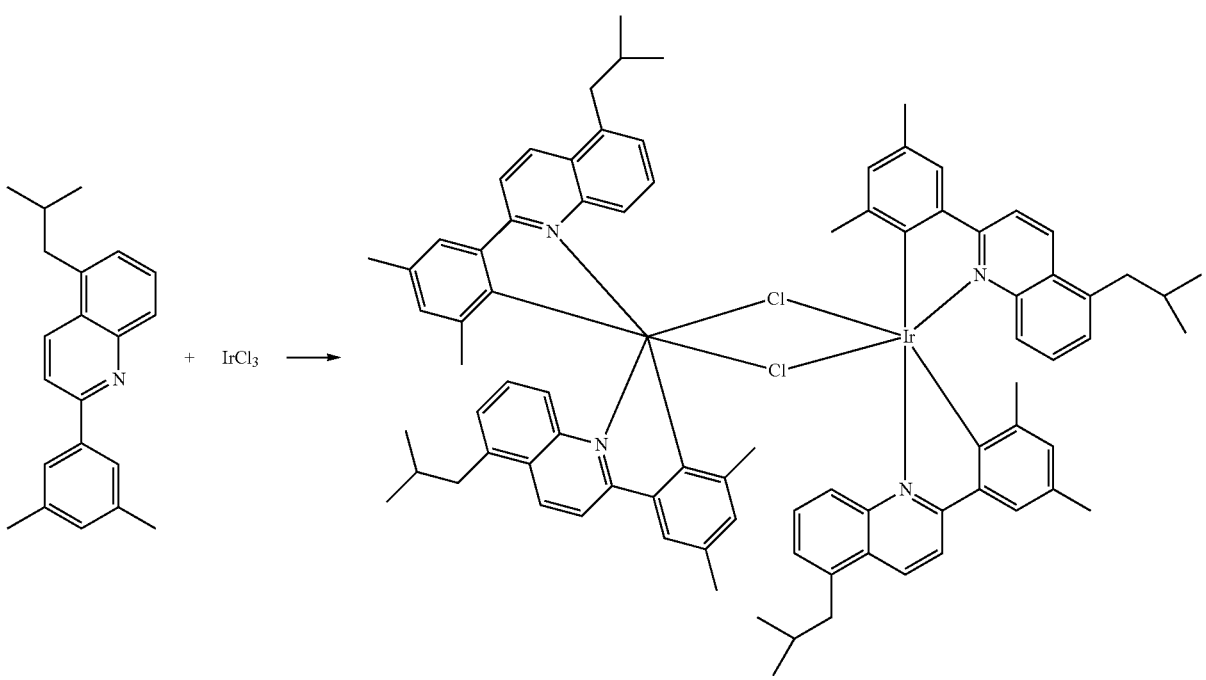

Synthesis of Iridium Dimer.
A mixture of 2-(3,5-dimethylphenyl)-5-isobutylquinoline (3.2 g, 11.06 mmol), $IrCl_3 \cdot 4H_2O$ (1.79 g, 4.83 mmol), 2-ethoxyethanol (45 mL) and water (105 mL) was refluxed under nitrogen overnight. The reaction mixture was filtered and washed with MeOH (3×10 mL). ~2.9 g of dimer was obtained after vacuum drying. The dimer was used for the next step without further purification.
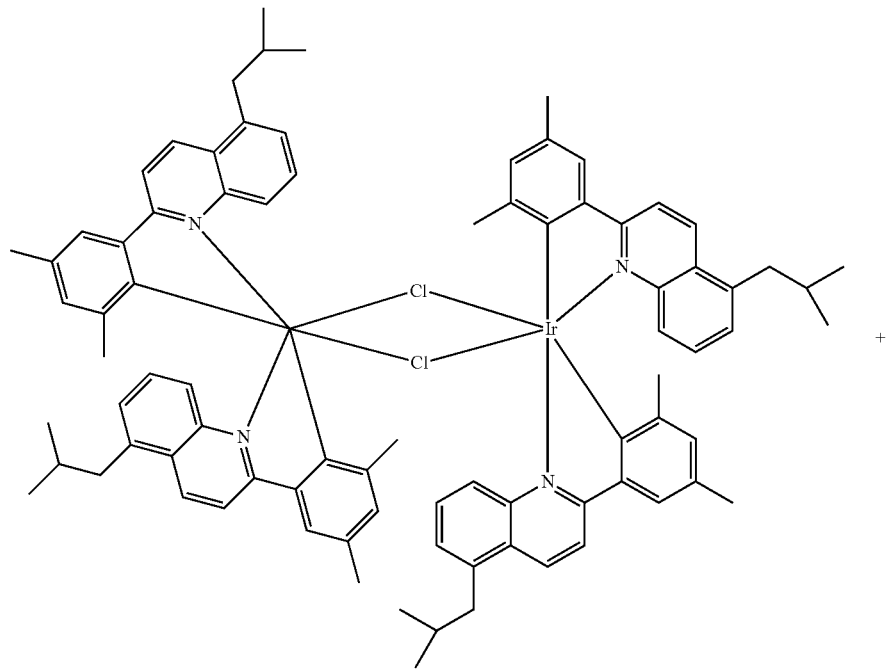
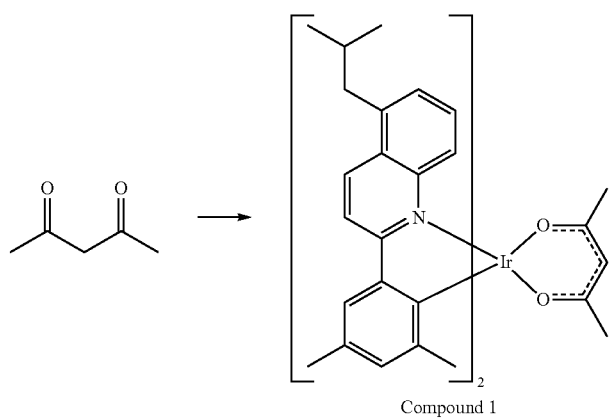
Compound 1

Synthesis of Compound 1.

Dimer (2.9 g, 1.80 mmol), pentane-2,4-dione (1.80 g, 18.02 mmol), K$_2$CO$_3$ (2.49 g, 18.02 mmol) and 2-ethoxyethanol (22 mL) were stirred at room temperature for 24 h. The precipitate was filtered and washed with methanol. The solid was further purified by passing it through a silica gel plug (that was pretreated with 15% triethylamine (TEA) in hexanes and eluted with methylene chloride. 2-Propanol was added to the filtrate. The filtrate was concentrated, but not to dryness. 1.6 g of product was obtained after filtration. The solid was sublimed twice under high vacuum at 240° C. to give 1.0 g (64%) of Compound 1.

Synthesis of Compound II-2

Synthesis of 5-cyclopentyl-2-(3,5-dimethylphenyl)quinoline

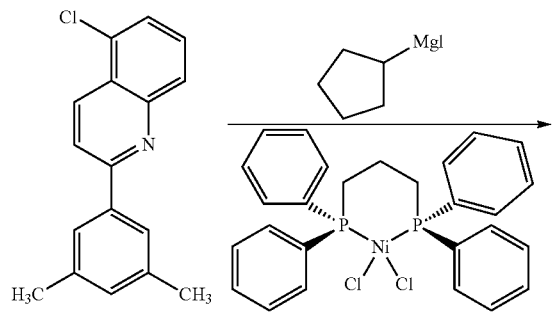

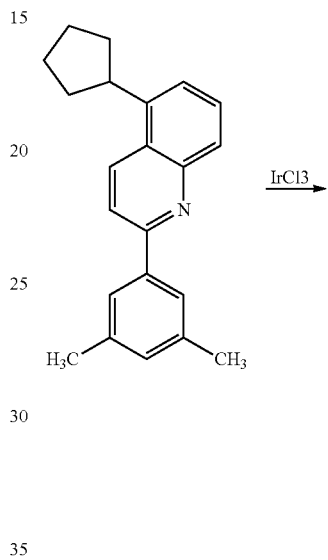

5-Chloro-2-(3,5-dimethylphenyl)quinoline (14.0 g, 52.3 mmol) and [1,3-bis(diphenylphosphino)propane]-dichloronickel (II) (0.10 g, 0.19 mmol) were dissolved in 250 mL of anhydrous diethyl ether under N2 atm. The reaction mixture was degassed and solution of cyclopentylmagnesium iodide (2 M solution in ether, 52 ml, 105 mmol) was added dropwise. The reaction mixture was stirred for 1 h, quenched with 20% aq. solution of ammonium chloride and extracted with ethyl acetate. The organic solution was dried over sodium sulfate, filtered and evaporated, providing yellow solid. Purification with column chromatography on silica gel, eluted with hexane/ethyl acetate 9/1 (v/v) mixture followed by crystallization from heptanes provided 5-cyclopentyl-2-(3,5-dimethylphenyl)quinoline as colorless crystals (12 g, 76% yield).

Synthesis of Ir(III) Dimer

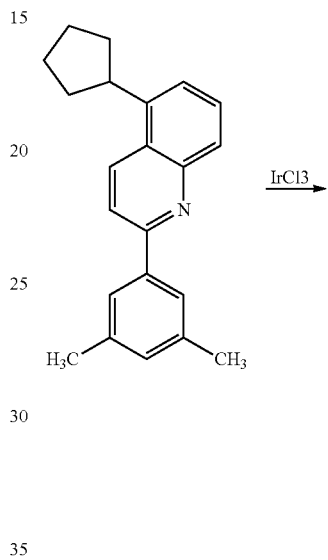

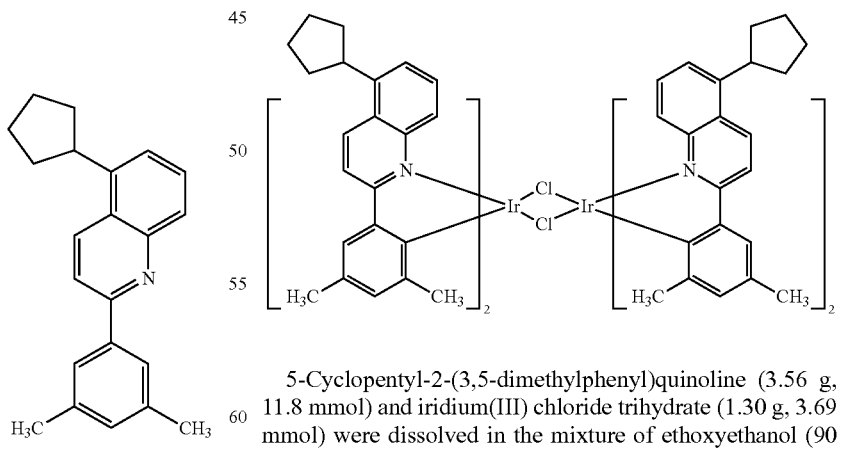

5-Cyclopentyl-2-(3,5-dimethylphenyl)quinoline (3.56 g, 11.8 mmol) and iridium(III) chloride trihydrate (1.30 g, 3.69 mmol) were dissolved in the mixture of ethoxyethanol (90 mL) and water (30 mL). Reaction mixture was degassed and heated to 105° C. for 24 h. The reaction mixture was then cooled down to room temperature and filtered through filter paper. The filtrate was washed with methanol and dried in vacuum, providing iridium complex dimer as dark solid 1.60 g (54% yield).

Synthesis of Compound II-2

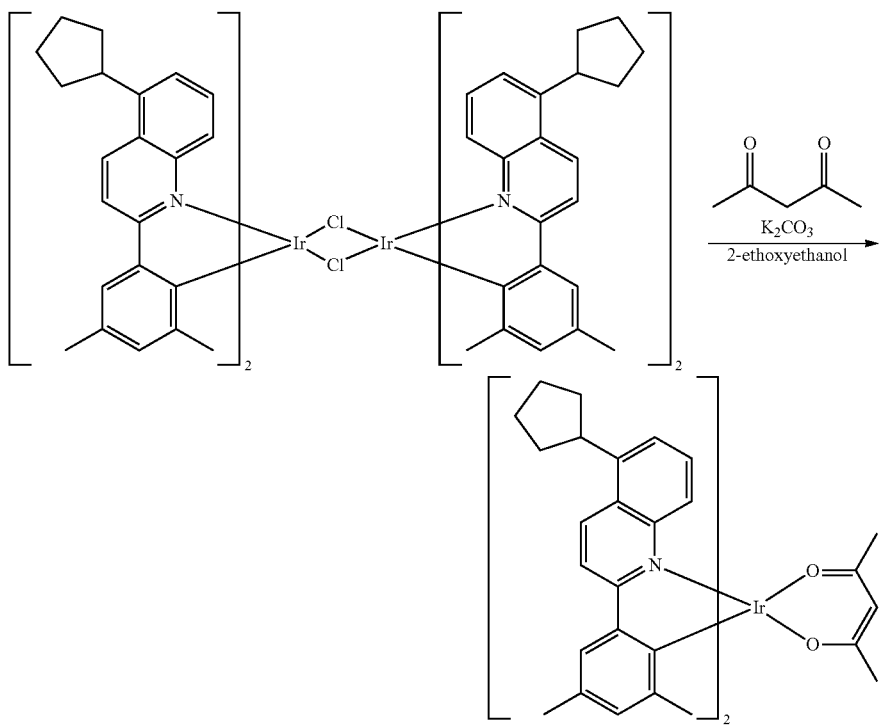

Iridium complex dimer (2.17 g, 1.31 mmol), acetylacetonate (1.31 g, 13.1 mmol) and potassium carbonate (1.81 g, 13.1 mmol) were suspended in 70 mL of ethoxyethanol, and stirred overnight under N2 at room temperature. The reaction mixture was then filtered through a pad of Celite®, washed with MeOH. Most of the red material was solubilized and passed through the Celite®. The Celite® was suspended in DCM, containing 10% of triethylamine and this suspension was combined with filtrate and evaporated. The residue was purified by column chromatography on silica gel, pre-treated with Et$_3$N, eluted with hexane/dichloromethane mixture, providing a dark red solid. The product was further purified by recrystallizing from dichloromethane and isopropanol mixture to give desired product (1.67 g, 72% yield).

Device Examples

All example devices were fabricated by high vacuum (<10$^{-7}$ Torr) thermal evaporation. The anode electrode is 1200 Å of indium tin oxide (ITO). The cathode consisted of 10 Å of LiF followed by 1000 Å of Al. All devices are encapsulated with a glass lid sealed with an epoxy resin in a nitrogen glove box (<1 ppm of H$_2$O and O$_2$) immediately after fabrication, and a moisture getter was incorporated inside the package.

The organic stack of the device examples consisted of sequentially, from the 1200 Å ITO surface, 100 Å of Compound A as the hole injection layer (HIL), 400 Å of 4,4'-bis[N-(1-naphthyl)-N-phenylamino]biphenyl (α-NPD) as the hole transporting layer (HTL), 300 Å of the 7 wt % invention compound doped into BAlq host as the emissive layer (EML), 550 Å of Alq$_3$ (tris-8-hydroxyquinoline aluminum) as the ETL.

Comparative Examples were fabricated similarly to the Device Examples except that Compound B, C or D was used as the emitter in the EML.

As used herein, the following compounds have the following structures:

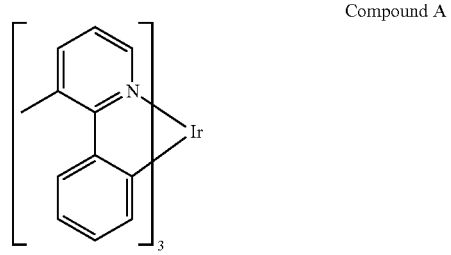

Compound A

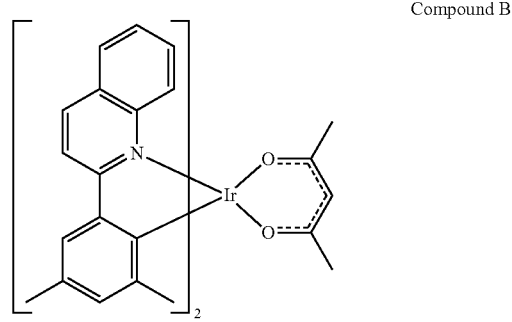

Compound B

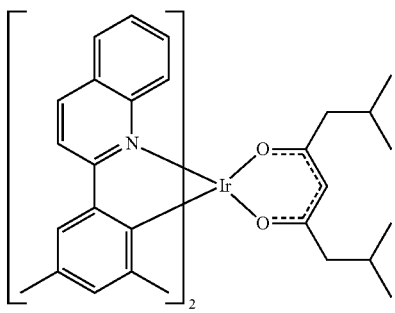

Compound C

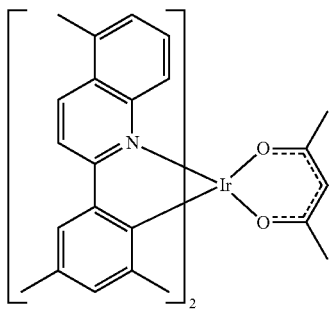

Compound D

Particular emissive dopants for the emissive layer of an OLED are provided. These compounds may lead to devices having particularly good properties.

The device structures and device data are summarized in Table 2.

the same as the FWHM of Compound C (58 nm). The color saturation (CIE) of Compound 1 and Compound B are also the same. These results indicate that Compound 1 is a more efficient red emitter than Compounds B, C and D with a desirable narrower FWHM.

Compound 1 also has almost a double lifetime at room temperature compared to Compound D. The only difference between these two compounds is that Compound 1 has a bulkier group at 5-position. This clearly indicates that a bulkier group than methyl in the 5-position of 2-phenylquinoline may indeed provide a significant improvement in overall device performance.

Additional Device Examples

Additional device examples were fabricated to evaluate the compound having Formula III wherein $R_4$ comprises a cycloalkyl group. These additional example devices were fabricated by high vacuum (<$10^{-7}$ Torr) thermal evaporation. The anode electrode is 1200 Å of ITO. The cathode consisted of 10 Å of LiF followed by 1,000 Å of Al. All devices are encapsulated with a glass lid sealed with an epoxy resin in a nitrogen glove box (<1 ppm of $H_2O$ and $O_2$) immediately after fabrication, and a moisture getter was incorporated inside the package.

The organic stack of the additional device examples consisted of sequentially, from the ITO surface, 100 Å of Compound A as the HIL, 400 Å of 4,4'-bis[N-(1-naphthyl)-N-phenylamino]biphenyl (α-NPD) as the HTL, 300 Å of the invention compound doped in Balq as host with 6 wt % of an Ir phosphorescent compound as the EML, 550 Å of $Alq_3$ (tris-8-hydroxyquinoline aluminum) as the ETL.

The device structures and device data from the additional device examples are summarized in Table 3 below.

TABLE 2

| | 1931 CIE | | $\lambda_{max}$ | FWHM | At 1,000 nits | | | | | At 40 mA/cm² | | |
| | | | | | V | LE | EQE | PE | cd/A per | $L_0$ | $LT_{80\%}$ [h] | |
| Emitter | x | y | [nm] | [nm] | [V] | [cd/A] | [%] | [lm/W] | EQE | [nits] | RT | 70° C. |
| Compound 1 (Device Example) | 0.665 | 0.331 | 622 | 58 | 7.8 | 22.2 | 20.5 | 9.0 | 1.08 | 6,852 | 600 | 66 |
| Compound B (Comparative Example) | 0.667 | 0.331 | 622 | 62 | 8.1 | 19.9 | 18.8 | 7.7 | 1.06 | 6,447 | 878 | 70 |
| Compound C (Comparative Example) | 0.662 | 0.335 | 620 | 58 | 7.4 | 21.9 | 18.9 | 9.3 | 1.16 | 6,927 | 565 | 73 |
| Compound D (Comparative Example) | 0.664 | 0.334 | 620 | 64 | 8.1 | 21.1 | 19.4 | 8.1 | 1.09 | 6,666 | 321 | 44 |

As seen from the Table 2, the EQE of Compound 1 at 1000 nits is up to 10% higher than Compounds B, C, and D. Additionally, the EL spectral full width at half maximum (FWHW) of Compound 1 (58 nm) is also narrower than Compound B (62 nm) and Compound D (64 nm), which is a desirable device property. The FWHM of Compound 1 is

TABLE 3

| | | | | | | At 1000 nits | | | | |
| | Alq | 1931 CIE | | λ max | FWHM | Volt | LE | EQE | PE | cd/Aper |
| Emitter | [Å] | x | y | [nm] | [nm] | [V] | [cd/A] | [%] | [lm/W] | EQE |
| Compound II-2 | 550 Å | 0.662 | 0.335 | 620 | 60 | 8.3 | 23.2 | 20.4 | 8.8 | 1.1 |

As can be seen from Table 3, the example device with Compound II-2 showed saturated red color and high luminous efficiency. The LE was measured at 23.2 cd/A compared to 22.2 cd/A for Compound 1.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

The invention claimed is:

1. A compound having the formula:

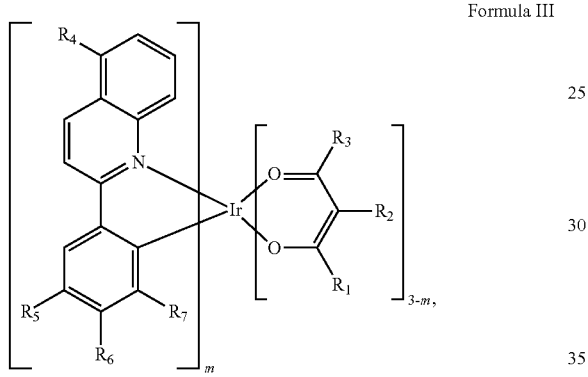

Formula III wherein $R_1$, $R_2$, $R_3$, $R_5$, $R_6$ and $R_7$ are independently selected from the group consisting of hydrogen, deuterium, alkyl, silyl, alkoxy, amino, alkenyl, alkynyl, arylkyl, aryl and heteroaryl;

wherein $R_4$ comprises an unsubstituted cycloalkyl group selected from the group consisting of cyclobutyl, cyclopentyl, cyclohexyl, and cycloheptyl; and wherein m is 1, 2, or 3.

2. The compound of claim 1, wherein $R_4$ is an unsubstituted cyclobutyl moiety.

3. The compound of claim 1, wherein $R_4$ is an unsubstituted cylopentyl moiety.

4. The compound of claim 1, wherein $R_4$ is an unsubstituted cyclohexyl moiety.

5. The compound of claim 1, wherein $R_4$ is an unsubstituted cycloheptyl moiety.

6. The compound of claim 1, wherein $R_4$ is an unsubstituted cycloalkyl group selected from the group consisting of cyclobutyl, cyclopentyl, cyclohexyl, and cycloheptyl.

7. The compound of claim 1, wherein each of $R_1$ and $R_3$ is a branched alkyl with branching at a position further than the α position to the carbonyl group.

8. The compound of claim 1, wherein each of $R_5$ and $R_7$ are methyl, and $R_6$ is hydrogen.

9. The compound of claim 1, wherein each of $R_5$ and $R_6$ are methyl, and $R_7$ is hydrogen.

10. The compound of claim 1, wherein each of $R_5$, $R_6$ and $R_7$ are methyl.

11. The compound of claim 1, wherein the compound is selected from the group consisting of:

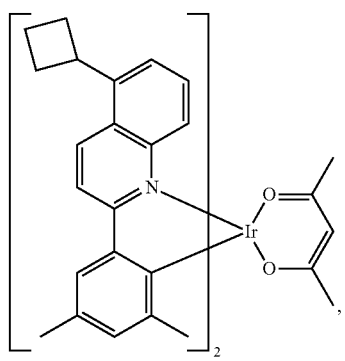

Compound II-1

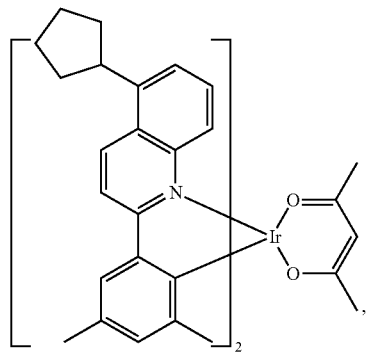

Compound II-2

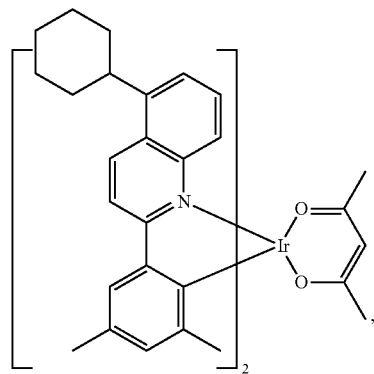

Compound II-3

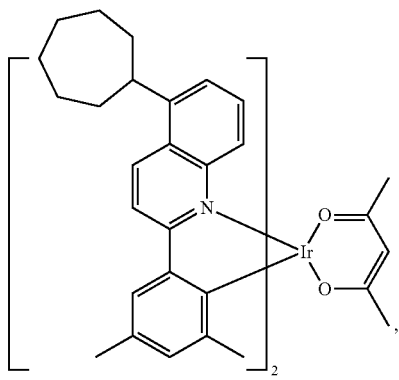

Compound II-4

Compound II-5
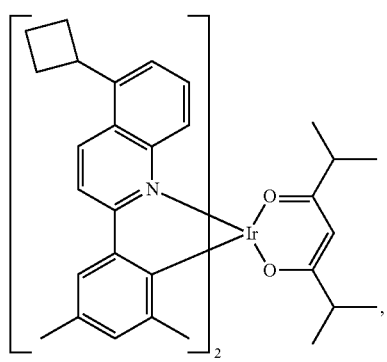
Compound II-6
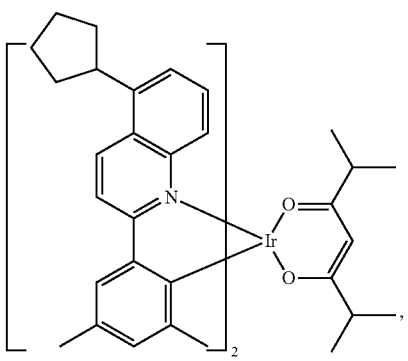
Compound II-7
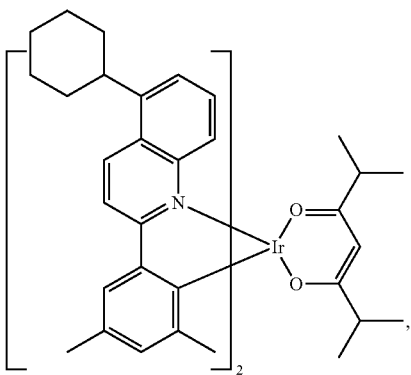
Compound II-8
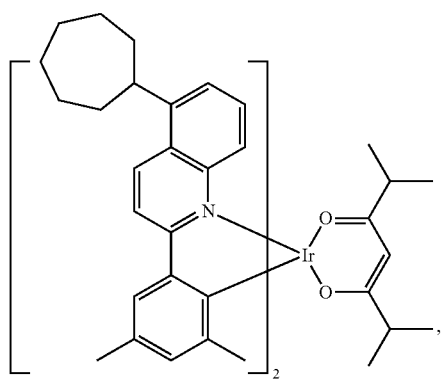
Compound II-9
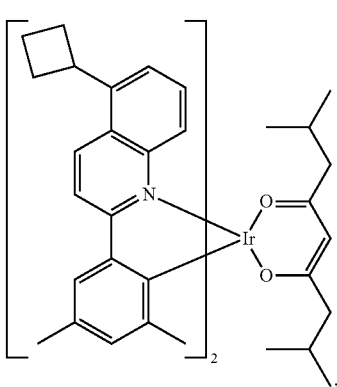
Compound II-10
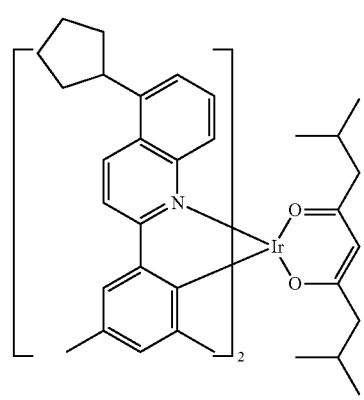
Compound II-11
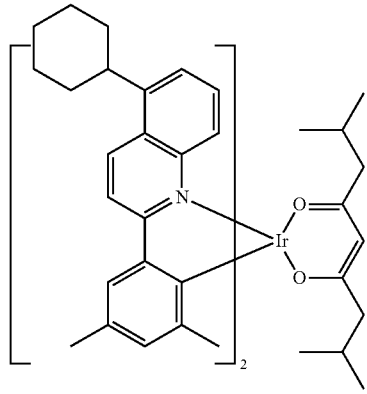
Compound II-12
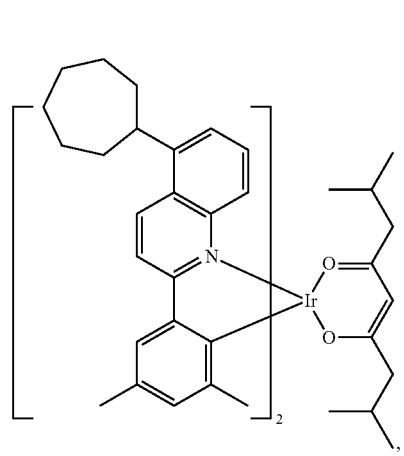

Compound II-13
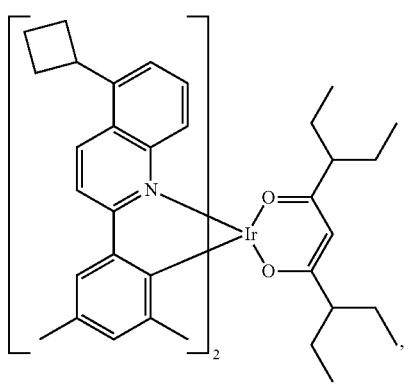
Compound II-14
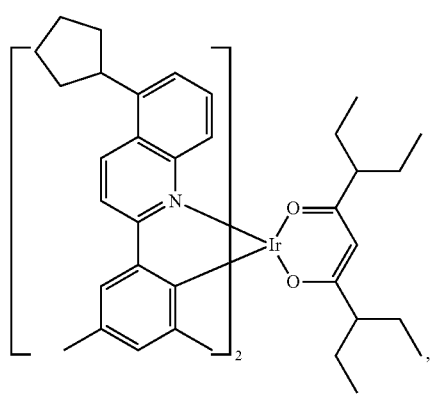
Compound II-15
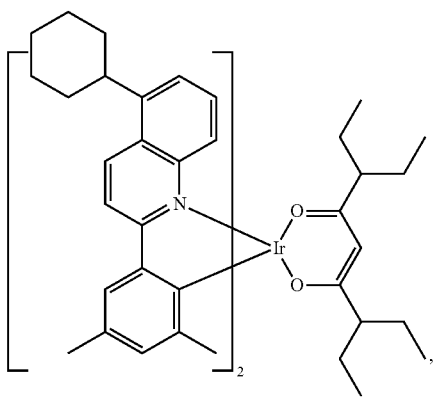
Compound II-16
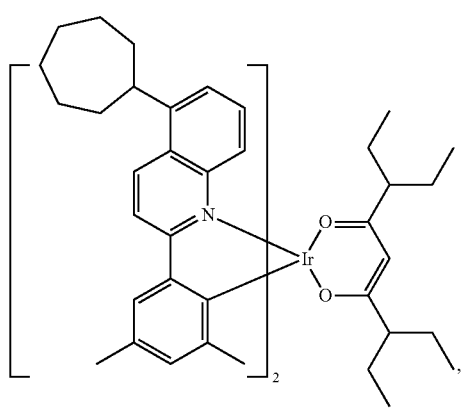
Compound II-17
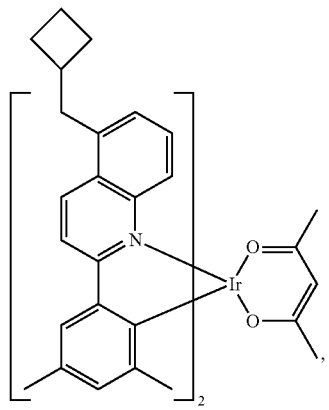
Compound II-18
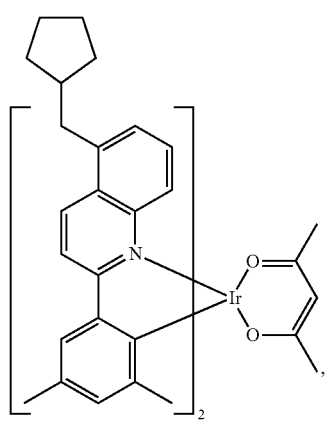
Compound II-19

Compound II-20
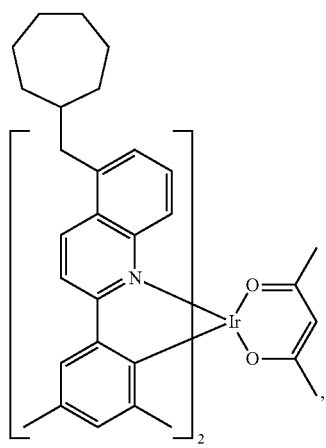
Compound II-21
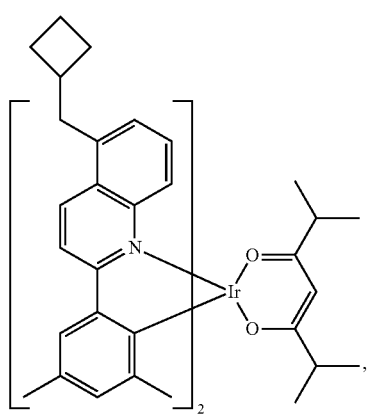
Compound II-22
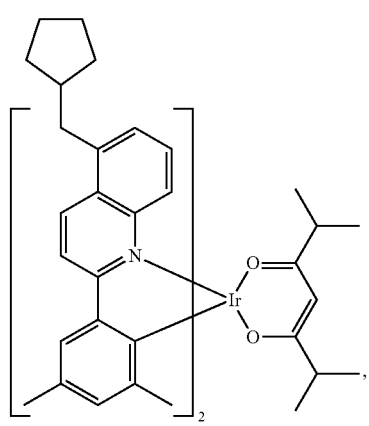
Compound II-23
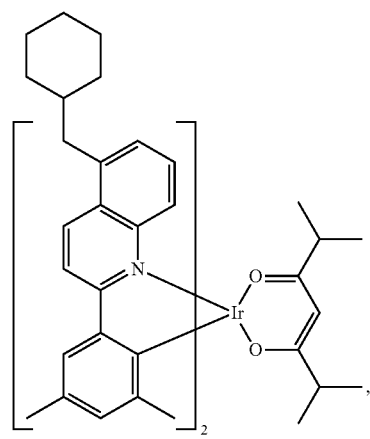
Compound II-24
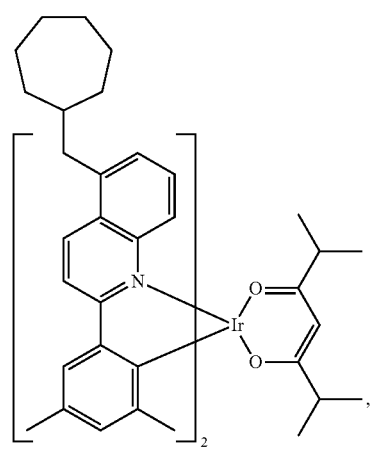
Compound II-25
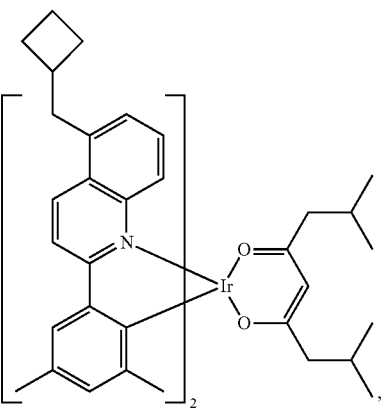

Compound II-26
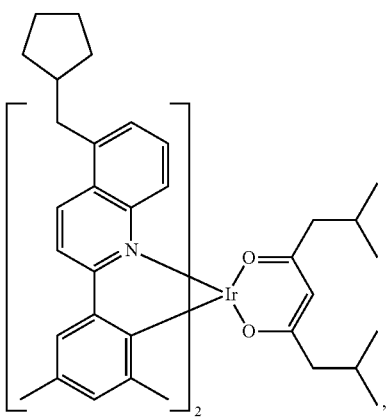
Compound II-29
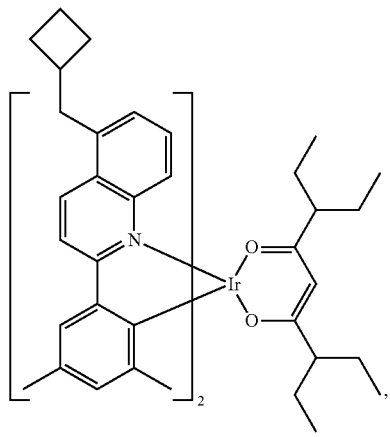
Compound II-27
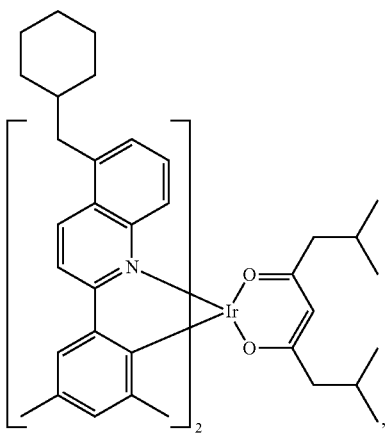
Compound II-30
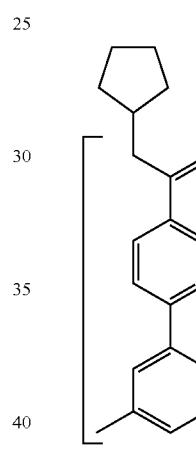
Compound II-28
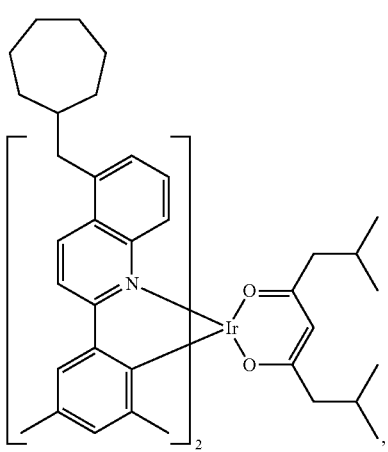
Compound II-31
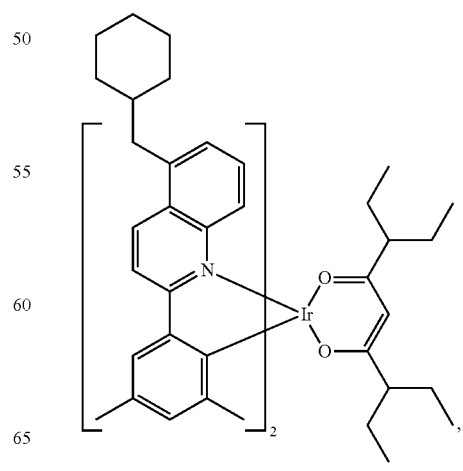

Compound II-32
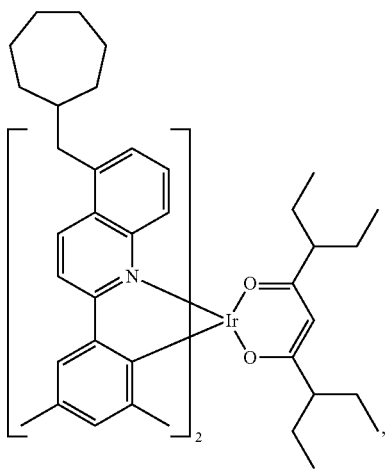
Compound II-35
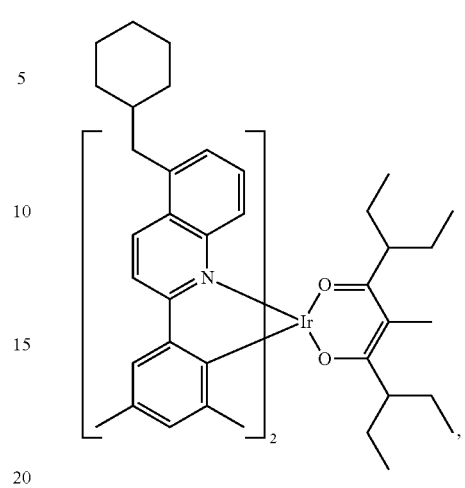
Compound II-33
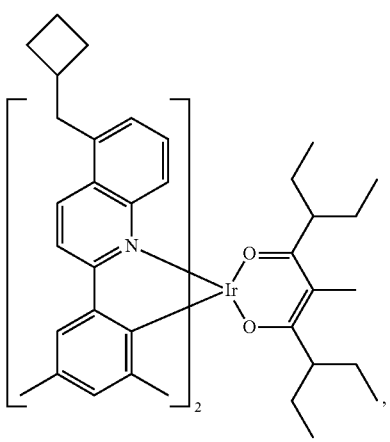
Compound II-36
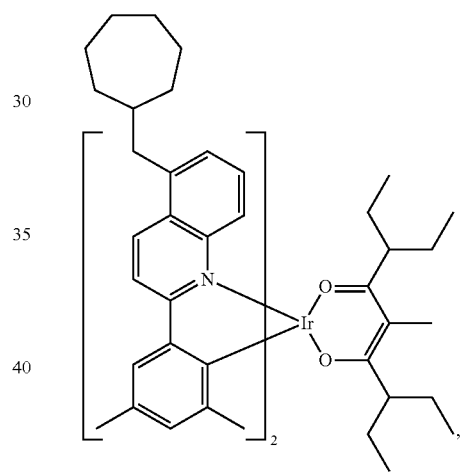
Compound II-34
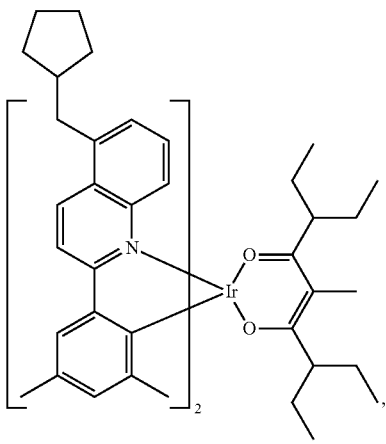
Compound II-37
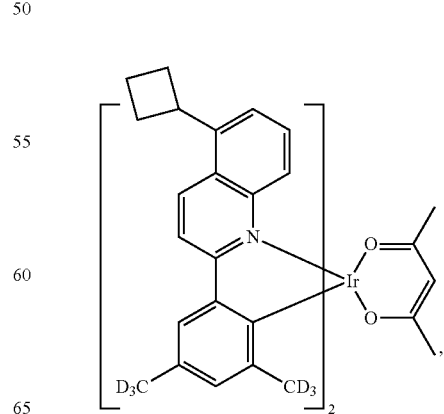

Compound II-38
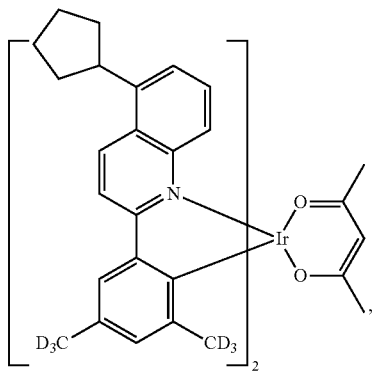
Compound II-39
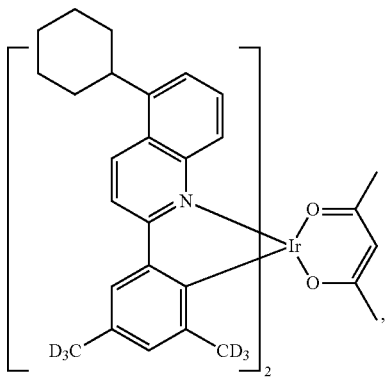
Compound II-40
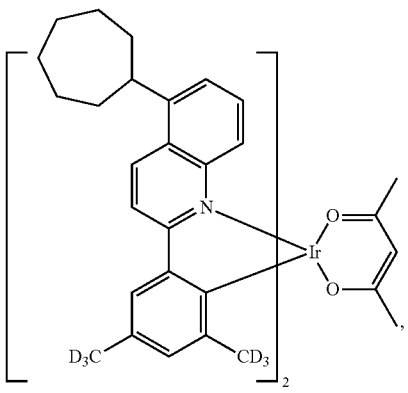
Compound II-41
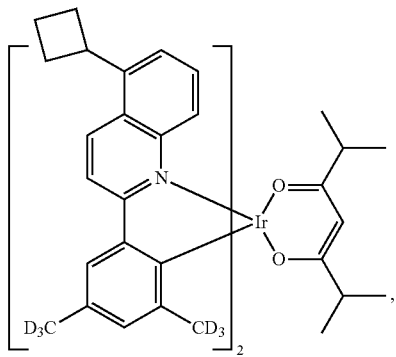
Compound II-42
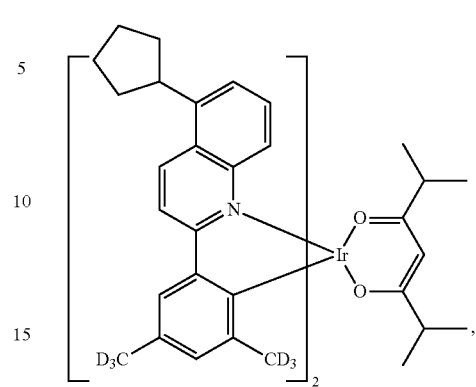
Compound II-43
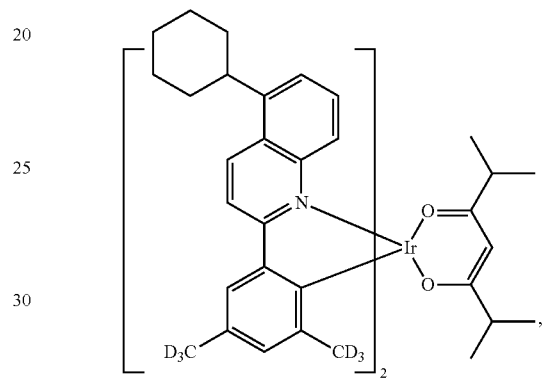
Compound II-44
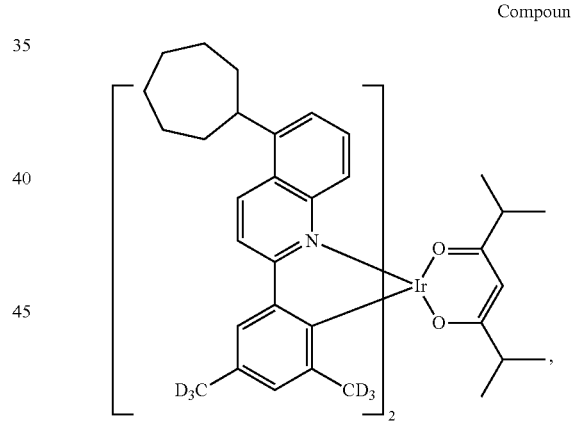
Compound II-45
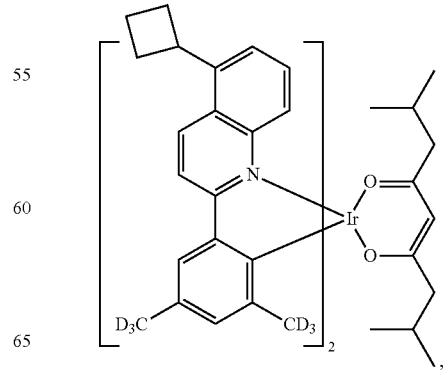

Compound II-46
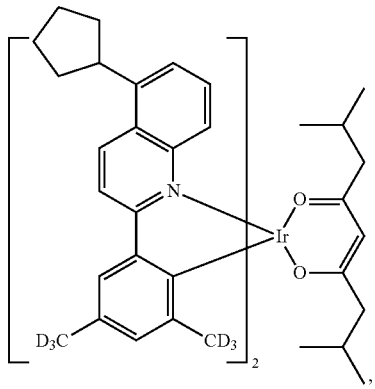
Compound II-47
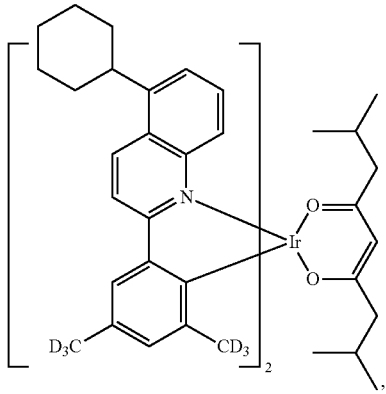
Compound II-48
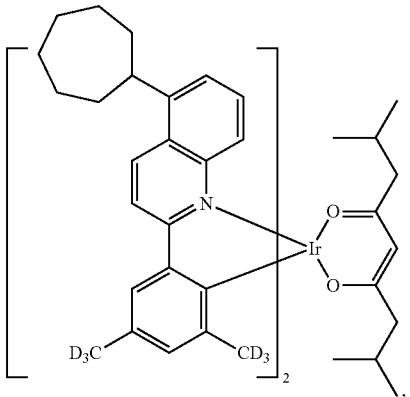
Compound II-49
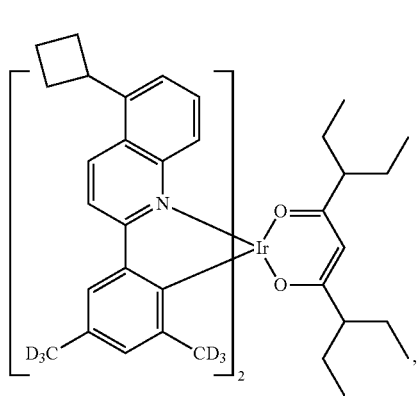
Compound II-50
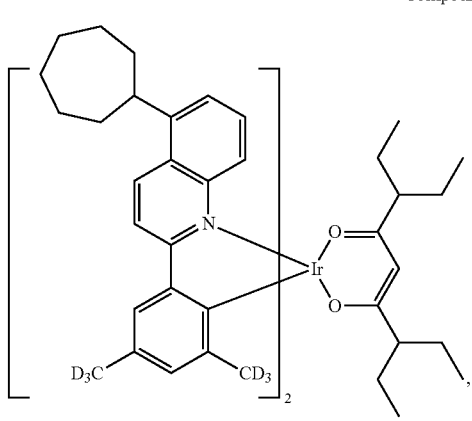
Compound II-51
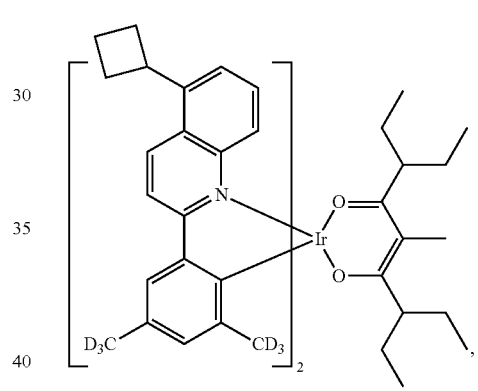
Compound II-52
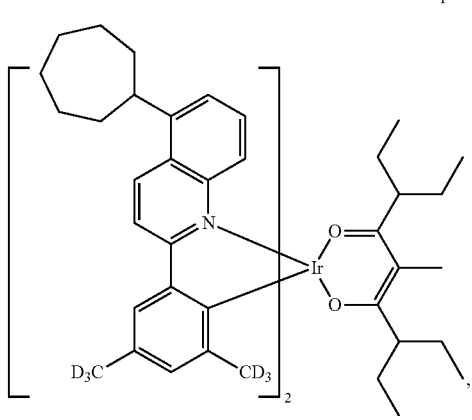

Compound II-53
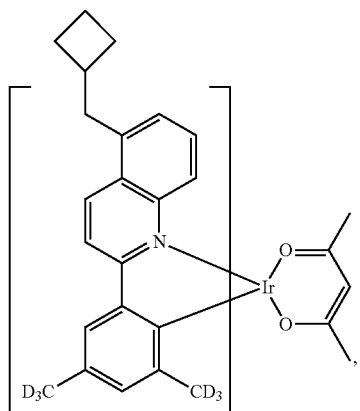
Compound II-54
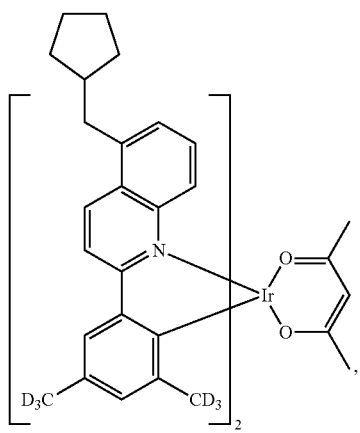
Compound II-55
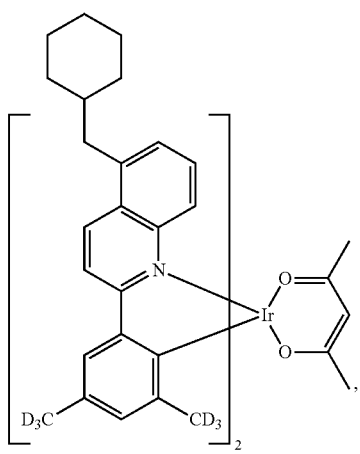
Compound II-56
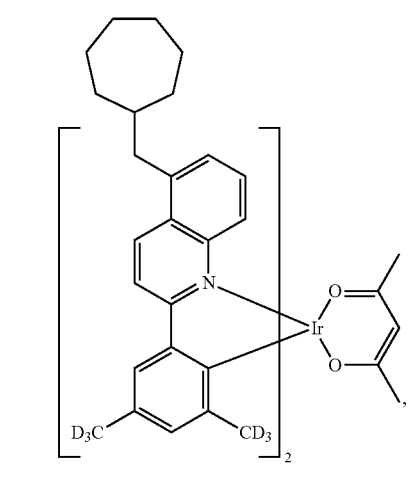
Compound II-57
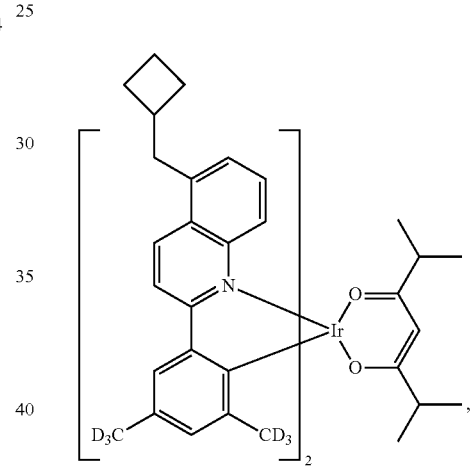
Compound II-58
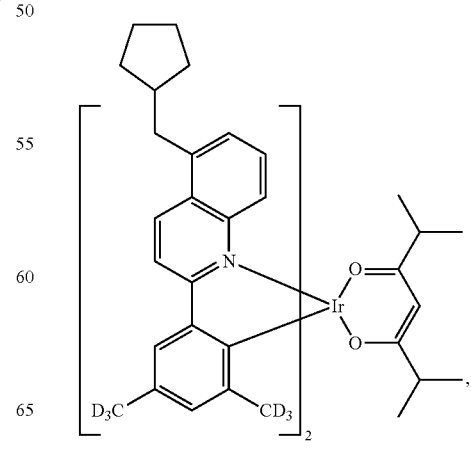

Compound II-59
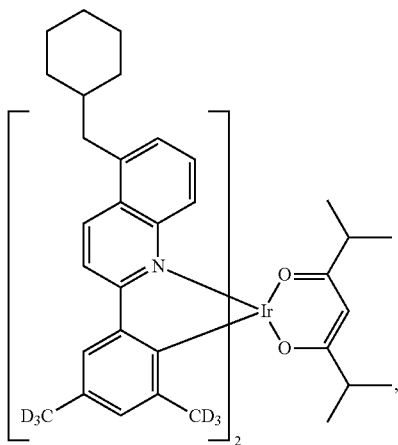
Compound II-62
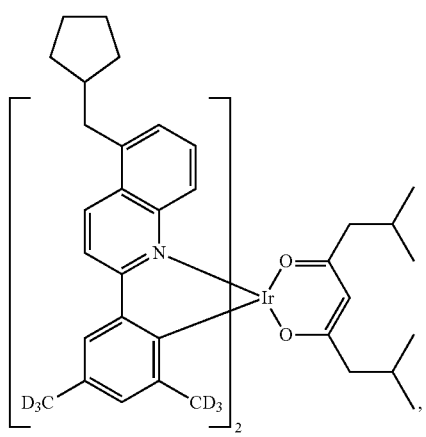
Compound II-60
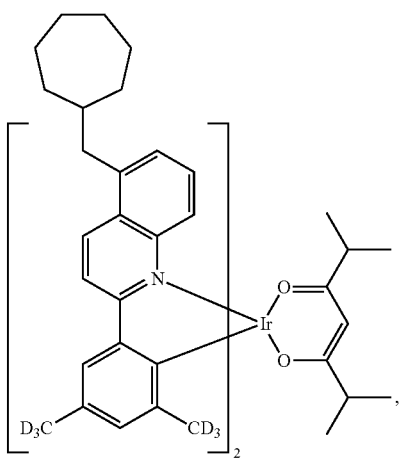
Compound II-63
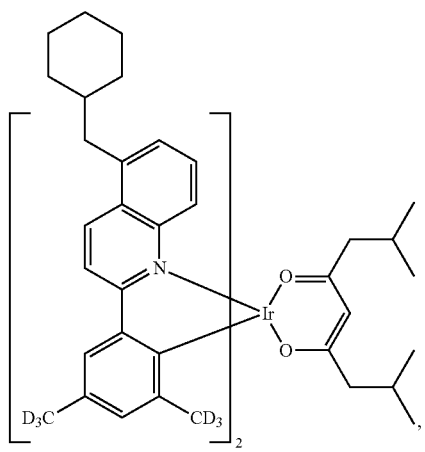
Compound II-61
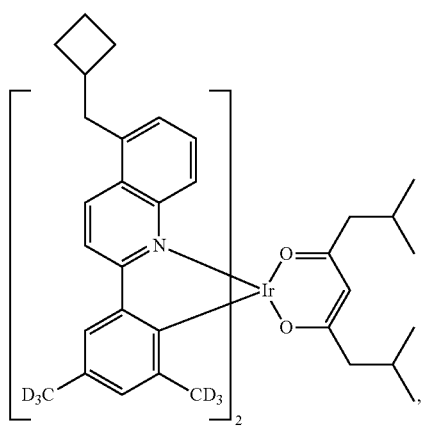
Compound II-64
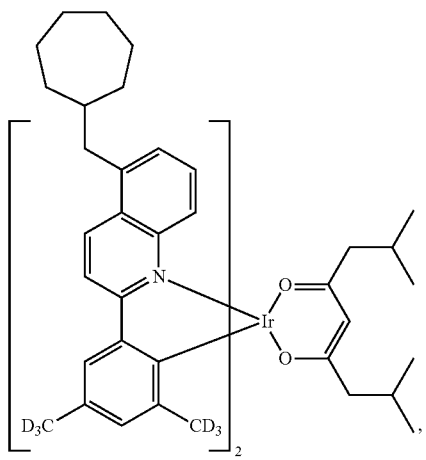

Compound II-65
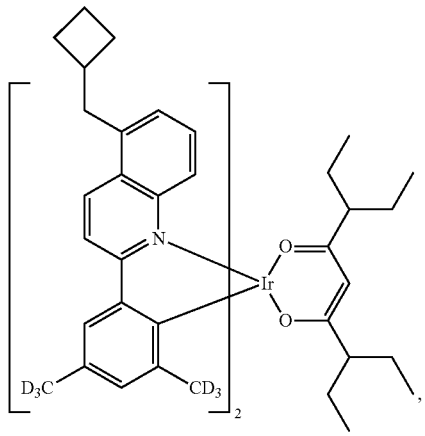
Compound II-66
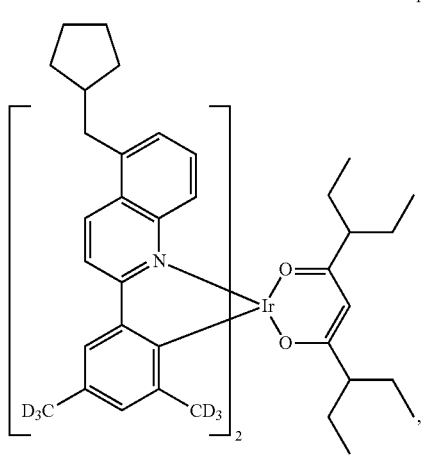
Compound II-67
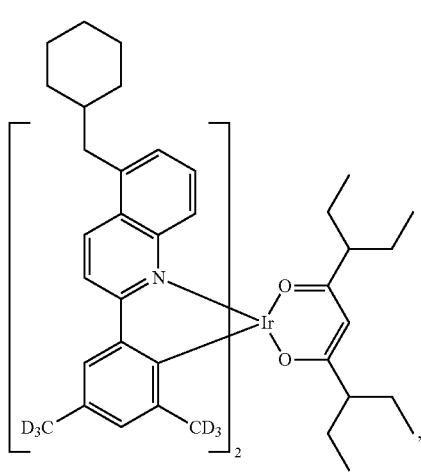
Compound II-68
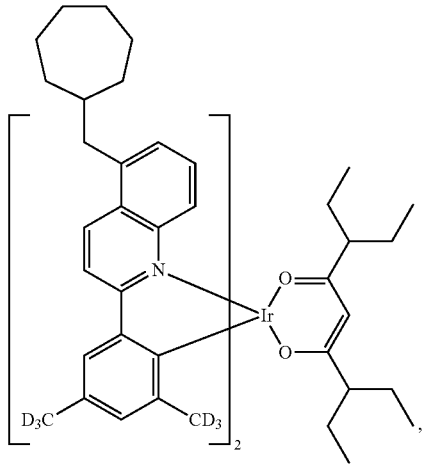
Compound II-69
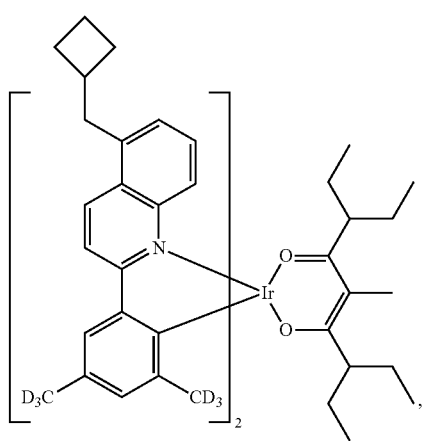
Compound II-70
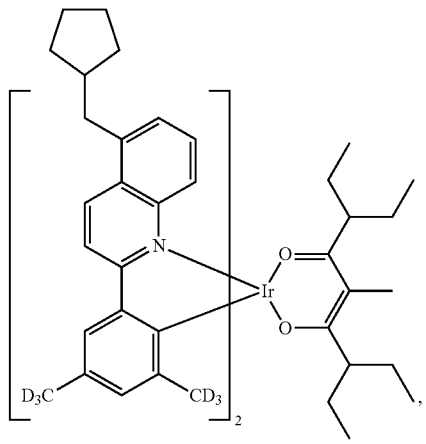

-continued

Compound II-71

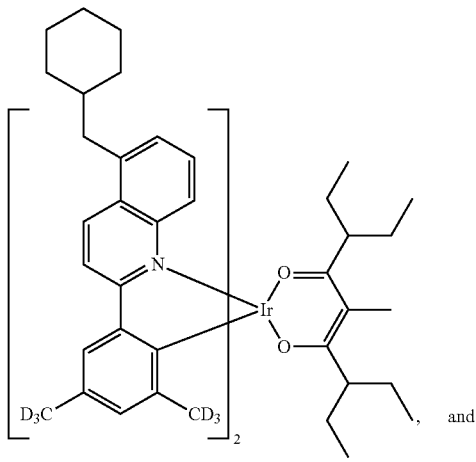

Compound II-72

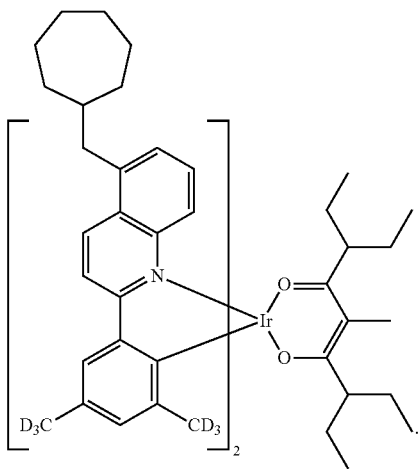

12. A first device comprising:
an anode;
a cathode; and
an organic layer, disposed between the anode and the cathode, comprising a compound having the formula:

Formula III

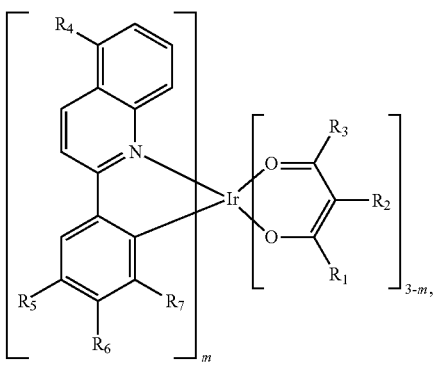

wherein $R_1$, $R_2$, $R_3$, $R_5$, $R_6$ and $R_7$ are independently selected from the group consisting of hydrogen, deuterium, alkyl, silyl, alkoxy, amino, alkenyl, alkynyl, arylkyl, aryl and heteroaryl;

wherein $R_4$ comprises an unsubstituted cycloalkyl group selected from the group consisting of cyclobutyl, cyclopentyl, cyclohexyl, and cycloheptyl; and wherein m is 1, 2, or 3.

13. The first device of claim 12, wherein each of $R_1$ and $R_3$ is a branched alkyl with branching at a position further than the α position to the carbonyl group.

14. The first device of claim 12, wherein each of $R_5$, $R_6$ and $R_7$ are independently selected from methyl and hydrogen, and at least one of $R_5$, $R_6$ and $R_7$ is methyl.

15. The first device of claim 12, wherein each of $R_5$ and $R_7$ are methyl, and $R_6$ is hydrogen.

16. The first device of claim 12, wherein each of $R_5$ and $R_6$ are methyl, and $R_7$ is hydrogen.

17. The first device of claim 12, wherein each of $R_5$, $R_6$, and $R_7$ are methyl.

18. The first device of claim 12, wherein the compound is selected from the group consisting of:

Compound II-1

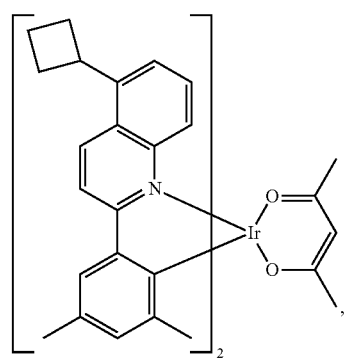

Compound II-2

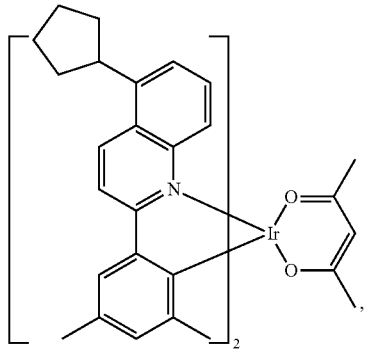

Compound II-3

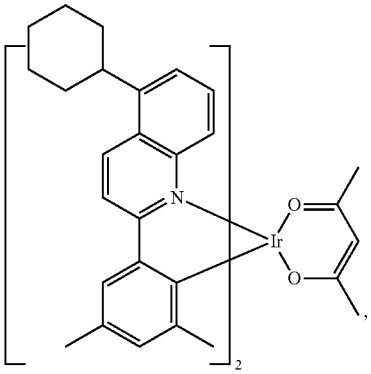

Compound II-4
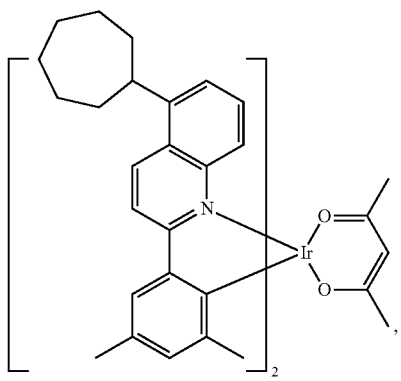
Compound II-5
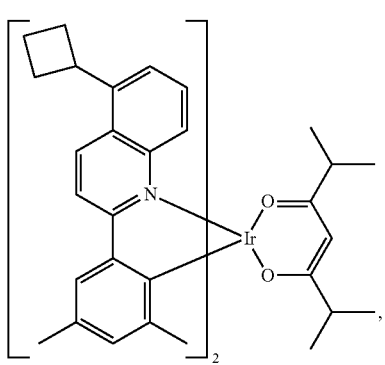
Compound II-6
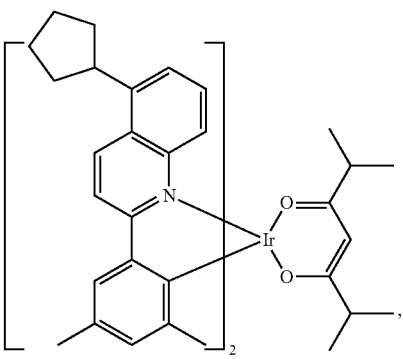
Compound II-7
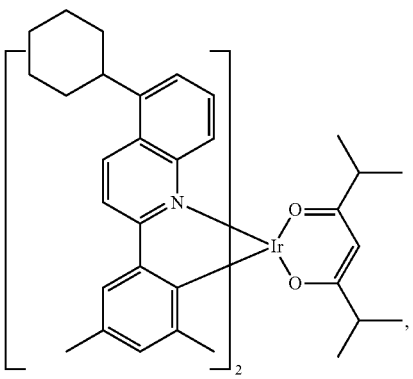
Compound II-8
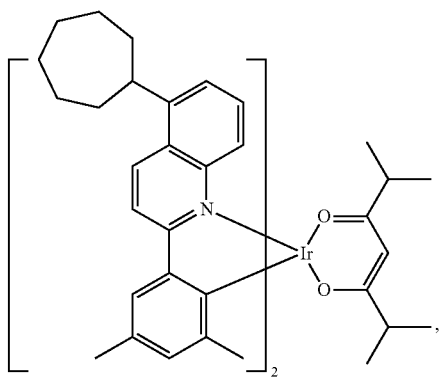
Compound II-9
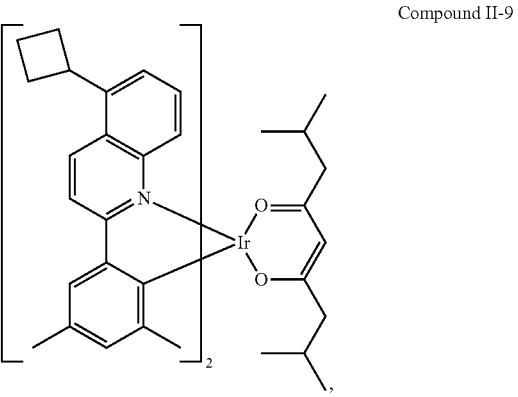
Compound II-10
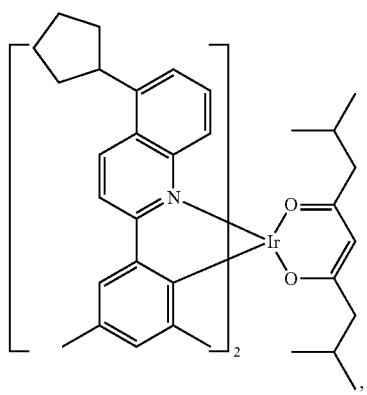
Compound II-11
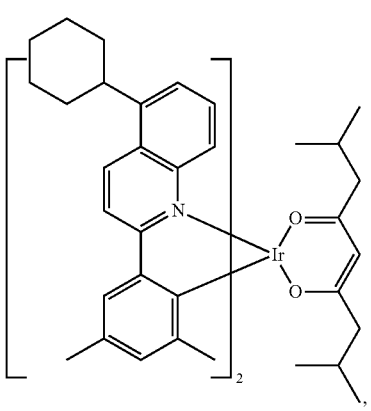

Compound II-12
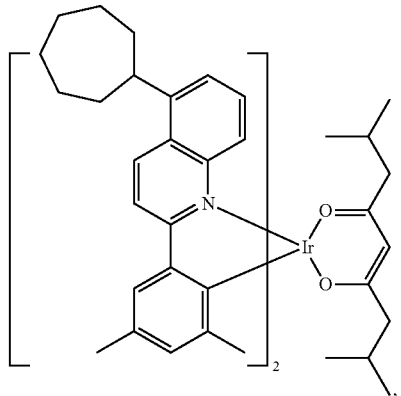
Compound II-13
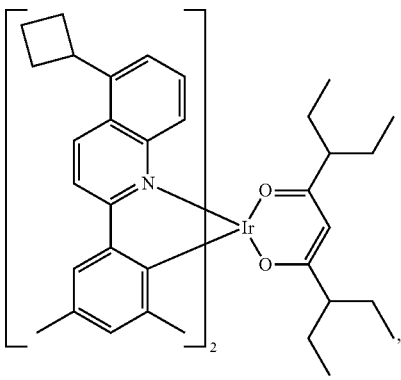
Compound II-14
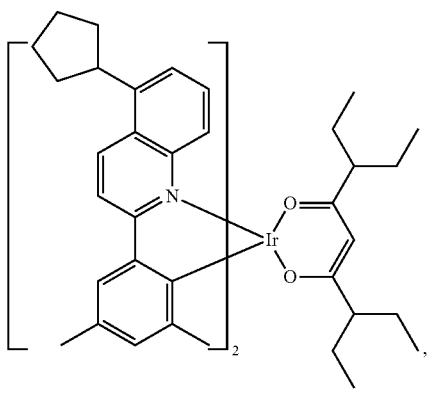
Compound II-15
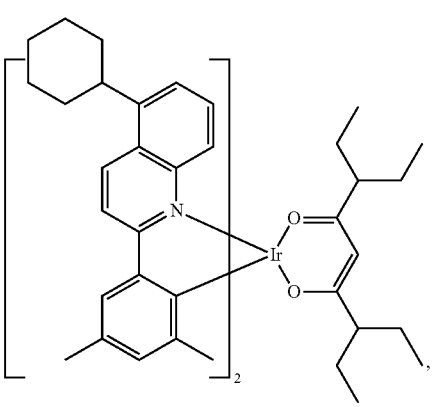
Compound II-16
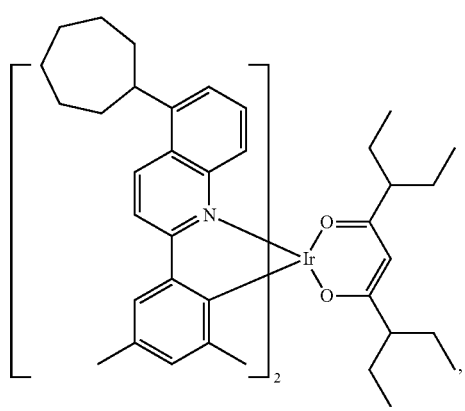
Compound II-17
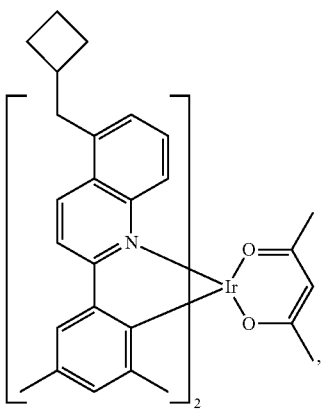
Compound II-18
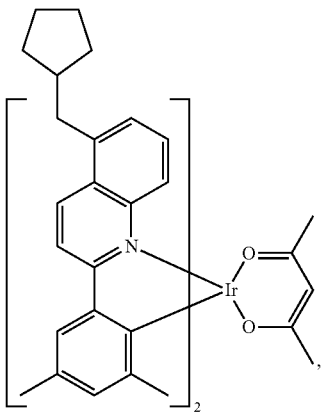

Compound II-19
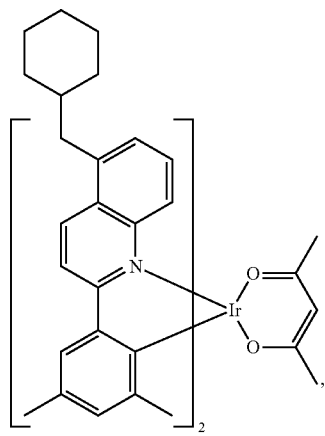
Compound II-20
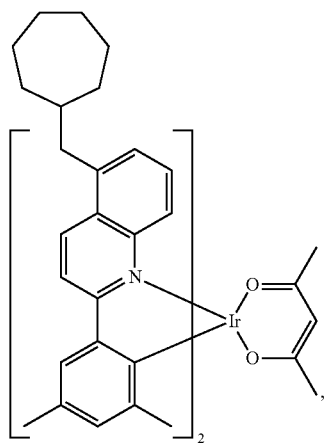
Compound II-21
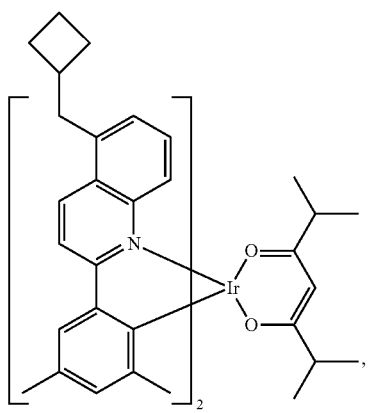
Compound II-22
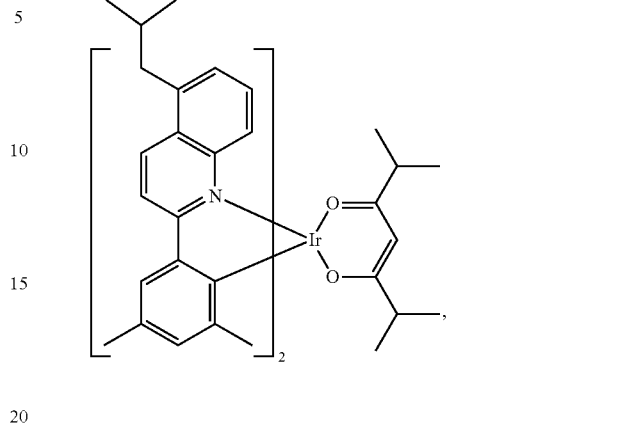
Compound II-23
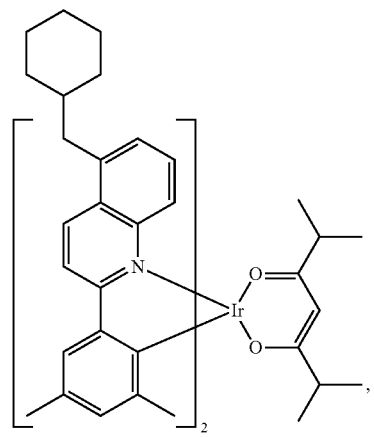
Compound II-24
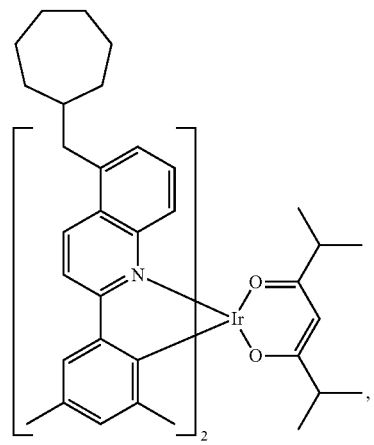

Compound II-25
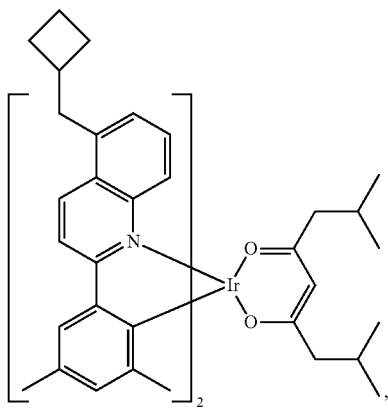
Compound II-26
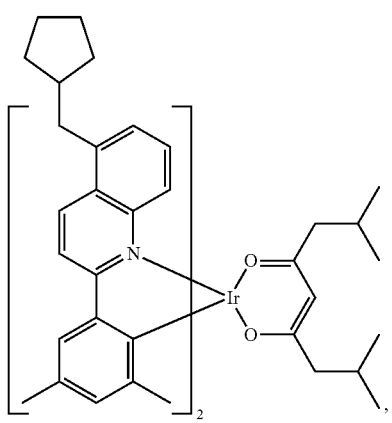
Compound II-27
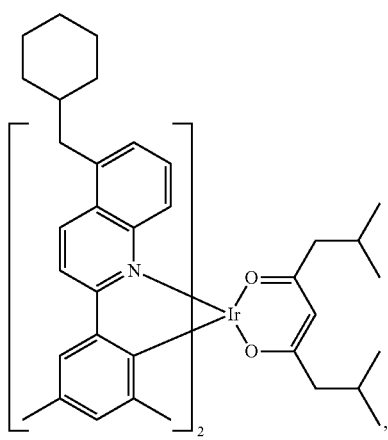
Compound II-28
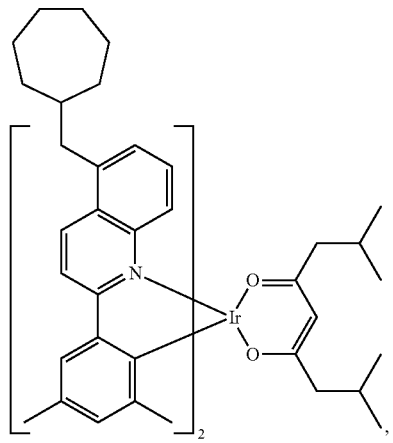
Compound II-29
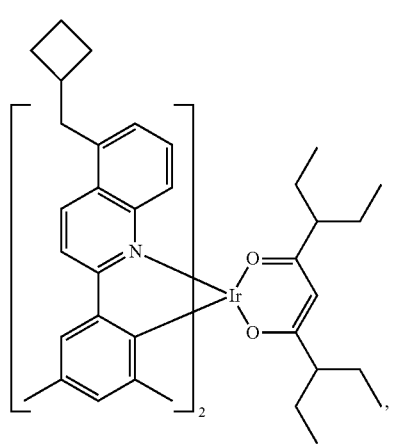
Compound II-30
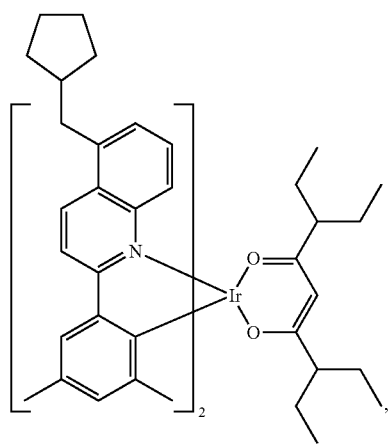

Compound II-31
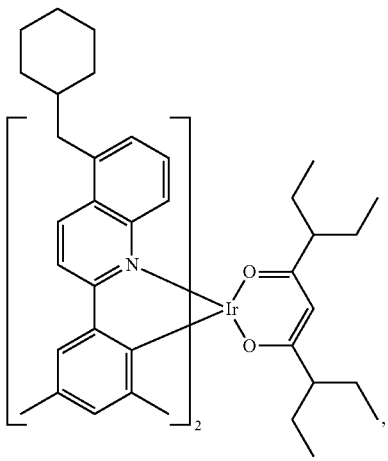
Compound II-32
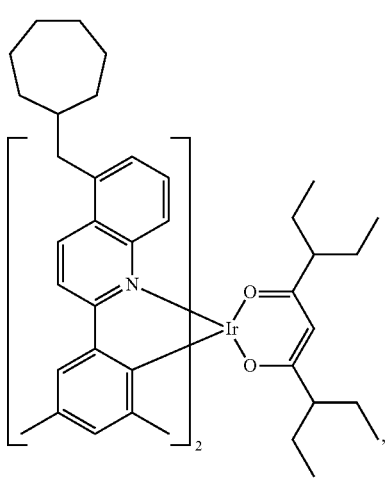
Compound II-33
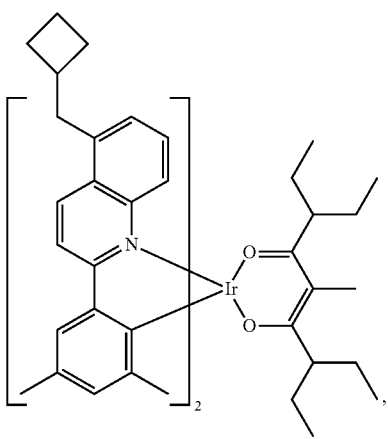
Compound II-34
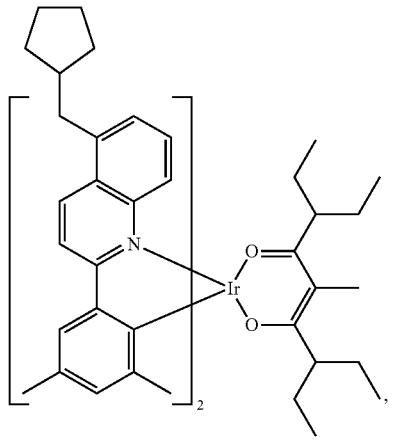
Compound II-35
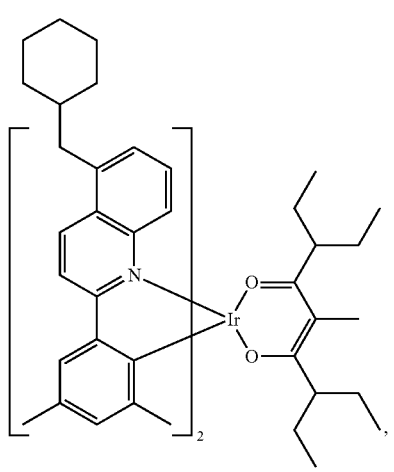
Compound II-36
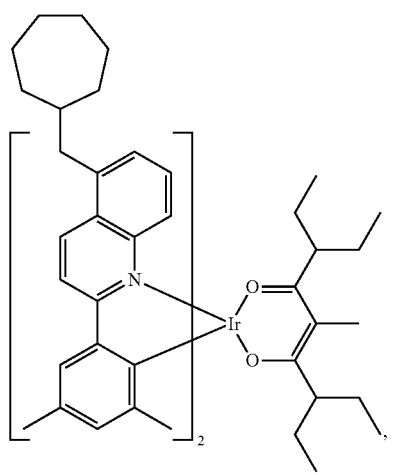

Compound II-37
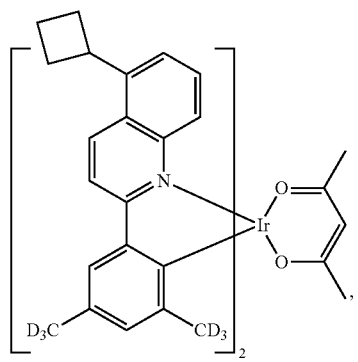
Compound II-41
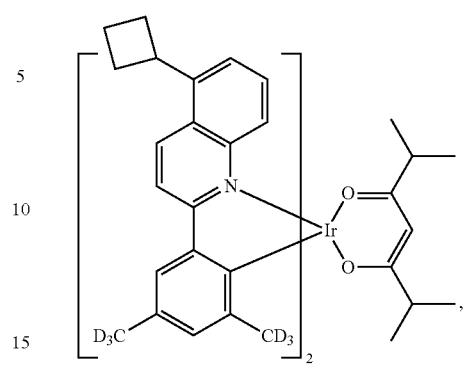
Compound II-38
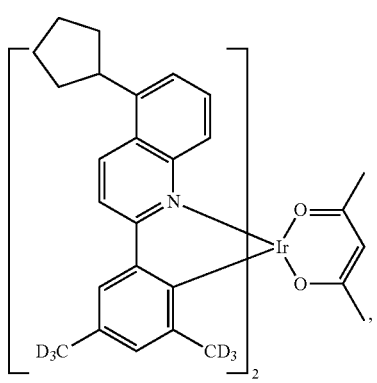
Compound II-42
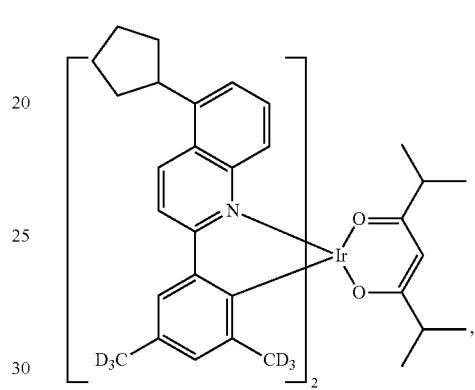
Compound II-39
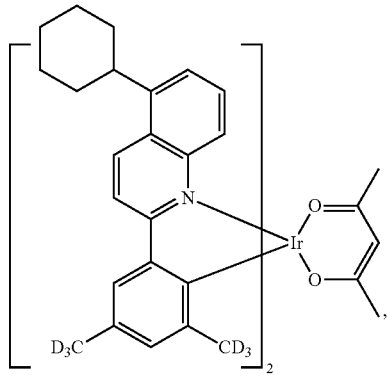
Compound II-43
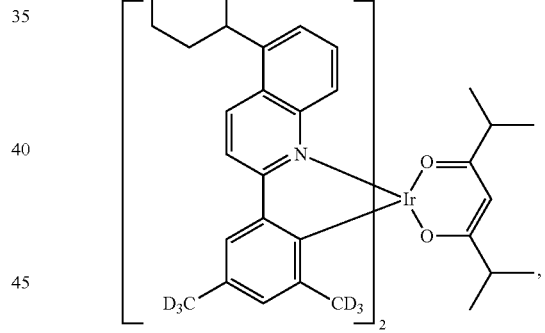
Compound II-40
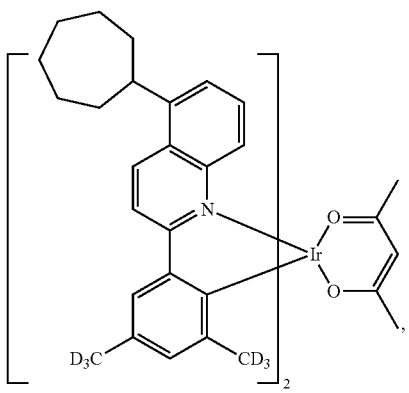
Compound II-44
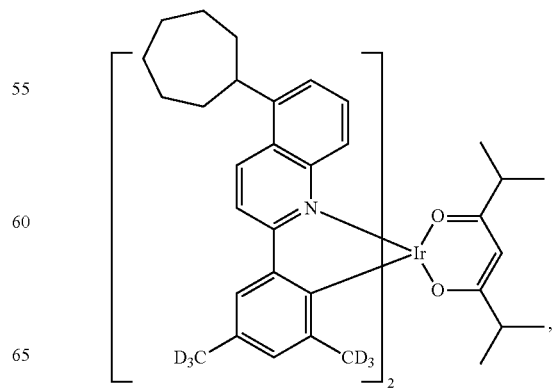

Compound II-45
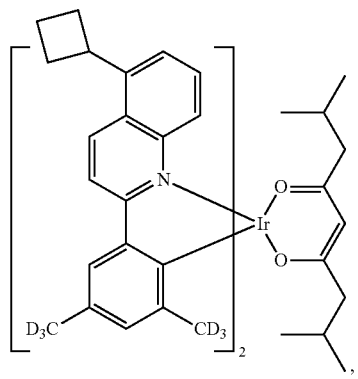
Compound II-46
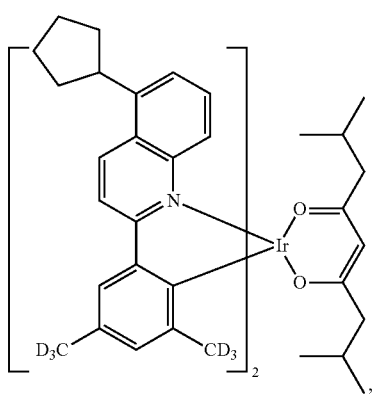
Compound II-47
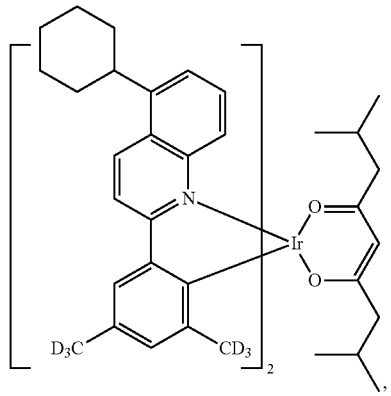
Compound II-48
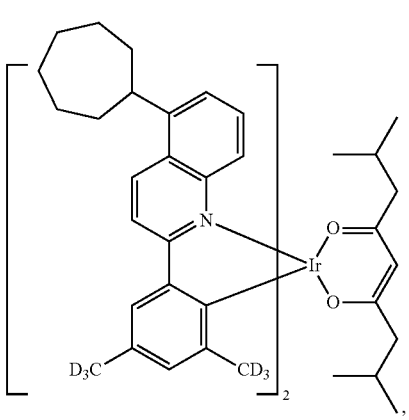
Compound II-49
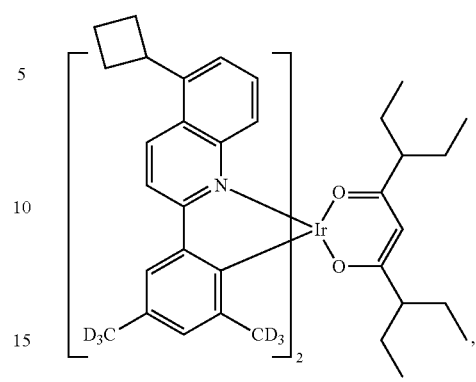
Compound II-50
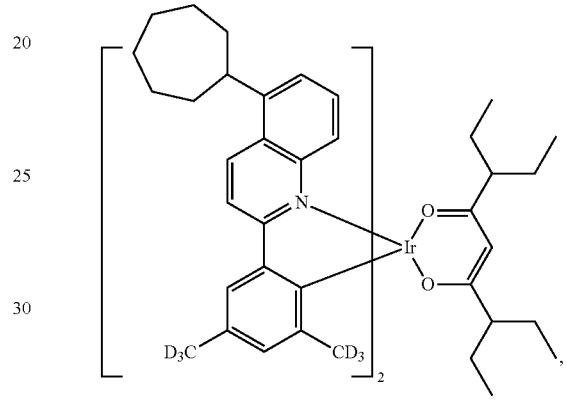
Compound II-51
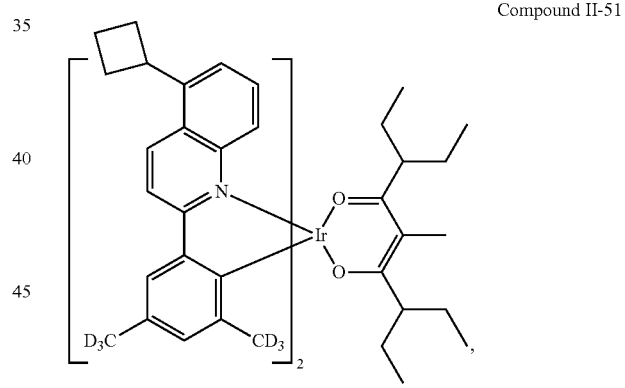
Compound II-52
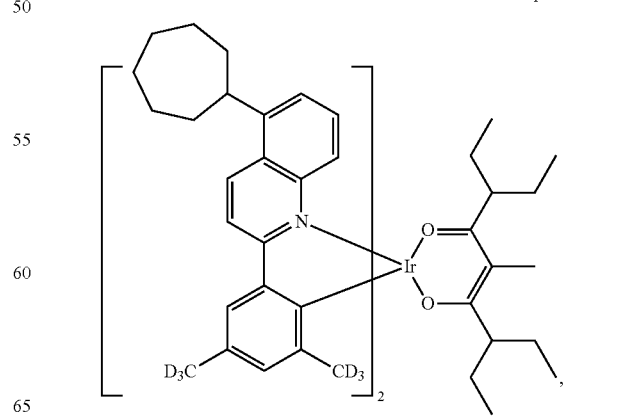

Compound II-53
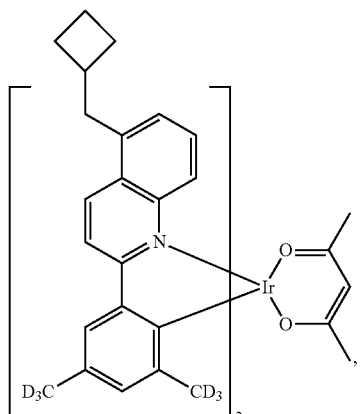
Compound II-54
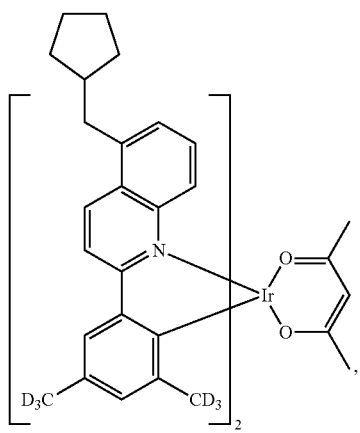
Compound II-55
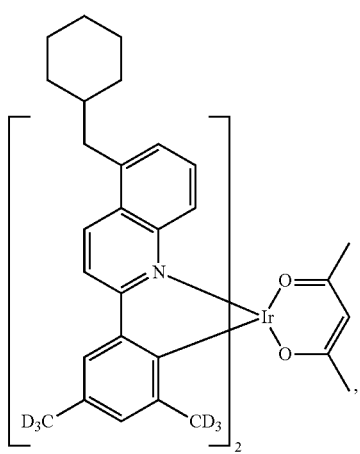
Compound II-56
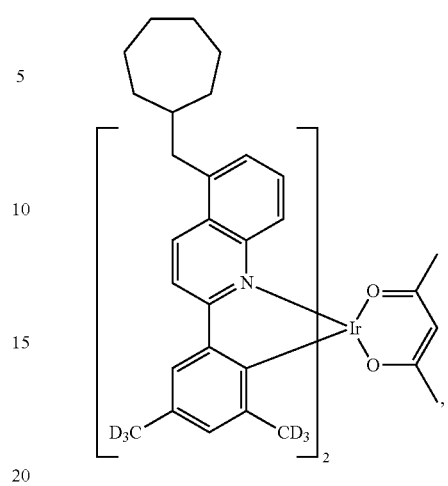
Compound II-57
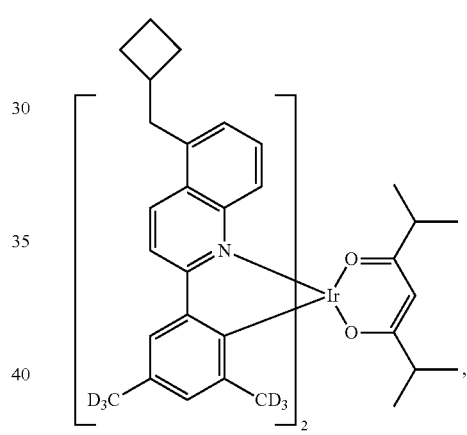
Compound II-58
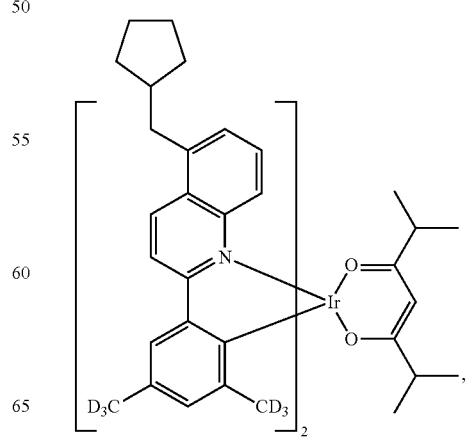

Compound II-59
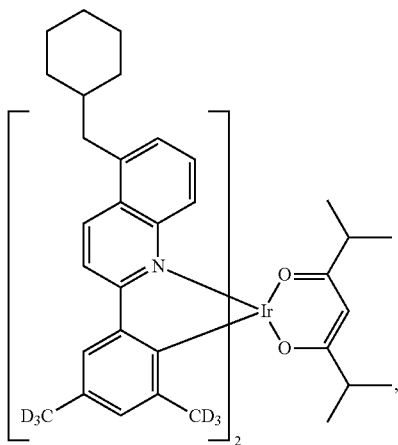
Compound II-62
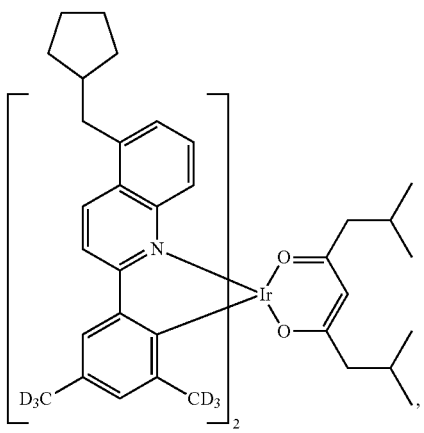
Compound II-60
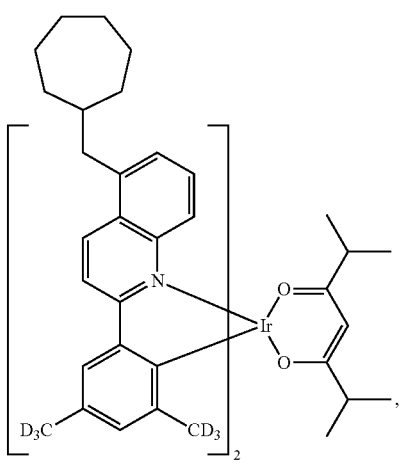
Compound II-63
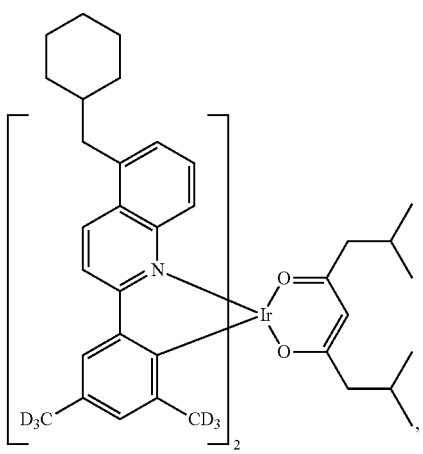
Compound II-61
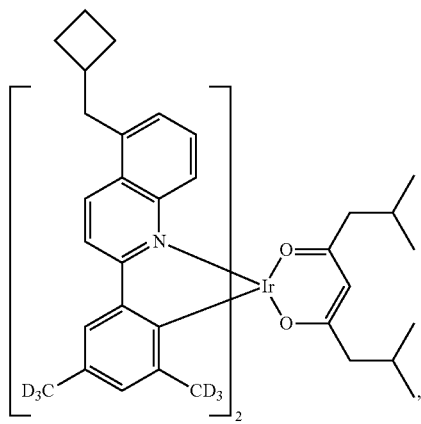
Compound II-64
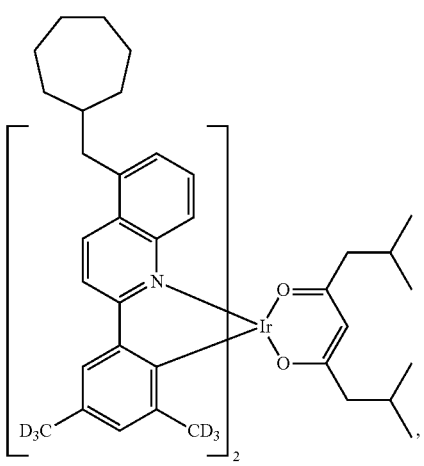

Compound II-65
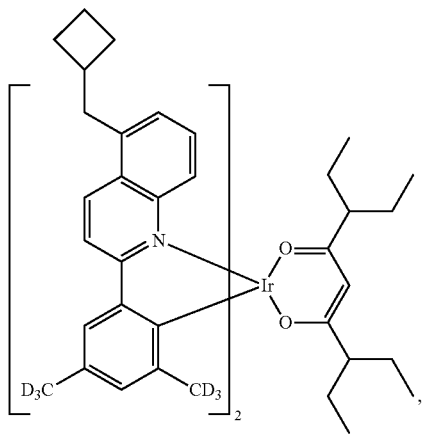
Compound II-66
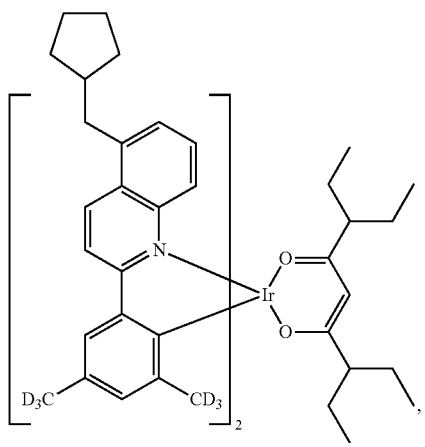
Compound II-67
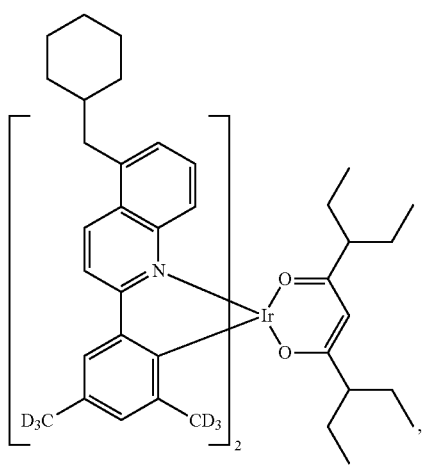
Compound II-68
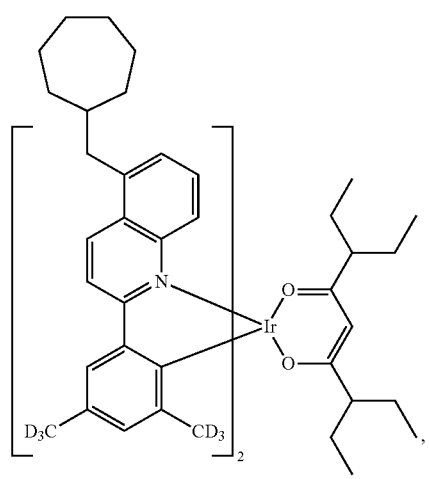
Compound II-69
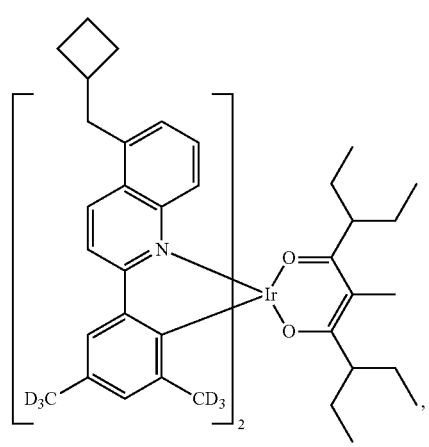
Compound II-70
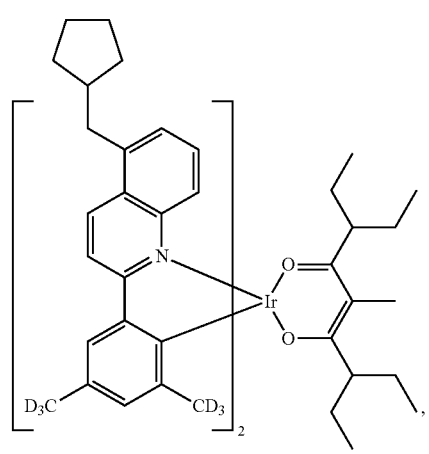

-continued

Compound II-71

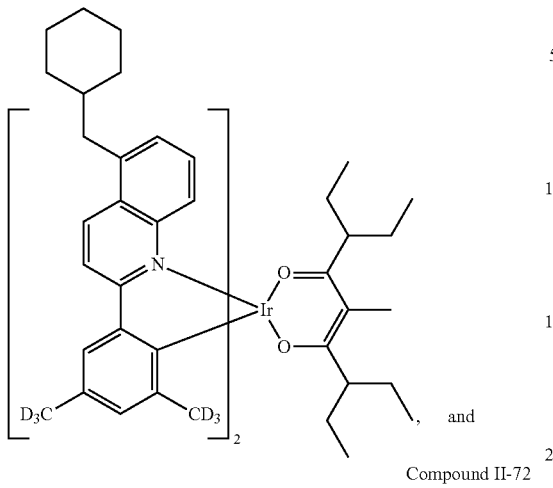

and

Compound II-72

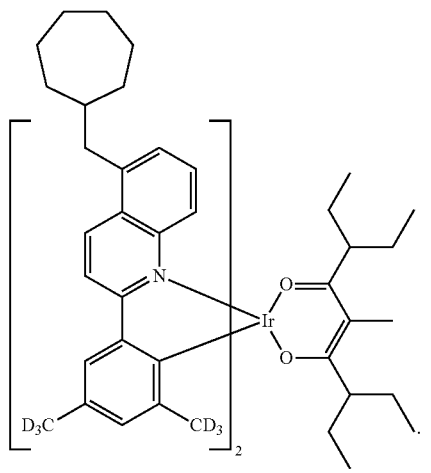

19. The first device of claim 12, wherein the organic layer is an emissive layer and the compound is an emissive dopant.

20. The first device of claim 19, wherein the organic layer further comprises a host.

21. The first device of claim 20, wherein the host is a metal 8-hydroxyquinolate.

22. The first device of claim 21, wherein the host is

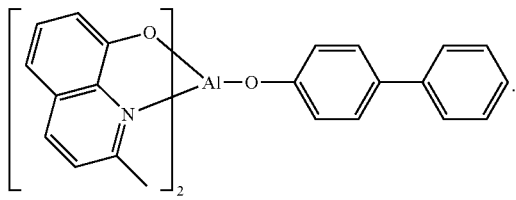

23. The first device of claim 12, wherein the first device is selected from the group consisting of a consumer product, an organic light emitting device, and combinations thereof.

* * * * *

UNITED STATES PATENT AND TRADEMARK OFFICE
CERTIFICATE OF CORRECTION

PATENT NO. : 10,008,677 B2  
APPLICATION NO. : 13/932546  
DATED : June 26, 2018  
INVENTOR(S) : Chuanjun Xia et al.

Page 1 of 4

It is certified that error appears in the above-identified patent and that said Letters Patent is hereby corrected as shown below:

In the Specification

Column 27, Lines 1-18, please delete the compound

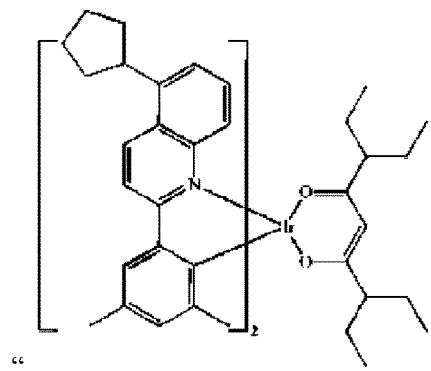

" and insert --

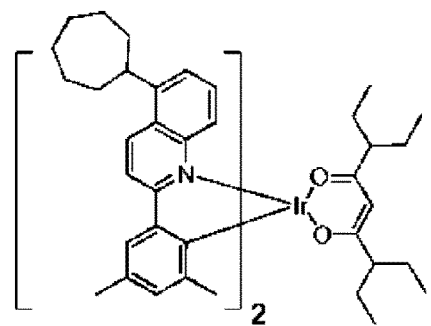

Compound II-14 --

Column 27, Lines 19-33, please delete the compound

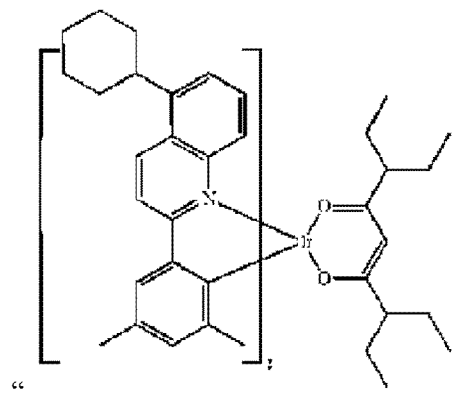

" and insert --

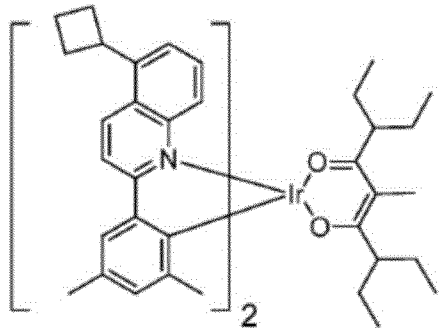

Compound II-15 --

Signed and Sealed this  
Eighteenth Day of September, 2018

Andrei Iancu  
*Director of the United States Patent and Trademark Office*

Column 27, Lines 34-51, please delete the compound
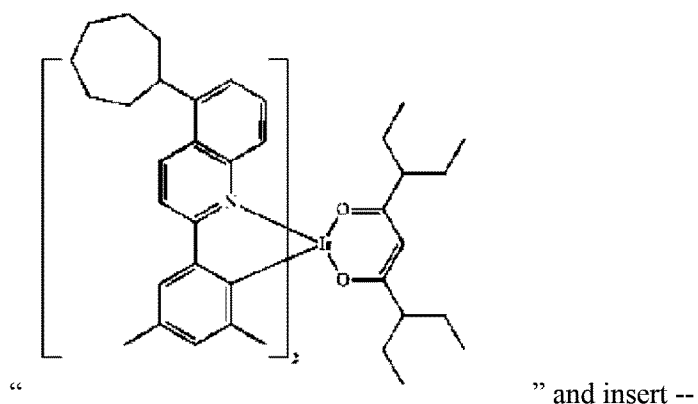 " and insert -- 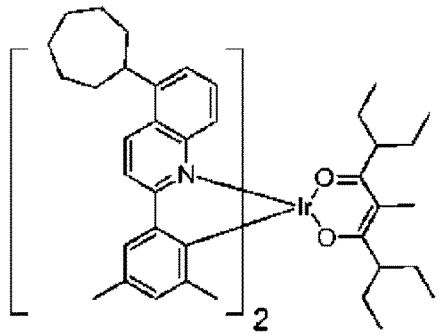 --
In the Claims
Column 129, Lines 18-33, please delete the compound
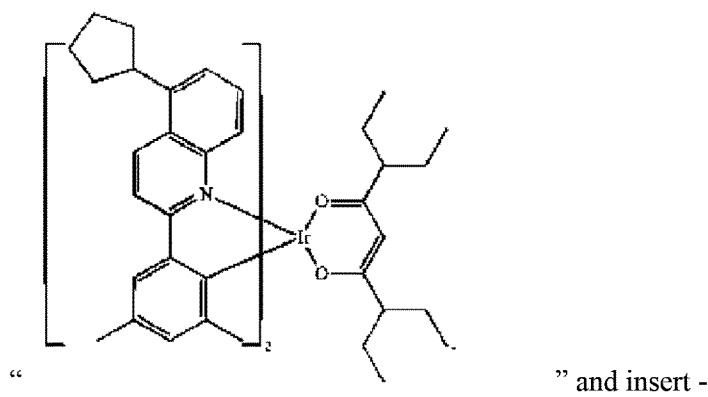 " and insert -- 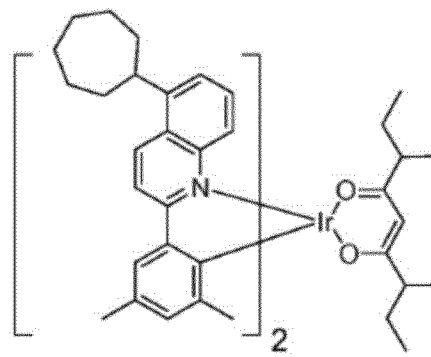 --
Column 129, Lines 34-49, please delete the compound
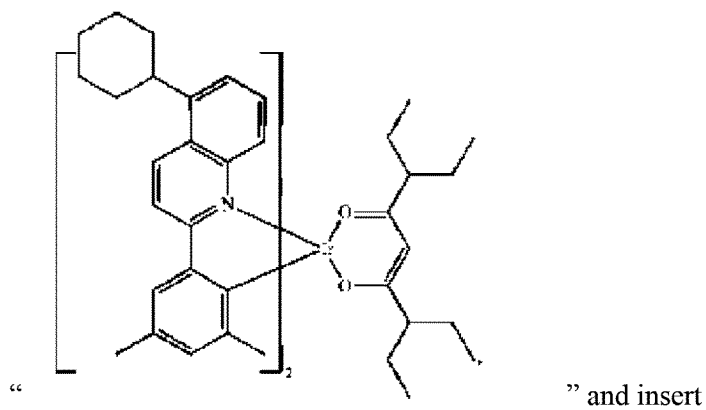 " and insert -- 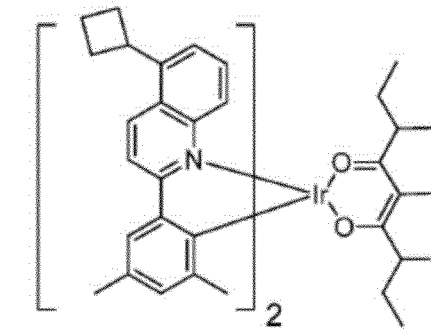 --
Column 129, Lines 50-67, please delete the compound

CERTIFICATE OF CORRECTION (continued)
U.S. Pat. No. 10,008,677 B2

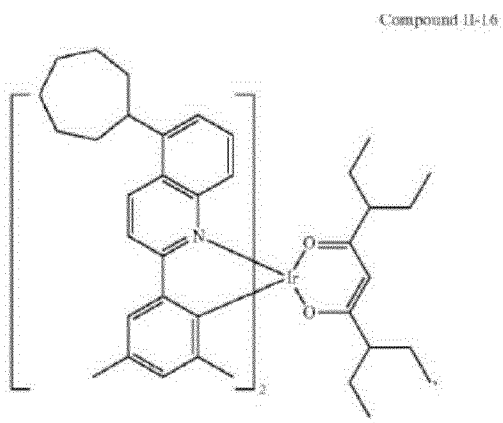

" and insert --

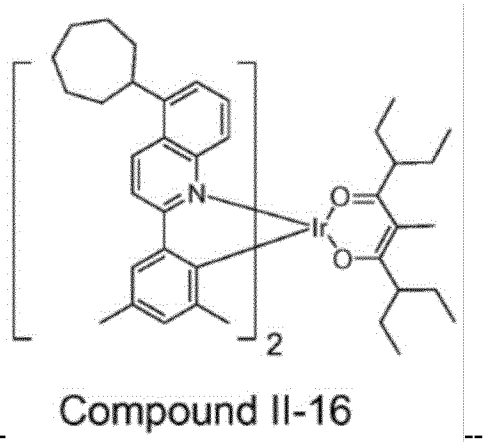

--

Column 151, Lines 34-49, please delete the compound

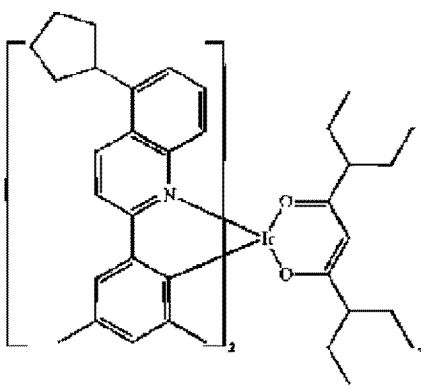

" and insert --

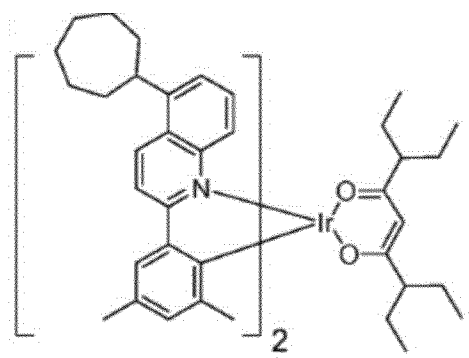

--

Column 151, Lines 50-67, please delete the compound

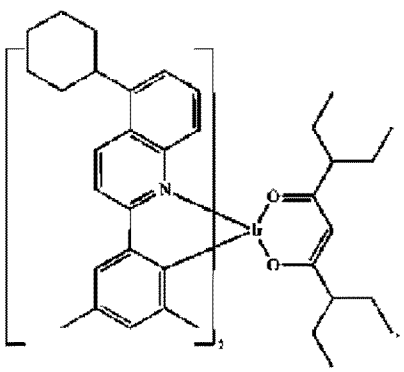

" and insert --

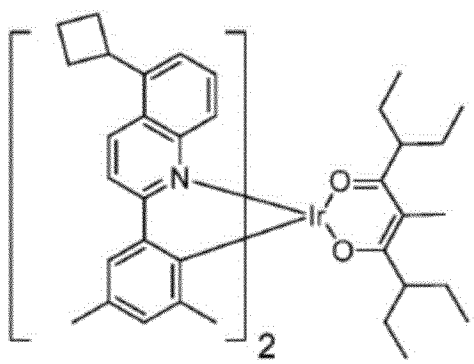

--

Column 152, Lines 1-24, please delete the compound

CERTIFICATE OF CORRECTION (continued)
U.S. Pat. No. 10,008,677 B2

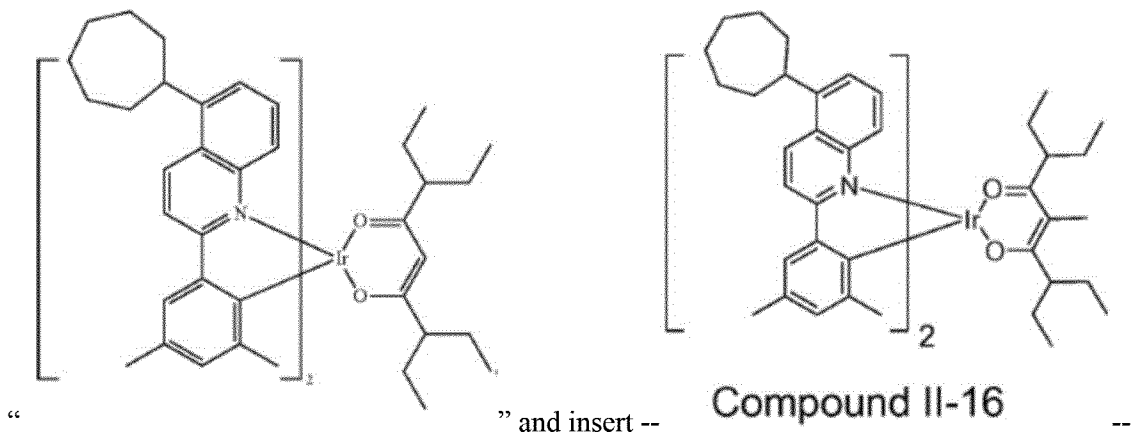

" " and insert -- Compound II-16 --